United States Patent
Zemel et al.

(10) Patent No.: US 9,707,213 B2
(45) Date of Patent: *Jul. 18, 2017

(54) COMPOSITIONS, METHODS AND KITS FOR REDUCING LIPID LEVELS

(71) Applicant: NuSirt Sciences, Inc., Nashville, TN (US)

(72) Inventors: Michael Zemel, Knoxville, TN (US); Antje Bruckbauer, Knoxville, TN (US)

(73) Assignee: NuSirt Sciences, Inc., Nashiville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,125

(22) Filed: Jul. 8, 2016

(65) Prior Publication Data

US 2017/0000780 A1    Jan. 5, 2017

Related U.S. Application Data

(63) Continuation of application No. 14/472,081, filed on Aug. 28, 2014, now Pat. No. 9,408,834, which is a
(Continued)

(51) Int. Cl.
| | |
|---|---|
| *A61K 31/435* | (2006.01) |
| *A23L 33/15* | (2016.01) |
| *A23L 33/175* | (2016.01) |
| *A61K 47/18* | (2017.01) |
| *A61K 31/455* | (2006.01) |

(Continued)

(52) U.S. Cl.
CPC ............ *A61K 31/435* (2013.01); *A23L 33/15* (2016.08); *A23L 33/175* (2016.08); *A61K 31/05* (2013.01); *A61K 31/198* (2013.01); *A61K 31/455* (2013.01); *A61K 31/706* (2013.01);
(Continued)

(58) Field of Classification Search
CPC .. A61K 31/435; A61K 47/183; A61K 31/455; A61K 31/198; A61K 31/706; A61K 31/05; A61K 45/06; A23L 33/15; A23L 33/175; A23V 2002/00
See application file for complete search history.

(56) References Cited

U.S. PATENT DOCUMENTS

| | | | |
|---|---|---|---|
| 3,810,994 A | 5/1974 | Wiegand | |
| 3,936,527 A | 2/1976 | Alper | |

(Continued)

FOREIGN PATENT DOCUMENTS

| | | |
|---|---|---|
| CN | 102077936 A | 6/2011 |
| EP | 1685833 A1 | 8/2006 |

(Continued)

OTHER PUBLICATIONS

Carlson, LA. Nicotinic acid: the broad-spectrum lipid drug. A 50th anniversary review. J Intern Med. Aug. 2005;258(2):94-114.
(Continued)

*Primary Examiner* — Trevor Love
(74) *Attorney, Agent, or Firm* — Wilson Sonsini Goodrich & Rosati

(57) ABSTRACT

Compositions, methods, and kits useful for treating hyperlipidemic conditions are provided herein. Such compositions can contain synergizing amounts of nicotinic acid, nicotinamide riboside and/or nicotinic acid metabolites in combination with leucine and/or a leucine metabolite, with or without resveratrol.

27 Claims, 15 Drawing Sheets
(2 of 15 Drawing Sheet(s) Filed in Color)

Nicotinic Acid

Nicotinamide Riboside

Related U.S. Application Data continuation-in-part of application No. PCT/US2014/026816, filed on Mar. 13, 2014.

(60) Provisional application No. 61/800,363, filed on Mar. 15, 2013.

(51) Int. Cl.
 A61K 31/198 (2006.01)
 A61K 31/706 (2006.01)
 A61K 31/05 (2006.01)
 A61K 45/06 (2006.01)

(52) U.S. Cl.
 CPC ............ *A61K 45/06* (2013.01); *A61K 47/183* (2013.01); *A23V 2002/00* (2013.01)

(56) References Cited

U.S. PATENT DOCUMENTS

| | | |
|---|---|---|
| 4,606,909 A | 8/1986 | Bechgaard et al. |
| 4,769,027 A | 9/1988 | Baker et al. |
| 4,897,268 A | 1/1990 | Tice et al. |
| 4,992,470 A | 2/1991 | Nissen |
| 5,069,204 A | 12/1991 | Smith et al. |
| 5,087,624 A | 2/1992 | Boynton et al. |
| 5,250,534 A | 10/1993 | Bell et al. |
| 5,339,771 A | 8/1994 | Axelrod |
| 5,395,626 A | 3/1995 | Kotwal et al. |
| 5,419,283 A | 5/1995 | Leo |
| 5,616,569 A | 4/1997 | Reinhart |
| 5,776,913 A | 7/1998 | Ogilvie et al. |
| 5,886,012 A | 3/1999 | Pang et al. |
| 5,968,569 A | 10/1999 | Cavadini et al. |
| 6,004,996 A | 12/1999 | Shah et al. |
| 6,031,000 A | 2/2000 | Nissen et al. |
| 6,048,903 A | 4/2000 | Toppo |
| 6,063,414 A | 5/2000 | Jones et al. |
| 6,063,820 A | 5/2000 | Cavazza |
| 6,224,861 B1 | 5/2001 | Abe et al. |
| 6,280,779 B1 | 8/2001 | Nadeau et al. |
| 6,338,862 B1 | 1/2002 | Niazi |
| 6,369,042 B1 | 4/2002 | Oberthuer et al. |
| 6,384,087 B1 | 5/2002 | Zemel et al. |
| 6,387,419 B1 | 5/2002 | Christensen |
| 6,469,012 B1 | 10/2002 | Ellis et al. |
| 6,517,877 B2 | 2/2003 | Gannon |
| 6,527,711 B1 | 3/2003 | Stivoric et al. |
| 6,595,929 B2 | 7/2003 | Stivoric et al. |
| 6,605,038 B1 | 8/2003 | Teller et al. |
| 6,635,268 B2 | 10/2003 | Peery et al. |
| 6,638,545 B1 | 10/2003 | Rombi |
| 6,676,967 B1 | 1/2004 | Cefali et al. |
| 6,764,697 B1 | 7/2004 | Jao et al. |
| 6,790,869 B2 | 9/2004 | Ghai et al. |
| 6,797,283 B1 | 9/2004 | Edgren et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,939,556 B2 | 9/2005 | Lautenbach |
| 7,020,508 B2 | 3/2006 | Stivoric et al. |
| 7,109,198 B2 | 9/2006 | Gadde et al. |
| 7,141,254 B2 | 11/2006 | Bhaskaran et al. |
| 7,153,262 B2 | 12/2006 | Stivoric et al. |
| 7,230,009 B2 | 6/2007 | Haque et al. |
| 7,261,690 B2 | 8/2007 | Teller et al. |
| 7,285,090 B2 | 10/2007 | Stivoric et al. |
| 7,354,738 B2 | 4/2008 | Spiegelman et al. |
| 7,495,101 B2 | 2/2009 | Fischesser et al. |
| 7,502,643 B2 | 3/2009 | Farringdon et al. |
| 7,674,485 B2 | 3/2010 | Bhaskaran et al. |
| 7,689,437 B1 | 3/2010 | Teller et al. |
| 7,722,905 B2 | 5/2010 | Khoo |
| 7,744,930 B2 | 6/2010 | Fisher et al. |
| 7,829,556 B2 | 11/2010 | Bemis et al. |
| 7,855,289 B2 | 12/2010 | Nunes et al. |
| 7,870,856 B2 | 1/2011 | Boeck |
| 7,893,086 B2 | 2/2011 | Bemis et al. |
| 7,959,567 B2 | 6/2011 | Stivoric et al. |
| 7,989,007 B2 | 8/2011 | Giuliano et al. |
| 8,008,458 B2 | 8/2011 | Zaloga et al. |
| 8,017,634 B2 | 9/2011 | Sinclair et al. |
| 8,044,198 B2 | 10/2011 | Nunes et al. |
| 8,073,707 B2 | 12/2011 | Teller et al. |
| 8,088,043 B2 | 1/2012 | Andren et al. |
| 8,088,044 B2 | 1/2012 | Tchao et al. |
| 8,088,928 B2 | 1/2012 | Nunes et al. |
| 8,093,401 B2 | 1/2012 | Nunes et al. |
| 8,106,097 B2 | 1/2012 | Najib et al. |
| 8,157,731 B2 | 4/2012 | Teller et al. |
| 8,192,767 B2 | 6/2012 | Carta |
| 8,275,635 B2 | 9/2012 | Stivoric et al. |
| 8,299,083 B2 | 10/2012 | Kass et al. |
| 8,369,936 B2 | 2/2013 | Farringdon et al. |
| 8,370,549 B2 | 2/2013 | Burton et al. |
| 8,378,090 B2 | 2/2013 | Petiard et al. |
| 8,382,590 B2 | 2/2013 | Stivoric et al. |
| 8,398,546 B2 | 3/2013 | Pacione et al. |
| 8,403,845 B2 | 3/2013 | Stivoric et al. |
| 8,408,436 B2 | 4/2013 | Berry et al. |
| 8,469,862 B2 | 6/2013 | Andren et al. |
| 8,517,896 B2 | 8/2013 | Robinette et al. |
| 8,557,869 B2 | 10/2013 | Yamka et al. |
| 8,562,489 B2 | 10/2013 | Burton et al. |
| 8,597,677 B2 | 12/2013 | Yamka et al. |
| 8,617,886 B2 | 12/2013 | Zemel et al. |
| 8,623,924 B2 | 1/2014 | Zemel et al. |
| 9,072,692 B2 | 7/2015 | Zemel et al. |
| 9,198,454 B2 | 12/2015 | Zemel et al. |
| 9,198,883 B1 | 12/2015 | Zemel et al. |
| 9,351,967 B2 | 5/2016 | Zemel et al. |
| 9,408,410 B2 | 8/2016 | Zemel et al. |
| 9,408,834 B2 | 8/2016 | Zemel et al. |
| 9,585,876 B2 | 3/2017 | Zemel et al. |
| 2001/0043983 A1 | 11/2001 | Hamilton |
| 2003/0035882 A1 | 2/2003 | McDaniel et al. |
| 2003/0187055 A1 | 10/2003 | Riker et al. |
| 2004/0120983 A1 | 6/2004 | Connolly |
| 2004/0186046 A1 | 9/2004 | Burgess et al. |
| 2005/0042362 A1 | 2/2005 | Clark et al. |
| 2005/0064070 A1 | 3/2005 | Liebrecht |
| 2005/0100617 A1 | 5/2005 | Malnoe et al. |
| 2005/0215882 A1 | 9/2005 | Chenevert et al. |
| 2006/0051416 A1 | 3/2006 | Rastogi et al. |
| 2006/0111435 A1 | 5/2006 | Sinclair et al. |
| 2006/0159746 A1 | 7/2006 | Troup et al. |
| 2006/0165824 A1 | 7/2006 | Khambe |
| 2006/0188611 A1 | 8/2006 | Unlu et al. |
| 2006/0194743 A1 | 8/2006 | Oku et al. |
| 2006/0205633 A1 | 9/2006 | Nishitani et al. |
| 2007/0014833 A1 | 1/2007 | Milburn et al. |
| 2007/0065512 A1 | 3/2007 | Dedhiya et al. |
| 2007/0077310 A1 | 4/2007 | Zemel et al. |
| 2007/0092577 A1 | 4/2007 | Zemel et al. |
| 2007/0110850 A1 | 5/2007 | Rifkin |
| 2007/0190171 A1 | 8/2007 | Yamka et al. |
| 2007/0203083 A1 | 8/2007 | Mootha et al. |
| 2007/0244202 A1 | 10/2007 | Murase |
| 2007/0286909 A1 | 12/2007 | Smith et al. |
| 2008/0069862 A1 | 3/2008 | Hurwitz |
| 2008/0076828 A1 | 3/2008 | Dalton et al. |
| 2008/0102137 A1 | 5/2008 | Guffey |
| 2008/0176822 A1 | 7/2008 | Chen |
| 2008/0220092 A1 | 9/2008 | DiPierro et al. |
| 2008/0233245 A1 | 9/2008 | White et al. |
| 2008/0268038 A1 | 10/2008 | Wolfe |
| 2008/0286254 A1 | 11/2008 | Sakamoto et al. |
| 2009/0012183 A1 | 1/2009 | Draijer et al. |
| 2009/0017130 A1 | 1/2009 | Yamka et al. |
| 2009/0054450 A1 | 2/2009 | Currie et al. |
| 2009/0074827 A1 | 3/2009 | Scherl et al. |
| 2009/0105246 A1 | 4/2009 | Bemis et al. |
| 2009/0142336 A1 | 6/2009 | Walsh et al. |
| 2009/0156648 A1 | 6/2009 | Molino et al. |
| 2009/0163476 A1 | 6/2009 | Milburn et al. |

(56) References Cited

U.S. PATENT DOCUMENTS

| | | |
|---|---|---|
| 2009/0182036 A1 | 7/2009 | Krammer-Lukas |
| 2009/0197820 A1 | 8/2009 | Wolfe et al. |
| 2009/0230013 A1 | 9/2009 | Born et al. |
| 2010/0009992 A1 | 1/2010 | Birnberg et al. |
| 2010/0158956 A1 | 6/2010 | Komorowski |
| 2010/0173024 A1 | 7/2010 | McDaniel |
| 2010/0204204 A1 | 8/2010 | Zaworotko et al. |
| 2010/0210692 A1 | 8/2010 | Farmer et al. |
| 2010/0261793 A1 | 10/2010 | Caterson et al. |
| 2010/0303966 A1 | 12/2010 | Sunvold et al. |
| 2010/0303967 A1 | 12/2010 | Sunvold et al. |
| 2010/0304003 A1 | 12/2010 | Friesen et al. |
| 2010/0316679 A1 | 12/2010 | Sinclair et al. |
| 2010/0324002 A1 | 12/2010 | Fox et al. |
| 2011/0020443 A1 | 1/2011 | Liu et al. |
| 2011/0027416 A1 | 2/2011 | Sunvold et al. |
| 2011/0033559 A1 | 2/2011 | Zemel et al. |
| 2011/0038948 A1 | 2/2011 | Zemel et al. |
| 2011/0064712 A1 | 3/2011 | Amato |
| 2011/0064720 A1 | 3/2011 | Amato |
| 2011/0070258 A1 | 3/2011 | Jimenez Del Rio et al. |
| 2011/0082189 A1 | 4/2011 | Sinclair et al. |
| 2011/0111066 A1 | 5/2011 | Ferguson et al. |
| 2011/0112047 A1 | 5/2011 | Evans et al. |
| 2011/0130387 A1 | 6/2011 | Nunes et al. |
| 2011/0165125 A1 | 7/2011 | Pan |
| 2011/0208153 A1 | 8/2011 | Alvey |
| 2012/0058088 A1 | 3/2012 | Sardi |
| 2012/0129785 A1 | 5/2012 | Fleuranges et al. |
| 2012/0177730 A1 | 7/2012 | Baron et al. |
| 2012/0225139 A1 | 9/2012 | Ferguson et al. |
| 2012/0289598 A1 | 11/2012 | Yamka et al. |
| 2012/0301559 A1 | 11/2012 | Pridmore-Merten et al. |
| 2013/0017283 A1 | 1/2013 | Zemel et al. |
| 2013/0017284 A1 | 1/2013 | Zemel et al. |
| 2013/0045193 A1 | 2/2013 | Gonzalez et al. |
| 2013/0052286 A1 | 2/2013 | Wada et al. |
| 2013/0151196 A1 | 6/2013 | Yuen et al. |
| 2013/0158369 A1 | 6/2013 | Yuen et al. |
| 2013/0237605 A1 | 9/2013 | Zemel et al. |
| 2013/0323287 A1 | 12/2013 | Komorowski |
| 2014/0057017 A1 | 2/2014 | Yamka et al. |
| 2014/0148488 A1 | 5/2014 | Zemel et al. |
| 2015/0056274 A1 | 2/2015 | Zemel et al. |
| 2016/0008329 A1 | 1/2016 | Zemel et al. |
| 2016/0067201 A1 | 3/2016 | Zemel et al. |
| 2016/0279130 A1 | 9/2016 | Zemel et al. |
| 2016/0338983 A1 | 11/2016 | Zemel et al. |
| 2017/0000777 A1 | 1/2017 | Zemel et al. |
| 2017/0065545 A1 | 3/2017 | Zemel et al. |

FOREIGN PATENT DOCUMENTS

| | | |
|---|---|---|
| EP | 1818055 A1 | 8/2007 |
| EP | 2308493 A1 | 4/2011 |
| FR | 2710243 A1 | 3/1995 |
| GB | 1584539 A | 2/1981 |
| JP | 3219838 B2 | 10/2001 |
| JP | 2005097273 A | 4/2005 |
| JP | 2007306851 A | 11/2007 |
| JP | 2008063321 A | 3/2008 |
| WO | WO-2004056208 A1 | 7/2004 |
| WO | WO-2004082401 A1 | 9/2004 |
| WO | WO-2005049006 A1 | 6/2005 |
| WO | WO-2005065667 A2 | 7/2005 |
| WO | WO-2007146124 A2 | 12/2007 |
| WO | WO-2007146313 A1 | 12/2007 |
| WO | WO-2011051974 A1 | 5/2011 |
| WO | WO-2012097064 A1 | 7/2012 |
| WO | WO 2013/028547 A1 | 2/2013 |
| WO | WO-2013134736 A1 | 9/2013 |
| WO | WO-2013169007 A1 | 11/2013 |
| WO | WO-2014113404 A1 | 7/2014 |
| WO | WO 2014/152016 A1 | 9/2014 |
| WO | WO-2015053379 A1 | 4/2015 |

OTHER PUBLICATIONS

International search report dated Jul. 14, 2014 for PCT Application No. US 2014/026816.

International search report and written opinion dated Dec. 18, 2015 for PCT/US2015/051793.

Lehman, et al. Assessment of coronary plaque progression in coronary computed tomography angiography using a semiquantitative score. JACC Cardiovasc Imaging. Nov. 2009;2(11):1262-70. doi: 10.1016/j.jcmg.2009.07.007.

Notice of allowance dated Apr. 11, 2016 for U.S. Appl. No. 14/472,081.

Phan, et al. Effects of niacin on glucose levels, coronary stenosis progression, and clinical events in subjects with normal baseline glucose levels (<100 mg/dl): a combined analysis of the Familial Atherosclerosis Treatment Study (FATS), HDL-Atherosclerosis Treatment Study (HATS), Armed Forces Regression Study (AFREGS), and Carotid Plaque Composition by MRI during lipid-lowering (CPC) study. Am J Cardiol. Feb. 1, 2013;111(3):352-5. doi: 10.1016/j.amjcard.2012.09.034. Epub Nov. 17, 2012.

Remington's Pharmaceutical Sciences 18th Edition. 1990, Martin ed., Mack Publishing Co., PA, Title page and table of contents.

Saumet, et al. Non-invasive measurement of skin blood flow: comparison between plethysmography, laser-Doppler flowmeter and heat thermal clearance method. Int J Microcirc Clin Exp. 1986;5(1):73-83.

Seshasai, et al. Diabetes mellitus, fasting glucose, and risk of cause-specific death. N Engl J Med. Mar. 3, 2011;364(9):829-41. doi: 10.1056/NEJMoa1008862.

Agarwal. Cortisol metabolism and visceral obesity: role of 11beta-hydroxysteroid dehydrogenase type I enyzme and reduced co-factor NADPH. Endocr Res. Nov. 2003;29(4):411-8.

Alwine, et al. Method for detection of specific RNAs in agarose gels by transfer to diazobenzyloxymethyl-paper and hybridization with DNA probes. Proc Natl Acad Sci U S A. Dec. 1977;74(12):5350-4.

Amstad, et al. Mechanism of c-fos induction by active oxygen. Cancer Res. Jul. 15, 1992;52(14):3952-60.

Anthony, et al. Orally Administered Leucine Stimulates Protein Synthesis of Skeletal Muscle of Postabsorptive Rats in Association with Increased eIF4F Formation 1'2. The Journal of Nutrition. 2000; 130:139-145.

"Arend, et al. Inhibition of the production and effects of interleukin-1 and tumor necrosis factor alpha in rheumatoid arthritis. Arthritis Rheum. Feb. 1995;38(2):151-60".

Argiles, et al. Cross-talk between skeletal muscle and adipose tissue: a link with obesity? Med Res Rev. Jan. 2005;25(1):49-65.

Atabek, et al. Oxidative stress in childhood obesity. J Pediatr Endocrinol Metab. Aug. 2004;17(8):1063-8.

Ayala, et al. Chronic treatment with sildenafil improves energy balance and insulin action in high fat-fed conscious mice. Diabetes. Apr. 2007;56(4):1025-33. Epub Jan. 17, 2007.

Banakar, et al. 1alpha, 25-dihydroxyvitamin D3 prevents DNA damage and restores antioxidant enzymes in rat hepatocarcinogenesis induced by diethylnitrosamine and promoted by phenobarbital. World J Gastroenterol. May 1, 2004;10(9):1268-75.

Bannowsky, A. et al., Recovery of erectile function after nerve-sparing radical prostatectomy: improvement with nightly low-dose sildenafil. BJU Int., Feb. 18, 2008, vol. 101, No. 10, pp. 1279-1283.

"Bartges, et al. Calculating a patient's nutritional requirements. Veterinary Medicine. 2004; 99:632."

Bender, et al. Cyclic nucleotide phosphodiesterases: molecular regulation to clinical use. Pharmacol Rev. Sep. 2006;58(3):488-520.

Berchtold. A simple method for direct cloning and sequencing cDNA by the use of a single specific oligonucleotide and oligo(dT) in a polymerase chain reaction (PCR). Nucleic Acids Res. Jan. 11, 1989;17(1):453.

Beta-hydroxy Beta-methylbutyrate (HMB). 2009; 1-2. http://exrx.net/Nutrition/Supplements/HMB.html.

Black grape ingredients. Power of resveratrol. Accessed: Sep. 29, 2010. www.blackgrapehealth.com/Tnt37/ingredients.php.

(56) References Cited

OTHER PUBLICATIONS

Blum, et al. SIRT1 modulation as a novel approach to the treatment of disease of aging. J Med Chem. Jan. 27, 2011;54(2):417-32. Epub Nov. 16, 2010.
Bodybuilding, VitaMinder Power shaker, 2006, BodyBuilding.com, p. 1.
Bostrum, et al. A PGC1-α-dependent myokine that drives brown-fat-like development of white fat and thermogenesis. Nature. Jan. 11, 2012;481(7382):463-8. doi: 10.1038/nature10777.
Botanical Online 2010, 1-3. http://www.botanical-online.com/english/plantschemicalagents.htm.
Boustany. Diabetes and grapefruit. 2010. ThinkScienceNow. 1-4. http://www.thinksciencenow.com/blog-post/diabetes-and-grapefruit.
Brand, et al. Mitochondrial superoxide and aging: uncoupling-protein activity and superoxide production. Biochem Soc Symp. 2004;(71)203-13.
Breastfeeding.com Q&A How many ounces of breast milk should I pump? 2010; 1-2. http://www.breastfeeding.com/breastfeeding-questions/breastfeeding-pumping-basics/qa/how-many-ounces-of-breast-milk-should-i-pumpp.aspx.
"Brennan, et al. Inhibitory effect of TNF alpha antibodies on synovial cell interleukin-1 production in rheumatoid arthritis. Lancet. Jul. 29, 1989;2(8657):244-7."
Brookes. Mitochondrial H(+) leak and ROS generation: an odd couple. Free Radic Biol Med. Jan. 1, 2005;38(1):12-23.
Bruckbauer, et al. Synergistic effects of leucine and resveratrol on insulin sensitivity and fat metabolism in adipocytes and mice. Nutr Metab (Lond). Aug. 22, 2012;9(1):77. doi: 10.1186/1743-7075-9-77.
Bruckbauer, et al. Synergistic effects of metformin, resveratrol, and hydroxymethylbutyrate on insulin sensitivity. Diabetes Metab Syndr Obes. 2013;6:93-102. doi: 10.2147/DMSO.S40840. Epub Feb. 13, 2013.
Bruckbauer, et al. Synergistic effects of polyphenols and methylxanthines with leucine on AMPK/sirtuin-mediated metabolism in muscle cells and adipocytes. PLoS ONE. 9(2):e89166. Feb. 14, 2014.
Bruckbauer, et al. The effects of dairy components on energy partitioning and metabolic risk in mice: a microarray study. J Nutrigenet Nutrigenomics. 2009;2(2):64-77. Epub Mar. 4, 2009.
Busquets, et al. Interleukin-15 decreases proteolysis in skeletal muscle: a direct effect. Int J Mol Med. Sep. 2005;16(3):471-6.
Carbo, et al. Interleukin-15 antagonizes muscle protein waste in tumour-bearing rats. Br J Cancer. Aug. 2000;83(4):526-31.
Carbo, et al. Interleukin-15 mediates reciprocal regulation of adipose and muscle mass: a potential role in body weight control. Biochim Biophys Acta. Apr. 3, 2001;1526(1):17-24.
"Carroll, et al. Antagonism of the IL-6 cytokine subfamily—a potential strategy for more effective therapy in rheumatoid arthritis. Inflamm Res. Jan. 1998;47(1):1-7."
Cerutti, et al. The role of the cellular antioxidant defense in oxidant carcinogenesis. Environ Health Perspect. Dec. 1994;102 Suppl 10:123-9.
Chalasani, et al. The diagnosis and management of non-alcoholic fatty liver disease: Practice guideline by the American Association for the Study of Liver Diseases, American College of Gastroenterology, and the American Gastroenterological Association. Hepatology 2012; 55:2005-2021.
Chang, et al. Mammalian MAP kinase signalling cascades. Nature. Mar. 1, 2009;410(6824):37-40.
Cheng, et al. Leucine deprivation decreases fat mass by stimulation of lipolysis in white adipose tissue and upregulation of uncoupling protein 1 (UCP1) in brown adipose tissue. Diabetes. Jan. 2010;59(1):17-25. Epub Oct. 15, 2009.
Chung, et al. Contribution of polyol pathway to diabetes-induced oxidative stress. J Am Soc Nephrol. Aug. 2003;14(8 Suppl 3):S233-6.

Clement, et al. Weight loss regulates inflammation-related genes in white adipose tissue of obese subjects. FASEB J. Nov. 2004;18(14):1657-69.
Co-pending U.S. Appl. No. 15/447,049, filed Mar. 1, 2017.
Cottam, et al. The chronic inflammatory hypothesis for the morbidity associated with morbid obesity: implications and effects of weight loss. Obes Surg. May 2004;14(5):589-600.
De Souza, et al. Insulin secretory defect in zucker FA/FA rats is improved by ameliorating insulin resistance. Diabetes. Aug. 1995;44(8):984-91.
Ding, et al. Amino acid composition of lactating mothers' milk and confinement diet in rural North China. Asia Pac J. Clin Nutr. 2010; 19(3):344-349.
Doi, et al. Isoleucine, a Blood Glucose-Lowering Amino Acid, Increases Glucose Uptake in Rat Skeletal Muscle in the Absence of Increases in AMP-Activated Protein Kinase Activity. J Nutr. Sep. 2005;135(9):2103-8.
Donato, et al. Effects of leucine supplementation on the body composition and protein status of rats submitted to food restriction. Nutrition. May 2006;22(5):520-7.
Duval, et al. Increased reactive oxygen species production with antisense oligonucleotides directed against uncoupling protein 2 in murine endothelial cells. Biochem Cell Biol. 2002;80(6):757-64.
Erlanson-Albertsson. The role of uncoupling proteins in the regulation of metabolism. Acta Physiol Scand. Aug. 2003;178(4):405-12.
Ermak, et al. Calcium and oxidative stress: from cell signaling to cell death. Mol Immunol. Feb. 2002;38(10):713-21.
European search report and written opinion dated Mar. 9, 2015 for EP Application No. 12814141.3.
European search report and opinion dated May 6, 2016 for EP Application No. 13854549.
European search report and opinion dated Aug. 22, 2016 for EP Application No. 14770824.
"European search report and opinion dated Sep. 28, 2015 for EP Application No. 13758140.1."
Fain, et al. Comparison of the release of adipokines by adipose tissue, adipose tissue matrix, and adipocytes from visceral subcutaneous abdominal adipose tissues of obese humans. Endocrinology. May 2004;145(5):2273-82. Epub Jan. 15, 2004.
Feige, et al. Specific SIRT1 activation mimics low energy elevels and protects against diet-induced metabolic disorders by enhancing fat oxidation. Cell Metab. Nov. 2008;8(5):347-58. Erratum Cell Metab. Feb. 2009;9(2):210.
Festi, et al. Hepatic steastosis in obese patients: clinical aspects and prognostic significance. Obesity Rev 2004; 5:27-42.
Flatt, et al. Direct and indirect actions of nutrients in the regulation of insulin secretion from the pancreatic beta cells. Proc Nutr Soc. Dec. 1991;50(3):559-66.
Fortamet (Metaformin Hydrochloride) Extended-Release Tablets Label. http://www.accessdata.fda.gov/drugsatfda_docs/label/2008/021574s010lbl.pdf. Accessed Jul. 6, 2015.
Fraquelli, M. et al., Reproducibility of transient elastography in the evaluation of liver fibrosis in patients with chronic liver disease. Gut. Jan. 25, 2007, vol. 56; pp. 968-973; Abstract; pp. 969 1st column, 2nd paragraph; DOI 10.1136/gut.2006.111302.
Fried, et al. Omental and subcutaneous adipose tissues of obese subjects release interleukin-6: depot difference and regulation by glucocorticoid. J Clin Endocrinol Metab. Mar. 1998;83(3):847-50.
Fu, L., et al., Interaction between leucine and phosphodiesterase 5 inhibition in modulating insulin sensitivity and lipid metabolism. Diabetes, Metabolic syndrome and obesity:Targets and therapy. May 6, 2015; vol. 8: pp. 227-239.; abstract; p. 228, 1st column, 3rd paragraph to 2nd column, 1st paragraph.
Furukawa, et al. Increased oxidative stress in obesity and its impoact on metabolic syndrome. J Clin Invest. Dec. 2004;114(12):1752-61.
Gerlinger-Romero, et al. Chronic supplementation of beta-hydroxy-beta methylbutyrate (HMβ) increases the activity of the GH/IGF-I axis and induces hyperinsulinemia in rats. Growth Horm IGF Res. Apr. 2011;21(2):57-62. doi: 10.1016/j.ghir.2010.12.006. Epub Jan. 14, 2011.
Giri, et al. Constitutive activation of NF-kappaB causes resistance to apoptosis in human cutaneous T cell lymphoma HuT-78 cells.

(56) References Cited

OTHER PUBLICATIONS

Autocrine role of tumor necrosis factor and reactive oxygen intermediates. J Biol Chem. May 29, 1998;273(22):14008-14.

Goldman, et al. Generation of reactive oxygen species in a human keratinocyte cell line: role of calcium. Arch Biochem Biophys. Feb. 1, 1998;350(1):10-8.

Goldstein, et al. Adiponectin: A novel adipokine linking adipocytes and vascular function. J Clin Endocrinol Metab. Jun. 2004;89(6):2563-8.

Gordeeva, et al. Cross-talk between reactive oxygen species and calcium in living cells. Biochemistry (Mosc). Oct. 2003;68(10):1077-80.

Hale, et al. Transfer of metforimin into human milk. Diabetologia. 2002; 45:1509-1514.

Harwood, et al. Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals. The Journal of Biological Chemistry. Sep. 26, 2003; 278(39):37099-37111.

"Haworth, et al. Expression of granulocyte-macrophage colony-stimulating factor in rheumatoid arthritis: regulation by tumor necrosis factor-alpha. Eur J Immunol. Oct. 1991;21(10):2575-9."

Hollander, et al. Induction of fos RNA by DNA-damaging agents. Cancer Res. Apr. 1, 1989;49(7):1687-92.

"Hornstra, et al. Essential fatty acids in pregnancy and early human development. Eur J Obstet Gynecol Reprod Biol. Jul. 1995;61(1):57-62."

Hotamisligil, et al. Tumor necrosis factor alpha inhibits signaling from the insulin receptor. Proc Natl Acad Sci U S A. May 24, 1994;91(11):4854-8.

Hou, et al. Sirt1 regulates hepatocyte lipid metabolism through activating AMPK-activated protein kinase. J Biol Chem 2008; 383:20015-20026.

Howells, et al. Phase I randomized, double-blind pilot study of micronized resveratrol (SRT501) in patients with hepatic metastases—safety, pharmacokinetics, and pharmacodynamics. Cancer Prev Res (Phila). Sep. 2011;4(9):1419-25. Epub Jun. 16, 2011.

Howitz, K.T. et al., Small molecule activators of sirtuins extend *Saccharomyces cerevisiae* lifespan. Letters to Nature. 2003; 425:191-196.

Hydroxymethyl Butyrate (HMB). Beth Israel Deaconess Medical Center. Accessed Dec. 13, 2012. http://www.bidmc.org/YourHealth/HolisticHealth/HerbsandSupplements.aspx?ChunkID=21551.

Inoguchi, et al. High glucose level and free fatty acid stimulate reactive oxygen species production through protein kinase C-dependent activation of NAD(P)H oxidase in cultured vascular cells. Diabetes. Nov. 2000;49(11):1939-45.

International search report and written opinion dated May 28, 2013 for PCT Application No. US2013/030044.

International search report and written opinion dated Feb. 8, 2007 for PCT Application No. US2006/038854.

International search report and written opinion dated Mar. 10, 2014 for PCT Application No. US2013/069957.

International search report and written opinion dated May 22, 2015 for PCT/US2015/018182.

International search report and written opinion dated Jul. 21, 2014 for PCT/US2014/016592.

International Search report and Written opinion dated Sep. 19, 2016 for Singapore Application No. 11201503774P.

International search report and written opinion dated Nov. 29, 2012 for PCT Application No. US2012/046814.

International Search Report dated Nov. 28, 2016 for International Application No. PCT/US2016/049272.

"Ionut, et al. Novel canine models of obese prediabetes and mild type 2 diabetes. Am J Physiol Endocrinol Metab. Jan. 2010;298(1):E38-48. doi: 10.1152/ajpendo.00466.2009. Epub Oct. 20, 2009."

JillWillRun. Hydration Review Nuun, 2009, pp. 1-8.

Khan, et al. Induction of renal oxidative stress and cell proliferation response by ferric nitrilotriacetate (Fe-NTA): diminution by soy isoflavones. Chem Biol Interact. Aug. 10, 2004;149(1):23-35.

Kiens, Skeletal Muscle Lipid Metabolism in Exercise and Insulin Resistance. Physiological Reviews. 2006;86: 205-243.

Koren, et al. Vitamin D is a prooxidant in breast cancer cells. Cancer Res. Feb. 15, 2001;61(4):1439-44.

Korshunov, et al. High protonic potential actuates a mechanism of production of reactive oxygen species in mitochondria. FEBS Lett. Oct. 13, 1997;416(1):15-8.

Kouzarides, et al. Leucine zippers of fos, jun and GCN4 dictate dimerization specificity and thereby control DNA binding. Nature. Aug. 17, 1989;340(6234):568-71.

Krishnaswamy, et al. Effect of vitamin B6 on leucine-induced changes in human subjects. Am J Clin Nutr. Feb. 1976;29(2):177-81.

"LaFlamme. Development and validation of a body condition score system for dogs. Canine Practice. 1997; 22:10-15."

Layman. The role of leucine in weight loss diets and glucose homeostasis. Journal of Nutrition, 2003, 133, 261S-267S.

Lee, et al. The evolving role of inflammation in obesity and the metabolic syndrome. Curr Diab Rep. Feb. 2005;5(1):70-5.

Leenders, et al. Leucine as a pharmaconutrient to prevent and treat sarcopenia and type 2 diabetes. Nutr Rev. Nov. 2011;69(11):675-89. doi: 10.1111/j.1753-4887.2011.00443.x. Abstract only.

Li, et al. Evaluation of antioxidant capacity and aroma quality of breast milk. Nutrition. 2008;25(1):1-3.

Li, et al. Leucine nutrition in animals and humans: mTOR signaling and beyond. Amino Acids. Nov. 2011;41(5):1185-93. Epub Jul. 20, 2011.

Li, et al. Visceral fat: higher responsiveness of fat mass and gene expression to calorie restriction than subcutaneous fat. Exp Biol Med (Maywood) Nov. 2003;228(10):1118-23.

"Lim, et al. Intakes of dietary docosahexaenoic acid ethyl ester and egg phosphatidylcholine improve maze-learning ability in young and old mice. J Nutr. Jun. 2000;130(6):1629-32."

Lin, et al. Increased oxidative damage with altered antioxidative status in type 2 diabetic patients harboring the 16189 T to C variant of mitochondrial DNA. Ann N Y Acad Sci. May 2005;1042:64-9.

Lin. Suppression of protein kinase C and nuclear oncogene expression as possible action mechanisms of cancer chemoprevention by Curcumin. Arch Pharm Res. Jul. 2004;27(7):683-92.

Lind, et al. Evaluation of four different methods to measure endothelium-dependent vasodilation in the human peripheral circulation. Clin Sci (Lond). May 2002;102(5):561-7.

Lira, et al. Nitric oxide and AMPK cooperatively regulate PGC-1 in skeletal muscle cells. J Physiol. Sep. 15, 2010;588(Pt 18):3551-66. Epub Jul. 19, 2010.

Lumeng, et al. Plasma content of B6 vitamers and its relationship to hepatic vitamin B6 metabolism. J Clin Invest. Oct. 1980; 66(4): 688-695.

Lynch, et al. Leucine is a direct-acting nutrient signall that regulates protein synthesis in adipose tissue. Am J Physiol Endocrinol Metab. Sep. 2002;283(3):E503-13.

Macotela, et al. Dietary Leucine—an environmental modifier of insulin resistance acting on multiple levels of metabolism. PLoS One. 2011;6(6):e21187. Epub Jun. 22, 2011.

Mahadev, et al. The NAD(P)H oxidase homolog Nox4 modulates insulin-stimulated generation of H2O2 and plays an integral role in insulin signal transduction. Mol Cell Biol. Mar. 2004;24(5):1844-54.

Manders, et al. Co-ingestion of a protein hydrolysate with or without additional leucine effectively reduces postprandial blood glucose excursions in type 2 diabetic men 1. May 2006. 1294-1299. http://jn.nutrition.org/content/136/5/1294.full.pdf.

Manea, et al. Changes in oxidative balance in rat pericytes exposed to diabetic conditions. J Cell Mol Med. Jan.-Mar. 2004;8(1):117-26.

"Mawby, et al. Comparison of various methods for estimating body fat in dogs. J Am Anim Hosp Assoc. Mar.-Apr. 2004;40(2):109-14."

Melnik. Leucine signaling in the pathogenesis of type 2 diabetes and obesity. World J Diabetes. Mar. 15, 2012;3(3):38-53. doi: 10.4239/wjd.v3.i3.38.

(56) References Cited

OTHER PUBLICATIONS

Melton, et al. Efficient in vitro synthesis of biologically active RNA and RNA hybridization probes from plasmids containing a bacteriophage SP6 promoter. Nucleic Acids Res. Sep. 25, 1984;12(18):7035-56.

Merck Manual Home Edition online article entititled, "Multiple Sclerosis"—accessed Jun. 20, 2010 at http://www.merck.com/mmhe/print/sec06/ch092/ch092b.html.

Merck Manual Home Edition online article entitled, "Introduction: Coronary Artery Disease"—accessed Jun. 20, 2010 at www.merck.com/mmhe/print/sec03/ch033/ch033a.html.

Miwa, et al. Mitochondrial matrix reactive oxygen species production is very sensitive to mild uncoupling. Biochem Soc Trans. Dec. 2003;31(Pt 6):1300-1.

Morris, et al. 1,25-dihydroxyvitamin D3 modulation of adipocyte glucocorticoid function. Obes Res. Apr. 2005;13(4):670-7.

"Moser, et al. Interleukin 1 and tumor necrosis factor stimulate human vascular endothelial cells to promote transendothelial neutrophil passage. J Clin Invest. Feb. 1989;83(2):444-55."

Nagao, et al.Dietary diacylglycerol suppresses accumulation of body fat compared to triacylglycerol in men in a double-blind controlled trial. J Nutr. Apr. 2000;130(4):792-7.

Nairizi, et al. Leucine supplementation of drinking water does not alter susceuptibility to diet-induced obesity in mice. Nutr. Apr. 2009;139(4):719-9. Epub Feb. 25, 2009.

Nisoli, et al. Mitochondrial biogenesis by NO yields functionally active mitochondria in mammals. Proc Natl Acad Sci U S A. Nov. 23, 2004;101(47):16507-12. Epub Nov. 15, 2004.

Nisoli, et al. Mitochondrial biogenesis in mammals: the role of endogenous nitric oxide. Science. Feb. 7, 2003;299(5608):896-9.

Nomura, et al. Inhibition of 12-O-tetradecanoylphorbol-13-acetate-induced NF-kappaB activation by tea polyphenols, (−)-epigallocatechin gallate and theaflavins. Carcinogenesis. Oct. 2000;21(10):1885-90.

Notice of allowance dated Feb. 1, 2016 for U.S. Appl. No. 14/927,255.

Notice of allowance dated Feb. 27, 2017 for U.S. Appl. No. 15/164,647.

Notice of allowance dated Mar. 6, 2015 for U.S. Appl. No. 13/866,936.

Notice of allowance dated Mar. 15, 2013 for U.S. Appl. No. 13/549,381.

Notice of allowance dated Apr. 11, 2016 for U.S. Appl. No. 14/927,228.

Notice of allowance dated Apr. 25, 2013 for U.S. Appl. No. 11/542,703.

Notice of allowance dated Apr. 29, 2015 for U.S. Appl. No. 13/866,936.

Notice of allowance dated May 29, 2013 for U.S. Appl. No. 13/549,399.

Notice of allowance dated Aug. 13, 2013 for U.S. Appl. No. 13/549,381.

Notice of allowance dated Aug. 15, 2013 for U.S. Appl. No. 13/549,399.

"Notice of allowance dated Sep. 1, 2015 for U.S. Appl. No. 13/662,345."

"Notice of allowance dated Sep. 11, 2015 for U.S. Appl. No. 14/746,516."

Notice of Allowance dated Oct. 26, 2016 for U.S. Appl. No. 14/772,366.

Notice of allowance dated Dec. 28, 2012 for U.S. Appl. No. 13/549,399.

Ofei, et al. Effects of an engineered human anti-TNF-alpha antibody (CDP571) on insulin sensitivity and glycemic control in patients with NIDDM. Diabetes. Jul. 1996;45(7):881-5.

Office action dated Feb. 5, 2015 for U.S. Appl. No. 13/662,345.

Office action dated Apr. 22, 2013 for U.S. Appl. No. 13/662,345.

Office action dated Jun. 25, 2010 for U.S. Appl. No. 11/543,171.

Office action dated Jul. 15, 2010 for U.S. Appl. No. 11/542,703.

Office action dated Sep. 16, 2013 for U.S. Appl. No. 13/662,345.

Office action dated Nov. 7, 2012 for U.S. Appl. No. 13/549,381.

Office Action dated Dec. 15, 2016 for U.S. Appl. No. 14/770,418.

Office action dated Dec. 23, 2010 for U.S. Appl. No. 11/542,703.

Office action dated Dec. 23, 2010 for U.S. Appl. No. 11/543,171.

OpenSource Diets. Product Data D12451. Report Repeat Revise Where NutriPhenomics Begins Research Diets, Inc. 20. Last modified: Feb. 28, 2013.

Panichi, et al. Calcitriol modulates in vivo and in vitro cytokine production: a role for intracellular calcium. Kidney Int. Nov. 1998;54(5):1463-9.

Park, et al. Resveratrol ameliorates aging-related metabolic phenotypes by inhibiting cAMP phosphodiesterases. Cell. Feb 3, 2012;148(3):421-33.

Zhang, et al. Increasing dietary leucine intake reduces diet-induced obesity and improves glucose and cholesterol metabolism in mice via multimechanisms. Diabetes. Jun. 2007;56(6):1647-54. Epub Mar. 14, 2007.

Patterson, et al. Excretion of tryptophan-niacin metabolites by young men: effects of tryptophan, leucine, and vitamin B6 intakes. Am J Clin Nutr. Oct. 1980;33(10):2157-67.

Pearce, et al. Sports supplements: A modern case of caveat emptor. Current Sports Medicine Reports. 2005; 4:171-178.

Peterson, et al. The mechanism of transamination. Function of the histidyl residue at the active site of supernatant aspartate transaminase. J Biol Chem. Feb. 25, 1970;245(4):806-13.

Povolny, et al. The role of recombinant human M-CSF, IL-3, GM-CSF and calcitriol in clonal development of osteoclast precursors in primate bone marrow. Exp Hematol. Apr. 1993;21(4):532-7.

Price, et al. SIRT1 is required for AMPK activation and the beneficial effects of resveratrol on mitochondrial function. Cell Metab. May 2, 2012;15(5):675-90. doi: 10.1016/j.cmet.2012.04.003.

Purushotham, et al. Hepatocyte-specific deletion of Sirt1 alters fatty acid metabolism and results in hepatic steatosis and inflammation. Cell Metabolism 2009; 9:327-338.

Quinn, et al. Interleukin-15 stimulates adiponectin secretion by 3T3-L1 adipocytes: evidence for a skeletal muscle-to-fat signaling pathway. Cell Biol Int. Jun. 2005;29(6):449-57.

Rasmussen, et al. Regulation of fatty acid oxidation in skeletal muscle. Annu Rev Nutr. 1999;19:463-84.

Reeves. Components of the AIN-93 diets as improvements in the AIN-76A diet. J Nutr. May 1997;127(5 Suppl):838S-841S.

Roberts, et al. Nutrition and aging: changes in the regulation of energy metabolism with aging. Physiol Rev. Apr. 2006;86(2):651-67.

"Rogers. A healthy body, a healthy mind: long-term impact of diet on mood and cognitive function. Proc Nutr Soc. Feb. 2001;60(1):135-43."

S Bear. Nother way to get leucine for the 6 week cure, 2009, pp. 1-5.

Sabatini, et al. Tadalafil alters energy metabolism in C2C12 skeletal muscle cells. Acta Biochim Pol. 2011;58(2):237-41. Epub Jun. 16, 2011.

Schulze-Osthoff, et al. Oxidative stress and signal transduction. Int J Vitam Nutr Res. 1997;67(5):336-42.

Sellden, et al. Augmented thermic effect of amino acids under general anaesthesia: a mechanism useful for prevention of anaesthesia-induced hypothermia. Clin Sci (Lond). May 1994;86(5):611-8.

Shalwala, M. B., A novel role of sirt1 in sildenafil induced cardioprotection in mice. Virginia Commonwealth University—Master Thesis, May 2010, pp. 1-56.

Shangari, et al. The cytotoxic mechanism of glyoxal involves oxidative stress. Biochem Pharmacol. Oct. 1, 2004;68(7):1433-42.

Shi, et al. 1alpha,25-dihydroxyvitamin D3 inhibits uncoupling protein 2 expression in human adipocytes. FASEB J. Nov. 2002;16(13):1808-10. Epub Sep. 5, 2002.

Shi, et al. 1alpha,25-Dihydroxyvitamin D3 modulates human adipocyte metabolism via nongenomic action. FASEB J. Dec. 2001;15(14):2751-3. Epub Oct. 15, 2001.

Simeone, et al. How retinoids regulate breast cancer cell proliferation and apoptosis. Cell Mol Life Sci. Jun. 2004;61(12):1475-84.

(56) References Cited

OTHER PUBLICATIONS

Soares, et al. Effects of oxidative stress on adiponectin secretion and lactate production in 3T3-L1 adipocytes. Free Radic Biol Med. Apr. 1, 2005;38(7):882-9.
Solerte, et al. Metabolic effects of orally administered amino acid mixture in elderly subjects with poorly controlled type 2 diabetes mellitus. Am J Cardiol. Apr. 22, 2004;93(8A):23A-29A.
Song, et al. Methionine-induced hyperhomocysteinemia promotes superoxide anion generation and NFkappaB activation in peritoneal macrophages of C57BL/6 mice. J Med Food. 2004 Summer;7(2):229-34.
Sonta, et al. Evidence for contribution of vascular NAD(P)H oxidase to increased oxidative stress in animal models of diabetes and obesity. Free Radic Biol Med. Jul. 1, 2004;37(1):115-23.
Sorescu, et al. Superoxide production and expression of nox family proteins in human atherosclerosis. Circulation. Mar. 26, 2002;105(12):1429-35.
Stipanuk. Leucine and protein synthesis; mTOR and beyond. Nutr Rev. Mar. 2007;65(3):122-9.
Sun, et al. 1, 25(OH)2D3 and reactive oxygen species interatively stimulate angiotensinogen expression in differentiated 3T3-L1 adipocytes. FASEB J. 2005; 19:A70, No. 67.8 (abstract only).
Sun, et al. Calcium and dairy products inhibit weight and fat regain during ad libitum consumption following energy restriction in Ap2-agouti transgenic mice. J Nutr. Nov. 2004;134(11):3054-60.
Sun, et al. Dietary calcium regulates ROS production in aP2-agouti transgenic mice on high-fat/high-sucrose diets. Int J Obes (Lond). Sep. 2006;30(9):1341-6. Epub Mar. 7, 2006.
Sun, et al. Dual effects of 1-alpha,25-(OH)2-D3 on adipocyte apoptosis. FASEB J. 2004; 18:A49 (abstract only).
Sun, et al. Effects of mitochondrial uncoupling on adipocyte intracellular Ca(2+) and lipid metabolism. J Nutr Biochem. Apr. 2003;14(4):219-26.
Sun, et al. Leucine and calcium regulate fat metabolism and energy partitioning in murine adipocytes and muscle cells. Lipids. Apr. 2007;42(4):297-305. Epub Feb. 20, 2007.
Sun, et al. Leucine modulation of mitochondrial mass and oxygen consumption in skeletal muscle cells and adipocytes. Nutr Metab (Lond). Jun. 5, 2009;6:26. doi:10.1186/1743-7075-6-26.
Sun, et al. Reactive oxygen species stimulate cell proliferation and down-regulate UCP2 expression in 3T3-L1 adipocytes. Obesity Research. 2004; 11: A21, No. 80-OR (abstract only).
Sun, et al. Role of uncoupling protein 2 (UCP2) expression and 1alpha, 25-dihydroxyvitamin D3 in modulating adipocyte apoptosis. FASEB J. Sep. 2004;18(12)1430-2. Epub Jul. 1, 2004.
Suzuki, et al. Oxidants as stimulators of signal transduction. Free Radic Biol Med. 1997;22(1-2):269-85.
Suzuki, et al. Relationship between obesity and serum markers of oxidative stress and inflammation in Japanese. Asian Pac J Cancer Prev. Jul.-Sep. 2003;4(3):259-66.
Tappy, et al. Thermic effect of infused amino acids in healthy humans and in subjects with insulin resistance. Am J Clin Nutr. Jun. 1993;57(6):912-6.
Tennen, et al. Finding a target for resveratrol. Cell. Feb. 3, 2012;148(3):387-9.
Thannickal, et al. Reactive oxygen species in cell signaling. Am J Physiol Lung Cell Mol Physiol. Dec. 2000;279(6):L1005-28.
Thompson, et al. Effect of energy-reduced diets high in dairy products and fiber on weight loss in obese adults. Obes Res. Aug. 2005;13(8):1344-53.
Thompson, et al. Effects of nine weeks of beta-hydroxy-beta-methylbutyrate supplementation on strength and body composition in resistance trained men. Journal of strength and conditioning research / National Strength & Conditioning Association 23: 827-835, 2009.
"Sunvold, et al. Dietary fiber for dogs: IV. In vitro fermentation of selected fiber sources by dog fecal inoculum and in vivo digestion and metabolism of fiber-supplemented diets. J Anim Sci. Apr. 1995;73(4):1099-109."

Upham, et al. Hydrogen peroxide inhibits gap junctional intercellular communication in glutathione sufficient but not glutathione deficient cells. Carcinogenesis. Jan. 1997;18(1):37-42.
Zhang, et al. Occurrence of beta-hydroxyl-beta-methyl butyrates in foods and feed. Protein and amini acid nutrition. 1994; A464: 2685-2690.
Zoraghi, et al. Phosphodiesterase-5 Gln817 is critical for cGMP, vardenafil, or sildenafil affinity: its orientation impacts cGMP but not cAMP affinity. J Biol Chem. Mar. 3, 2006;281(9):5553-8. Epub Jan. 5, 2006.
Valle, et al. Low-grade systemic inflammation, hypoadiponectinemia and a high concentration of leptin are present in very young obese children, and correlate with metabolic syndrome. Diabetes Metab. Feb. 2005;31(1):55-62.
Van Loon. Leucine as a pharmaconutrient in health and disease. Curr Opin Clin Nutr Metab Care. Jan. 2012;15(1):71-7. Abstract only.
Varma, et al. Chronic Tadalafil Therapy Improves Fasting Glucose Levels and Downregulates Microrna-103 and -107 in Obese Diabetic Mice. Circulation2012; 126: A14802. Abstract 14802.
Verdin, et al. Sirtuin regulation of mitochondria: energy production, apoptosis, and signaling. Trends Biochem Sci. Dec. 2010;35(12):669-75. Epub Sep. 20, 2010.
Vernon et al. Systematic review: The epidemiology and natural history of non-alcoholic fatty liver disease and non-alcoholic steatohepatitis in adults. Aliment Pharmacol 2011; 34:274-285.
Volk, et al. Transient Ca2+ changes in endothelial cells induced by low doses of reactive oxygen species: role of hydrogen peroxide. Mol Cell Biochem. Jun. 1997;171(1-2):11-21.
Wajchenberg. Subcutaneous and visceral adipose tissue: their relation to the metabolic syndrome. Endocr Rev. Dec. 2000;21(6):697-738.
Warner. Metformin Linked to B12 Deficiency, 2009, WebMD, pp. 1-2.
Weisberg, et al. Obesity is associated with macrophage accumulation in adipose tissue. J Clin Invest. Dec. 2003;112(12):1796-808.
Weitzman, et al. Free radical adducts induce alterations in DNA cytosine methylation. Proc Natl Acad Sci U S A. Feb. 15, 1994;91(4):1261-4.
Wilson, et al. Effects of beta-hydroxy-beta-methylbutyrate (HMB) on exercise performance and body composition across varying levels of age, sex, and training experience: A review. Nutr Metab (Lond). Jan. 2008;5:1.
Wiseman, et al. Damage to DNA by reactive oxygen and nitrogen species: role in inflammatory disease and progression to cancer. Biochem J. Jan. 1, 1996;313 ( Pt 1):17-29.
Xiao, et al. Leucine deprivation increases hepatic insulin sensitivity via GCN2/mTOR/S6K1 and AMPK pathways. Diabetes. Mar. 2011;60(3):746-56. Epub Jan. 31, 2011.
Xu, et al. Chronic inflammation in fat plays a crucial role in the development of obesity-related insulin resistance. J Clin Invest. Dec. 2003;112(12):1821-30.
Xue, et al. Relationship between human adipose tissue agouti and fatty acid synthase (FAS). J Nutr. Oct. 2000;130(10):2478-81.
Xue, et al. The agouti gene product inhibits lipolysis in human adipocytes via a Ca2+-dependent mechanism. FASEB J. Oct. 1998;12(13):1391-6.
Yalkowsky, et al. Potentiometric titration of monomeric and micellar acylcarnitines. J Pharm Sci. Jun. 1970;59(6):798-802.
Yalkowsky, et al. Some micellar properties of long-chain acylcarnitines. J Colloid Interface Sci. Dec. 1970;34(4):525-33.
"Yamka, et al. In vivo measurement of flatulence and nutrient digestibility in dogs fed poultry by-product meal, conventional soybean meal, and low-oligosaccharide low-phytate soybean meal. Am J Vet Res. Jan. 2006;67(1):88-94."
Yang, et al. Leucine metabolism in regulation of insulin secretion from pancreatic beta cells. Nutr Rev. May 2010;68(5):270-9.
"Yudkin, et al. Inflammation, obesity, stress and coronary heart disease: is interleukin-6 the link? Atherosclerosis. Feb. 2000;148(2):209-14."
Zanchi, et al. Potential antiproteolytic effects of L-leucine: observations of in vitro and in vivo studies. Nutr Metab (Lond). Jul. 17, 2008;5:20.

(56) References Cited

OTHER PUBLICATIONS

Zemel. Calcium and dairy modulation of obesity risk. Obes Res. Jan. 2005;13(1):192-3.

Zemel, et al. Calcium and dairy acceleration of weight and fat loss during energy restriction in obese adults. Obes Res. Apr. 2004;12(4):582-90.

Zemel, et al. Dairy augmentation of total and central fat loss in obese subjects. Int J Obes (Lond). Apr. 2005;29(4):391-7.

Zemel, et al. Effects of dairy compared with soy on oxidative and inflammatory stress in overweight and obese subjects. Am J Clin Nutr. Jan. 2010;91(1):16-22. Epub Nov. 4, 2009.

Zemel, et al. Regulation of adiposity by dietary calcium. FASEB J. Jun. 2000;14(9):1132-8.

Zemel. Role of calcium and dairy products in energy partitioning and weight management. Am J Clin Nutr. May 2004;79(5):907S-912S.

Zemel. The role of dairy foods in weight management. J Am Coll Nutr. Dec. 2005;24(6 Suppl):537S-46S.

Zemel, et al. Effects of calcium and dairy on body composition and weight loss in African-American adults. Obes Res. Jul. 2005;13(7):1218-25.

Anonymous: "European commission health and consumer protection directorate—general directorate C—scientific opinions c2—management of scientific committees II; scientificco-operation and networks opinion of the scientific committee on food on the tolerable upper intake levels of nicotinic acid and nicotinamide," May 6, 2002.Available at: http://ec.europa.eu/foods/fs/sc/scf/out80j_en.pdf. Retrieved on Sep. 21, 2016.

Anonymous: "GRAS notification for L-Leucine produced by innonio limited,"May 27, 2014, Available at: http://www.fda.gov/ucm/groups/fdagov-public/@fdaov-foods-gen/documents/document/ucm407679.pdf. Retrieved on Sep. 21, 2016.

European Search Report dated Sep. 30, 2016 for European Application No. 14768984.8.

Kies, E. et al., Interrelationship of leucine with lysine, tryophan, and niacin as they influence protein value of cereal gains for humans. Cereal Chemistry. Apr. 1972; 223-231.

Nakagawa, I. Effect of an excess intake of leucine, with and without additions of vitamin B6 and/or niacin, on tryptophan and niacin metabolism in rats. Journal of nutritional science and vitaminology. 23(6) Jan. 1, 1977. p. 535-548.

Truswell, A.S. Effect of surplus leucine intake on serum cholesterol in man. Proceedings of the nutrition society. 23(2). Sep. 1, 1964. pp. XLVI-XLVII.

Zhang, Y. Increasing dietary leucine intake reduces diet-induced obesity and improves glucose and cholesterol metabolism in mice via multimechanisms. Diabetes, 56(6); Mar. 27, 2007. pp. 1647-1654.

Nicotinic Acid          Nicotinamide Riboside

Aortic Plaque Lipid

Control

Leucine

Leucine+50mg Nicotinic Acid

1000mg Nicotinic Acid

Aortic Macrophage Infiltration

COMPOSITIONS, METHODS AND KITS FOR REDUCING LIPID LEVELS

CROSS REFERENCE

This application is a continuation application of U.S. application Ser. No. 14/472,081, filed Aug. 28, 2014, which is a continuation-in-part application of International Application No. PCT/US2014/026816, filed on Mar. 13, 2014, which claims priority to U.S. Provisional Patent Application No. 61/800,363, filed on Mar. 15, 2013, the content of each of which is hereby incorporated by reference in their entirety.

BACKGROUND OF THE INVENTION

Metabolic disorders, such as hyperlipidemia and obesity, and the related impact on health and mortality presents a significant burden to public health. For instance, obesity, clinically defined as a body mass index of over 30 kg/m2, is estimated to affect 35.7% of the U.S. adult population. In the U.S., obesity is estimated to cause roughly 110,000-365,000 deaths per year. Obesity can result in hyperlipidemia, characterized by an excess of lipids, including cholesterol, cholesterol esters, phospholipids, and triglycerides, in the bloodstream, and can further result in diabetes, vascular disease, cancer, renal disease, infectious diseases, external causes, intentional self-harm, nervous system disorders, and chronic pulmonary disease (N Engl J Med 2011; 364:829-841). Metabolic syndrome, in which subjects present with central obesity and at least two other metabolic disorders (such as high cholesterol, high blood pressure, or diabetes), is estimated to affect 25% of the U.S. population.

Hyperlipidemia, one of the symptoms of obesity and other conditions, can be treated with various medications, including nicotinic acid. Nicotinic acid is a form of vitamin B3 (niacin). When taken in high doses (1-3 g/day), nicotinic acid can treat hyperlipidemia, as it can lower total lipid, LDL, cholesterol, triglycerides, and lipoprotein, or raise HDL lipoprotein in the bloodstream. It can also reduce atherosclerotic plaque progression and coronary heart disease morbidity and mortality.

However, nicotinic acid can have a significant side-effect and hence can be generally poorly tolerated. One significant side-effect can be severe cutaneous vasodilation and flushing responses, and is consequently infrequently prescribed despite well documented safety and efficacy (Carlson L A. Nicotinic acid: the broad-spectrum lipid drug. A 50th anniversary review. J Int Med 2005; 258:94-114). While side effects are somewhat attenuated in sustained (SR) and extended (ER) release preparations, the side effects persist sufficiently to limit drug use. Therefore, there exists a pressing need to decrease the side-effects of the nicotinic acid without decreasing its therapeutic effects.

SUMMARY OF THE INVENTION

The subject application provides compositions, methods, and kits for treating hyperlipidemia in a subject. The compositions, methods, and kits can include leucine and/or leucine metabolites in combination with nicotinic acid. The present invention addresses the negative side effects of treating subjects with high doses of nicotinic acid.

The subject compositions can be administered orally or through other routes such as intravenous administration. Compositions for oral administration can include pills, tablets, capsules, and the like.

In one aspect, the current invention provides compositions comprising at least about 250 mg of leucine and/or about 25 mg of one or more leucine metabolites; and at least about 1 mg of nicotinic acid and/or nicotinamide riboside and/or one or more nicotinic acid metabolites.

In another aspect of the invention, compositions are provided that comprise at least about 250 mg of leucine and/or about 25 mg of one or more leucine metabolites; and an amount of nicotinic acid and/or nicotinamide riboside and/or one or more nicotinic acid metabolites, wherein the composition is substantially free of each of alanine, glycine, glutamic acid, and proline.

In yet another aspect, the current invention also provides compositions comprising at least about 250 mg of leucine and/or about 25 mg of one or more leucine metabolites; and an amount of nicotinic acid and/or nicotinamide riboside and/or nicotinic acid metabolites, wherein the amount of nicotinic acid and/or nicotinic acid metabolites is insufficient to reduce lipid content in the absence of component (a).

In still yet another aspect of the invention, compositions are provided that comprise an amount of leucine and/or one or more leucine metabolites; and an amount of nicotinic acid and/or nicotinamide riboside and/or one or more nicotinic acid metabolites, wherein the composition is administered to a subject in need thereof, further wherein the composition causes a reduced degree of cutaneous vasodilation in the subject administered as compared to a dose of nicotinic acid alone that has the same effectiveness as the composition in lowering lipid content in the subject.

In another aspect, current invention further provides compositions comprising leucine and/or one or more leucine metabolites; and at least about 1 mg of nicotinic acid and/or nicotinamide riboside and/or one or more nicotinic acid metabolites, wherein the molar ratio of component (a) to (b) in said composition is greater than about 20.

In some embodiments, the composition described herein comprises at least about 500 mg of leucine and/or at least about 200 mg of the one or more leucine metabolites. In some embodiments, the composition can comprise at least about 250 mg of leucine and/or about 25 mg of one or more leucine metabolites. In some embodiments, the amount of leucine and/or one or more leucine metabolites is less than about 1 g. In some embodiments, the amount of leucine and/or one or more leucine metabolites is less than 3 g.

The compositions as disclosed herein can be substantially free of nicotinamide. In some embodiments, the composition can be substantially free of nicotinic acid metabolites. In another embodiment, the composition can be substantially free of each of nicotinyl CoA, nicotinuric acid, nicotinate mononucleotide, nicotinate adenine dinucleotide, and nicotinamide adenine dinucleotide. In some embodiments, the nicotinic acid and/or nicotinamide riboside and/or one or more nicotinic acid metabolites is nicotinic acid.

The composition as disclosed herein can be substantially free of leucine metabolites. In some embodiments, the leucine and/or one or more leucine metabolites is leucine.

In some cases, the compositions described herein can include an amount of nicotinic acid and/or nicotinamide riboside and/or one or more nicotinic acid metabolites that can be less than about 1 g. In some cases, the amount of nicotinic acid and/or nicotinamide riboside and/or one or more nicotinic acid metabolites can be less than about 250 mg. In some embodiments, the amount of nicotinic acid and/or nicotinamide riboside and/or one or more nicotinic acid metabolites can be between about 1-100 mg. In still some embodiments, the amount of nicotinic acid and/or nicotinamide riboside and/or one or more nicotinic acid metabolites can be at least about 1 mg.

In some embodiments, the composition described herein can include an amount of nicotinic acid and/or nicotinamide riboside and/or one or more nicotinic acid metabolites that is capable of achieving a serum level of the nicotinic acid and/or nicotinamide riboside and/or one or more nicotinic acid metabolites that is less than about 100 nM. In another aspect of the invention, the amount of nicotinic acid and/or nicotinamide riboside and/or one or more nicotinic acid metabolites can be capable of achieving a serum level of the nicotinic acid and/or nicotinamide riboside and/or one or more nicotinic acid metabolites that is about 10 nM. In yet another aspect, the amount of nicotinic acid and/or nicotinamide riboside and/or one or more nicotinic acid metabolites can be capable of achieving a serum level of the nicotinic acid and/or nicotinamide riboside and/or one or more nicotinic acid metabolites that is between about 1-100 nM.

In some cases, the composition disclosed herein can be effective in lowering triglyceride level, total cholesterol or LDL level in the subject by at least about 5%. In some cases, the amount of component (a) and (b) in the composition can synergistically reduce lipid content in said subject when administered to the subject. In some embodiments, the component (a) and component (b) in the composition can synergistically enhance a decrease in weight gain of the subject, an increase in fat oxidation of the subject, or an increase in activation of Sirt1 in the subject.

In some embodiments, the amount of nicotinic acid and/or nicotinamide riboside and/or nicotinic acid metabolites in the compositions described herein can be insufficient to reduce lipid content in the absence of the leucine and/or one or more leucine metabolites.

In some cases, the composition disclosed herein can be contained in a foodstuff.

In some embodiments, the subject compositions can comprise a portion of the leucine and/or one or more leucine metabolites that is in a free form. In some embodiments, a portion of the leucine and/or one or more leucine metabolites can be in a salt form.

In some aspect of the invention, the composition can further comprise resveratrol.

In some cases, the composition can be formulated for oral administration. In some cases, the composition can be a tablet, a capsule, a pill, a granule, an emulsion, a gel, a plurality of beads encapsulated in a capsule, a powder, a suspension, a liquid, a semi-liquid, a semi-solid, a syrup, a slurry or a chewable form.

In some cases, the component (a) and component (b) comprised in the composition as described herein can be separately packaged. In some embodiments, the component (a) and component (b) can be mixed.

The composition as described herein can be substantially free of each amino acid selected from the group consisting of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine. In some cases, the composition can be substantially free of each free amino acid selected from the group consisting of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine. In some cases, the composition can contain less than about 0.1% of each free amino acid selected from the group consisting of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine. In some embodiments, the composition can contain less than about 10% of non-leucine amino acids.

In another aspect, the one or more leucine metabolites that can be comprised in the compositions as described herein can be selected from the group consisting of keto-isocaproic acid (KIC), alpha-hydroxy-isocaproic acid, and HMB. In some embodiments, the composition disclosed herein can not contain nicotinamide.

In yet another aspect, the composition disclosed herein can further comprise one or more therapeutic agents that are capable of lowering lipid accumulation. In some embodiments, the one or more therapeutic agents that can be comprised in the compositions described herein can be selected from the group consisting of HMG-CoA inhibitor, fibrate, bile acid sequestrant, ezetimibe, lomitapide, phytosterols, CETP antagonist, orlistat, and any combination thereof.

In some embodiments, the molar ratio of component (a) to (b) in the composition described herein can be greater than about 20.

In some embodiments, the composition described herein can be formulated in a unit dosage form.

In another aspect, current invention also provides kits that comprise a multi-day supply of unit dosages of the composition described herein and instructions directing the administration of said multi-day supply over a period of multiple days.

In yet another aspect, current invention further provides methods of lowering total cholesterol level in a subject in need thereof that comprise administering to said subject the composition disclosed herein to effect the total cholesterol level in the subject. In some embodiments, current invention also provides methods of lowering total lipid content in a subject in need thereof that comprise administering to said subject the composition disclosed herein to effect the total lipid content in the subject.

In one aspect, current invention also provides methods of lowering total cholesterol level in a subject in need thereof that comprise administering to said subject a dose of a composition comprising leucine and/or one or more leucine metabolites and an amount of nicotinic acid and/or nicotinic acid metabolites to effect the total cholesterol level in the subject.

In some embodiments, the amount of nicotinic acid and/or nicotinamide riboside and/or nicotinic acid metabolites that can be used in the methods disclosed herein can be less than about 250 mg. In some embodiments, the amount of nicotinic acid and/or nicotinamide riboside and/or nicotinic acid metabolites that can be used in the methods disclosed herein can be less than about 100 mg. In some embodiments, the amount of nicotinic acid and/or nicotinamide riboside and/or nicotinic acid metabolites that can be used in the methods described herein can be less than about 25 mg. In some embodiments, the amount of nicotinic acid and/or nicotinamide riboside and/or nicotinic acid metabolites that can be used in the methods described herein can be less than about 10 mg. In some embodiments, the dose of the composition that can be used in the methods disclosed herein can be a unit dose.

In another aspect of the invention, methods of reducing a side effect of nicotinic acid and/or nicotinamide riboside and/or one or more nicotinic acid metabolites are disclosed, wherein the side effect can be characterized by an increase in cutaneous vasodilation in a subject administered with nicotinic acid and/or nicotinamide riboside and/or the one or more nicotinic acid metabolites, and the methods comprise administering a composition comprising an effective amount of leucine and/or one or more leucine metabolites to said subject that can be administered with nicotinic acid and/or the one or more nicotinic acid metabolites.

In some embodiments, the method as described herein can involve administering the composition orally.

In some cases, the effective amount or leucine and/or leucine matabolites that are used in the methods described herein can comprises at least about 500 mg of leucine and/or at least about 200 mg of the one or more leucine metabolites. In some embodiments, the effective amount of the leucine and/or leucine metabolites can comprise at least about 250 mg of leucine and/or at least about 25 mg of the one or more leucine metabolites.

In some embodiments, the methods disclosed herein can involve nicotinic acid and/or nicotinamide riboside and/or one or more nicotinic acid metabolites that is in a sub-therapeutic amount if administered alone. In some embodiments, the nicotinic acid and/or nicotinamide riboside and/or one or more nicotinic acid metabolites used in the methods described herein can be in an amount that is less than about 1 g. In some embodiments, the nicotinic acid and/or nicotinamide riboside and/or one or more nicotinic acid metabolites used in the methods disclosed herein can be in an amount that is less than about 250 mg. In some embodiments, the amount of nicotinic acid and or nicotinamide riboside and/or one or more nicotinic acid metabolites that is used in the methods described herein can be between about 1-100 mg.

In some cases, the methods described herein can use an amount of nicotinic acid and or nicotinamide riboside and/or one or more nicotinic acid metabolites that is capable of achieving a serum level of nicotinic acid and/or nicotinamide riboside and/or one or more nicotinic acid metabolites that is between about 1-100 nM.

In yet another aspect of the invention, methods of reducing atherosclerotic plaque size in a subject in need thereof are provided. The methods comprise administering to said subject a dose of a composition comprising leucine and/or one or more leucine metabolites and an amount of nicotinic acid and/or nicotinic acid metabolites to effect the total atherosclerotic plaque size in the subject.

In some embodiments, the amount of nicotinic acid and/or nicotinamide riboside and/or nicotinic acid metabolites that can be used in the methods described herein can be less than about 250 mg. In some embodiments, the amount of nicotinic acid and/or nicotinamide riboside and/or nicotinic acid metabolites can be between about 1-100 mg. In some embodiments, the amount of nicotinic acid and/or nicotinamide riboside and/or nicotinic acid metabolites can be less than about 25 mg.

In some cases, the methods described herein can involve administering the composition to the subject for at least about 1 year.

In some embodiments, the dose of the composition used in the methods described herein can be a unit dose.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent application file contains at least one drawing executed in color. Copies of this patent or patent application with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 12:
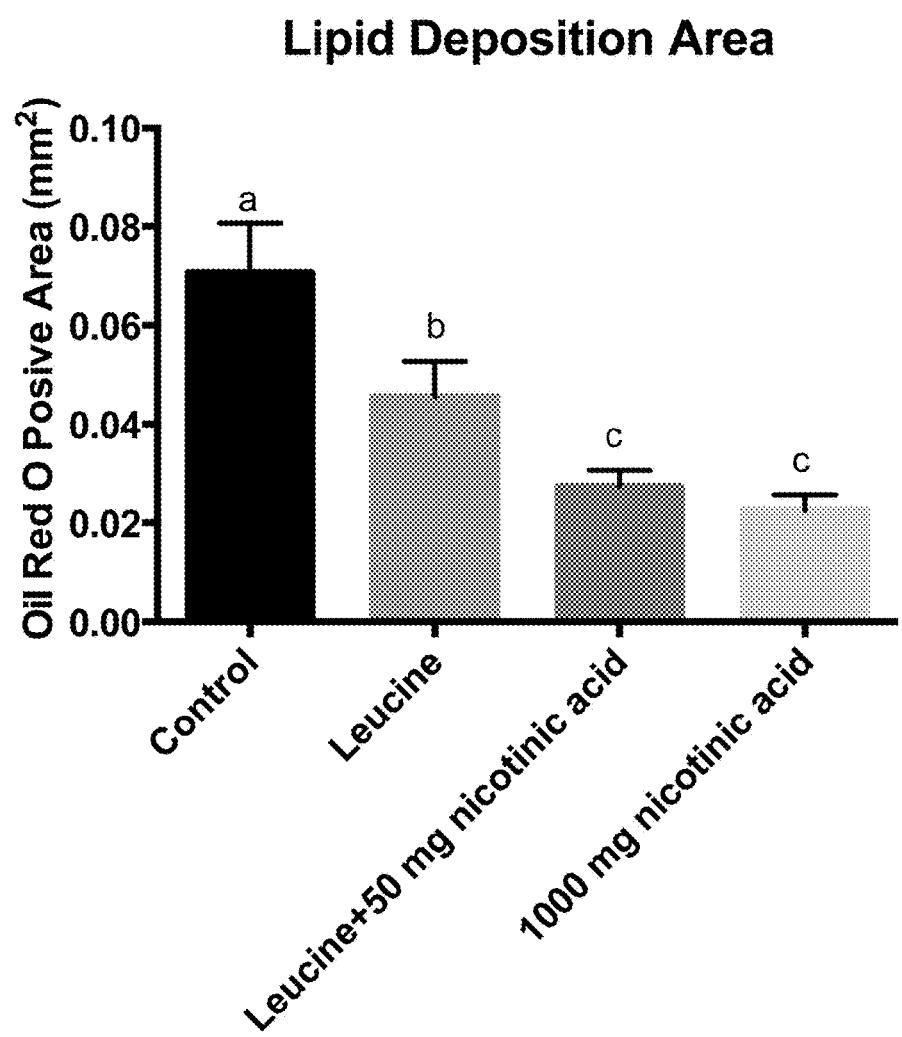

FIG. 12 illustrates the effects of eight weeks treatment with Leucine (Leu, 24 g/kg diet), Leu (24 g/kg diet)+nicotinic acid (NA, 50 mg/kg diet), and NA (1,000 mg/kg diet) added to a Western Diet (WD) on Lipid Deposition Area, as observed by the Oil Red O positive area in LDL receptor knockout mice.

Figure 13:
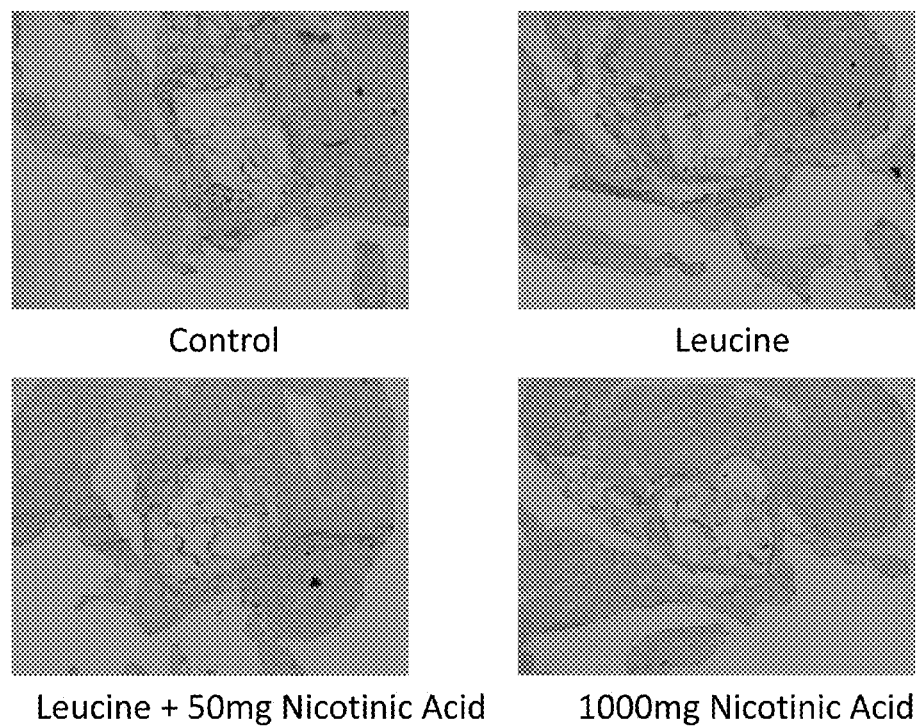

FIG. 13 illustrates the effects of eight weeks treatment with Leucine (Leu, 24 g/kg diet), Leu+nicotinic acid (NA, 50 mg/kg diet), and NA (1,000 mg/kg diet) added to a Western Diet (WD) on aortic macrophage infiltration in LDL receptor knockout mice.

Figure 14:
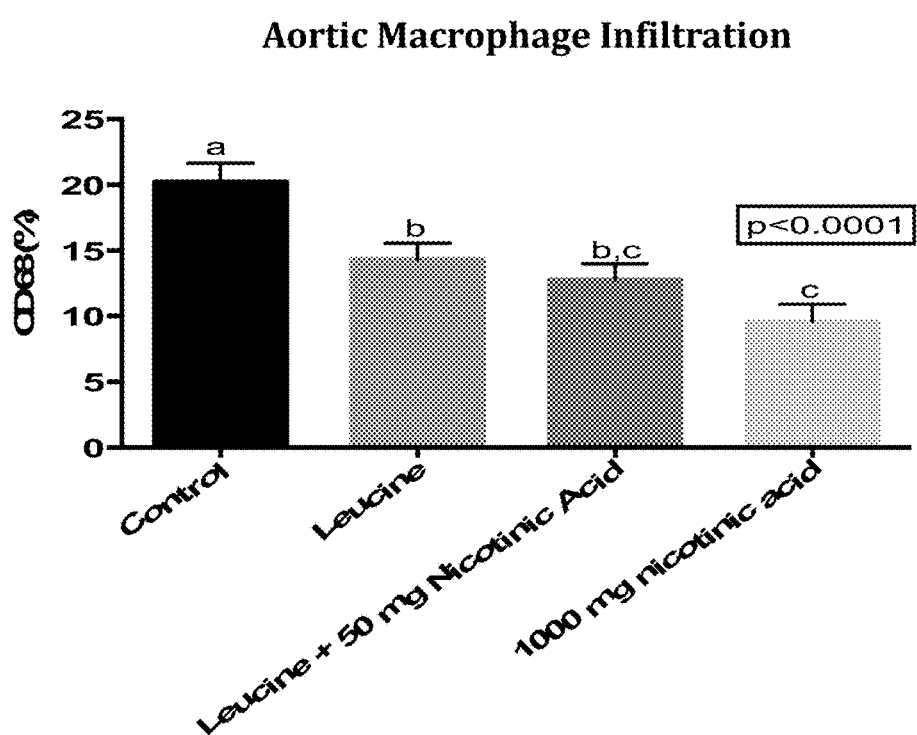

FIG. 14 illustrates the quantitative effects of eight weeks treatment with Leucine (Leu, 24 g/kg diet), Leu+nicotinic acid (NA, 50 mg/kg diet), and NA (1,000 mg/kg diet) added to a Western Diet (WD) on aortic macrophage infiltration (measured as percent CD 68 positive area) in LDL receptor knockout mice.

Figure 15:
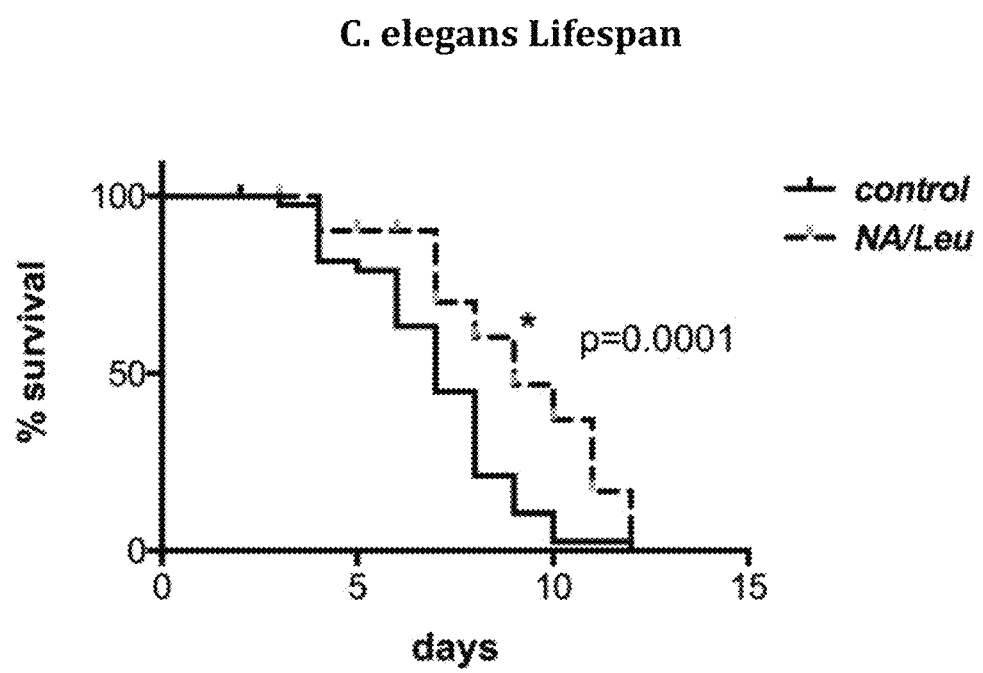

FIG. 15 illustrates the effects of nicotinic acid and leucine on the lifespan of C. elegans. NA refers to nicotinic acid; Leu refers to leucine. *p<0.0001. Data expressed as % survival over time.

DETAILED DESCRIPTION OF THE INVENTION

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "subject" or "individual" includes mammals. Non-limiting examples of mammals include humans and mice, including transgenic and non-transgenic mice. The methods described herein can be useful in both human therapeutics, pre-clinical, and veterinary applications. In some embodiments, the subject is a mammal, and in some embodiments, the subject is human. Other mammals include, and are not limited to, apes, chimpanzees, orangutans, monkeys; domesticated animals (pets) such as dogs, cats, guinea pigs, hamsters, mice, rats, rabbits, and ferrets; domesticated farm animals such as cows, buffalo, bison, horses, donkey, swine, sheep, and goats; or exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, pandas, giant pandas, hyena, seals, sea lions, and elephant seals.

The terms "administer", "administered", "administers" and "administering" are defined as the providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments of the subject application, oral routes of administering a composition can be preferred.

As used herein, "agent" or "biologically active agent" refers to a biological, pharmaceutical, or chemical compound or other moiety. Non-limiting examples include simple or complex organic or inorganic molecule, a peptide, a protein, a peptide nucleic acid (PNA), an oligonucleotide (including e.g., aptomer and polynucleotides), an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "effective amount" or "therapeutically effective amount" refers to that amount of a compound described herein that is sufficient to affect the intended application including but not limited to disease or condition treatment, as defined below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

The term "energy metabolism," as used herein, refers to the transformation of energy that accompanies biochemical reactions in the body, including cellular metabolism and mitochondrial biogenesis. Energy metabolism can be quantified using the various measurements described herein, for example and without limitations, weight-loss, fat-loss, insulin sensitivity, fatty acid oxidation, glucose utilization, triglyceride content, Sirt 1 expression level, AMPK expression level, oxidative stress, and mitochondrial biomass.

The term "isolated", as applied to the subject components, for example a PDE 5 inhibitor, including but not limited to nicotinic acid and/or nicotinamide riboside and/or one or more nicotinic acid metabolites, leucine and leucine metabolites (such as HMB), and resveratrol, refers to a preparation of the substance devoid of at least some of the other components that can also be present where the substance or a similar substance naturally occurs or is initially obtained from. Thus, for example, an isolated substance can be prepared by using a purification technique to enrich it from a source mixture. Enrichment can be measured on an absolute basis, such as weight per volume of solution, or it can be measured in relation to a second, potentially interfering substance present in the source mixture. Increasing enrichment of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis.

A "sub-therapeutic amount" of an agent, an activator or a therapy is an amount less than the effective amount of that agent, activator or therapy for an intended application, but when combined with an effective or sub-therapeutic amount of another agent or therapy can produce a desired result, due to, for example, synergy in the resulting efficacious effects, and/or reduced side effects.

A "synergistic" or "synergizing" effect can be such that the one or more effects of the combination compositions are greater than the one or more effects of each component alone, or they can be greater than the sum of the one or more effects of each component alone. The synergistic effect can be about, or greater than about 10, 20, 30, 50, 75, 100, 110, 120, 150, 200, 250, 350, or 500% or even more than the effect on a subject with one of the components alone, or the additive effects of each of the components when administered individually. The effect can be any of the measurable effects described herein.

The term "substantially free", as used herein, refers to compositions that have less than about 10%, less than about 5%, less than about 1%, less than about 0.5%, less than 0.1% or even less of a specified component. For example a composition that is substantially free of non-branched chain amino acids can have less than about 1% of the non-branched chain amino acid lysine. The percentage can be determined as a percent of the total composition or a percent of a subset of the composition. For example, a composition that is substantially free of non-branched chain amino acids can have less than 1% of the non-branched chain amino acids as a percent of the total composition, or as a percent of the amino acids in the composition. The percentages can be mass, molar, or volume percentages.

The terms "clinical significance" or "clinically significant" indicate behaviors and symptoms that are considered to be outside the range of normal, and are marked by distress and impairment of daily functioning. For example, a clinically significant cutaneous vasodilation would be a level sufficient to elicit patient complaint regarding discomfort secondary to acute vasodilatation, including flushing, itching and/or tingling. Levels of cutaneous vasodilation can also be measured by any methods known in the medical art, such as the methods including laser-Doppler flowmeter that are disclosed in Saumet J. L. et al., "Non-invasive measurement of skin blood flow: comparison between plethysmography, laser-Doppler flowmeter and heat thermal clearance method" Int. J. Microcirc. Clin. Exp. 1986; 5:73-83. A clinically significant level of cutaneous vasodilation can also be a level that is statistically significant. A clinically significant level of cutaneous vasodilation can also be a level that is not statistically significant.

The terms "lipid content" or "lipid level" refer to the content or level of lipid or lipoprotein molecules measured inside of a subject. It can be the concentration of the lipid molecules in a circulating bloodstream, or a total quantity of body fat. The lipid or lipoprotein molecules can include triglyceride, cholesterol, LDL, or HDL.

Compositions

The subject compositions comprise a combination of (i) leucine and/or one or more leucine metabolites, and (ii) nicotinic acid and/or nicotinamide riboside and/or one or more nicotinic acid metabolites. The composition can be used to treat hyperlipidemia. The compositions can further comprise resveratrol or one or more therapeutic agents that is capable of lowering lipid level. The combination of these components can be useful for lowering lipid content, lowering total cholesterol level, lowering LDL level, lowering triglyceride level or increasing HDL level. In some embodiments, the components are formulated to provide a synergistic effect, including but not limited to further reduction of the fat content or reduction in dosing amounts leading to reduced side effects to the subject. The combination can be particularly effective in lowering the lipid content while causing a reduced degree of cutaneous vasodilation in a subject as compared to a dose of nicotinic acid alone that has the same effectiveness as the composition in lowering lipid content. The amount of nicotinic acid and/or nicotinamide riboside and/or one or more nicotinic acid metabolites in the composition can be a sub-therapeutic amount in the absence of the leucine and/or one or more leucine metabolites.

In one embodiment, the subject composition comprises leucine and/or one or more leucine metabolites; and nicotinic acid and/or nicotinamide riboside and/or nicotinic acid metabolites, wherein the composition comprises at least about 250 mg of leucine and/or at least about 25 mg of the one or more leucine metabolites, and further wherein the composition comprises at least about 1 mg of nicotinic acid and/or nicotinamide riboside and/or one or more nicotinic acid metabolites.

In another embodiment, the subject composition comprises leucine and/or one or more leucine metabolites; and nicotinic acid and/or nicotinamide riboside and/or nicotinic acid metabolites, wherein the composition comprises at least about 250 mg of leucine and/or at least about 10, 20, 25, 30, 35, 40, 45, 50, 55, 60 mg of the one or more leucine metabolites, and further wherein the composition is substantially free of each of the amino acids including but are not limited to: alanine, glycine, glutamic acid and proline.

In yet another embodiment, the subject composition comprises leucine and/or one or more leucine metabolites; and an amount of nicotinic acid and/or nicotinamide riboside and/or nicotinic acid metabolites, wherein the composition comprises at least about 250 mg of leucine and/or at least about 25 mg of the one or more leucine metabolites, and further wherein the amount of nicotinic acid and/or nicotinamide riboside and/or nicotinic acid metabolites is insufficient to demonstrate a therapeutic effect such as reducing lipid content in the absence of the leucine and/or one or more leucine metabolites. In some embodiments, the amount of the nicotinic acid and/or nicotinamide riboside and/or one or more nicotinic acid metabolites is sub-therapeutic when administered without leucine and/or one or more leucine metabolites.

In still yet another embodiment, the subject composition comprises leucine and/or one or more leucine metabolites; and nicotinic acid and/or nicotinamide riboside and/or nicotinic acid metabolites, wherein the composition is effective in lowering lipid content in a subject in need thereof while causing a reduced degree of cutaneous vasodilation in the subject as compared to a dose of nicotinic acid alone that has the same effectiveness as the composition in lowering lipid content. In some embodiments, the composition is effective in lowering lipid content in a subject in need thereof without causing a clinically significant cutaneous vasodilation.

In another embodiment, the subject composition comprises (a) leucine and/or one or more leucine metabolites; and (b) nicotinic acid and/or nicotinamide riboside and/or nicotinic acid metabolites, wherein the mass ratio of (a) to (b) is at least about 10, 15, 20, 25, 30, 35, 40, 45, 50, 55, 60, 65, 70, 75, or 100, and wherein the composition comprises at least about 1 mg of the nicotinic acid and/or nicotinamide riboside and/or nicotinic acid metabolites. As described herein, a dosing of at least about 1 mg of nicotinic acid and/or nicotinamide riboside and/or nicotinic acid metabolites can provide a sub-therapeutic dosing that can be effective when combined with a sufficient mass ratio of leucine or leucine metabolite.

In some embodiments, the subject composition comprises (a) leucine and/or one or more leucine; and (b) nicotinic acid and/or nicotinamide riboside and/or one or more nicotinic acid metabolites, wherein component (a) and component (b) have synergistic effects. The synergistic effects can be synergistically enhances a decrease in weight gain of the subject, a decrease in lipid content, a decrease in LDL level, an increase in HDL level, a decrease in cholesterol level, a decrease in triglyceride level, an increase in fat oxidation of the subject, or an increase in activation of Sirt1 in the subject.

In one aspect of the invention, the subject composition comprises (a) leucine and/or one or more leucine; and (b) nicotinic acid and/or nicotinamide riboside and/or one or more nicotinic acid metabolites. The composition can further comprise at least about 0.01, 0.05, 0.1, 0.5, or 1 µg of resveratrol.

In yet another embodiment, the subject composition comprises (a) leucine and/or one or more leucine metabolites; and (b) nicotinic acid and/or nicotinamide riboside and/or nicotinic acid metabolites, wherein (b) are present in an amount effective to achieve a circulating level of about 1-100 nM of nicotinic acid and/or nicotinamide riboside and/or nicotinic acid metabolites in a subject. In some embodiments, the circulating level of nicotinic acid and/or nicotinamide riboside and/or nicotinic acid metabolites is 10 nM. These targeted circulating levels correspond to treatment concentrations described herein (see Examples), which were shown to provide beneficial effects on hyperlipidemic conditions in a subject.

Nicotinic Acid, Nicotinamide Riboside and Nicotinic Acid Metabolites

The invention provides for compositions that include nicotinic acid and/or nicotinamide riboside and/or nicotinic acid metabolites. The nicotinic acid and/or nicotinamide riboside and/or nicotinic acid metabolites can be used in free form. The term "free," as used herein in reference to a component, indicates that the component is not incorporated into a larger molecular complex. In some embodiments, the nicotinic acid can be comprised in niacin. The nicotinic acid and/or nicotinamide riboside and/or nicotinic acid metabolites can be in a salt form.

In some embodiments, the compositions can be substantially free of nicotinamide and/or nicotinamide metabolites. The nicotinamide and/or nicotinamide metabolites can counteract the effects of nicotinic acid or nicotinamide riboside. Nicotinamide can be harmful to the liver in high doses (as disclosed in http://www.livestrong.com/article/448906-therapeutic-levels-of-niacin-to-lower-cholesterol-levels/#ixzz2NO3KhDZu). The mass or molar amount of nicotinamide and/or nicotinamide metabolites can be less than about 0.01, 0.1, 0.5, 1, 2, 5, or 10% of the total composition. The mass or molar amount of nicotinamide and/or nicotinamide metabolites can be less than about 0.01, 0.1, 0.5, 1, 2, 5, or 10% of the total composition.

Without being limited to theory, ingestion of nicotinic acid and/or nicotinamide riboside and/or nicotinic acid metabolites can lower lipid content, lower triglyceride level, lower LDL level, lower total cholesterol level, or increase HDL level. The ingestion of nicotinic acid and/or nicotinamide riboside and/or nicotinic acid metabolites can also increase fat oxidation or stimulate sirtuin signaling, including increase activation of Sirt1 and Sirt3. In some embodiments, any of the compositions described herein can include salts, derivatives, metabolites, catabolites, anabolites, precursors, and analogs of nicotinic acid. For example, the metabolites can include nicotinyl CoA, nicotinuric acid, nicotinate mononucleotide, nicotinate adenine dinucleotide, or nicotinamide adenine dinucleotide. In some embodiments, the compositions cannot comprise nicotinamide. In some embodiments, the compositions comprise nicotinamide. In some embodiments, the compositions can be substantially free of nicotinic acid metabolites.

Leucine and Leucine Metabolites

The invention provides for compositions that include leucine and/or leucine metabolites. The leucine and/or leucine metabolites can be used in free form. The term "free," as used herein in reference to a component, indicates that the component is not incorporated into a larger molecular complex. For example a composition can include free leucine that is not incorporated in a protein or free hydroxymethylbutyrate. The leucine can be L-leucine. The leucine and/or leucine metabolites can be in a salt form.

Without being limited to theory, ingestion of branched chain amino acids, such as leucine, can stimulate sirtuin signaling, including Sirt1 and Sirt3, as well as AMPK signaling, one or more of which can favorably modulate inflammatory cytokine patterns. In some embodiments, any of the compositions described herein can include salts, derivatives, metabolites, catabolites, anabolites, precursors, and analogs of leucine. For example, the metabolites can include hydroxymethylbutyrate (HMB), keto-isocaproic acid (KIC), and keto isocaproate. The HMB can be in a variety of forms, including calcium 3-hydroxy-3-methylbutyrate hydrate.

In certain embodiments of the invention, any of the compositions disclosed herein can be formulated such that they do not contain (or exclude) one or more amino acids selected from the group consisting of lysine, glutamate, proline, arginine, valine, isoleucine, aspartic acid, asparagine, glycine, threonine, serine, phenylalanine, tyrosine, histidine, alanine, tryptophan, methionine, glutamine, taurine, carnitine, cystine and cysteine.

In some embodiments, the compositions can be substantially free of one or more, or all non-leucine amino acids. For example, the compositions can be free of alanine, arginine, asparagine, aspartic acid, cysteine, glutamic acid, glutamine, glycine, histidine, isoleucine, lysine, methionine, phenylalanine, proline, serine, threonine, tryptophan, tyrosine, and/or valine.

The compositions can be substantially free of free non-leucine amino acids such as alanine, arginine, asparagine, aspartic acid, cysteine, glutamic acid, glutamine, glycine, histidine, isoleucine, lysine, methionine, phenylalanine, proline, serine, threonine, tryptophan, tyrosine, and/or valine.

In some embodiments, the compositions can be substantially free of one or more, or all of non-branched chain or non-leucine amino acids. For example, the compositions can be free of alanine, arginine, asparagine, aspartic acid, cysteine, glutamic acid, glutamine, glycine, histidine, lysine, methionine, phenylalanine, proline, serine, threonine, tryptophan, and/or tyrosine. In some embodiments, the compositions can be substantially free of isoleucine and/or valine. The subject compositions can be substantially free of the individual amino acids alanine, glycine, glutamic acid, and proline. The subject compositions can be substantially free of one or more of the individual amino acids alanine, glycine, glutamic acid, and proline. The subject compositions can be substantially free of alanine. The subject compositions can be substantially free of glycine. The subject compositions can be substantially free of valine. The compositions can be substantially free of any non-branched chain amino acids. The mass or molar amount of a non-branched chain amino acid can be less than about 0.01, 0.1, 0.5, 1, 2, 5, or 10% of the total composition or of the total amino acids in the composition. The mass or molar amount of a non-leucine amino acid can be less than about 0.01, 0.1, 0.5, 1, 2, 5, or 10% of the total composition or of the total amino acids in the composition.

For clarity, the amino acids described herein can be intact amino acids existing in free form or salt form thereof. For example, the subject compositions can be substantially free of free amino acids, such as alanine, glycine, glutamic acid, and proline. The mass or molar amount of a non-branched chain amino acid, any amino acid, or any non-leucine amino acid can be less than about 0.01, 0.1, 0.5, 1, 2, 5, or 10% of the total composition, of the total amino acids in the composition, or of the total free amino acids in the composition.

Therapeutic Agents

The subject compositions can further include one or more pharmaceutically active agents or therapeutic agents other than nicotinic acid and/or nicotinamide riboside and/or nicotinic acid metabolites. The therapeutic agents or pharmaceutically active agents can be any agent that is known in the art. For example, the combination compositions can further comprise a pharmaceutically active anti-hyperlipidemic agent, or a dietary supplement that also effects on lipid content. The anti-hyperlipidemic agent can be an oral agent or injectable agent. The anti-hyperlipidemic agents can be in a sub-therapeutic amount in lowering levels of total lipid content or triglyceride, LDL or cholesterol levels, or increasing the HDL level. The types of the anti-hyperlipidemic agents known in the art can include, but are not limited to, HMG-CoA inhibitors (or statins), fibrates, nicotinic acid, bile acid sequestrants (resins), cholesterol absorption inhibitors (ezetimibe), lomitapide, phytosterols, orlistat or others. The statin type anti-hyperlipidemic agents can include but are not limited to: atorvastatin, fluvastatin, pravastatin, lovastatin, simvastatin, pitavastatin, cerivastatin, rosuvastatin, or lovastatin/niacin ER. The cholesterol absorption inhibitors can include but are not limited to ezetimibe, and combination of ezetimibe with simvastatin. The fibrate type of anti-hyperlipidemic agents can include but are not limited to: gemfibrozil, fenofibrate, fenofibric acid, clofibrate, or micronized fenofibrate. The bile acid sequestrants can include but are not limited to: colestipol, cholestyramine, or colesevelam. Other types of anti-hyperlipidemic agent can include dextrothyroxine sodium or icosapent. These examples are provided for discussion purposes only, and are intended to demonstrate the broad scope of applicability of the invention to a wide variety of drugs. It is not meant to limit the scope of the invention in any way.

The subject composition can further comprise one or more therapeutic agents that are herbs and/or supplements. The herbs and/or supplements can have therapeutic effects that are unproven scientifically. The examples of the herbs and/or the supplements can be, but are not limited to: Acai, Alfalfa, Aloe, Aloe Vera, Aristolochic Acids, Asian *Ginseng*, *Astragalus, Bacillus coagulans, Belladonna*, Beta-carotene, Bifidobacteria, Bilberry, Bilberry, Biotin, Bitter Orange, Black Cohosh, Black Cohosh, Black *psyllium*, Black tea, Bladderwrack, Blessed thistle, Blond *psyllium*, Blueberry, Blue-green algae, Boron, Bromelain, Butterbur, Calcium, Calendula, Cancell/Cantron/Protocel, Cartilage (Bovine and Shark), *Cassia* cinnamon, Cat's Claw, Chamomile, Chasteberry, Chondroitin sulfate, Chromium, Cinnamon, Clove, Coenzyme Q-10, Colloidal Silver Products, Cranberry, Creatine, Dandelion, Dandelion, Devil's claw, DHEA, Dong quai, *Echinacea*, Ephedra, Essiac/Flor-Essence, *Eucalyptus*, European Elder (Elderberry), European Mistletoe, Evening Primrose Oil, Fenugreek, Feverfew, Fish oil, Flaxseed, Flaxseed oil, Folate, Folic acid, Garlic, Ginger, Gingko, *Ginseng*, Glucosamine hydrochloride, Glucosamine sulfate, Goldenseal, Grape Seed Extract, Green Tea, Hawthorn, Hoodia, Horse Chestnut, Horsetail, Hydrazine Sulfate, Iodine, Iron, Kava, *Lactobacillus*, Laetrile/Amygdalin, L-arginine, Lavender, Licorice, *Lycium*, Lycopene, Magnesium, Manganese, Melatonin, Milk Thistle, Mistletoe Extracts, Noni, Oral Probiotics, Pantothenic acid (Vitamin B5), Passionflower, PC-SPES, Pennyroyal, Peppermint, Phosphate salts, Pomegranate, Propolis, Pycnogenol, Pyridoxine (Vitamin B6), Red Clover, Red yeast, Riboflavin (Vitamin B2), Roman chamomile, *Saccharomyces boulardii*, S-Adenosyl-L-Methionine (SAMe), Sage, Saw Palmetto, Selected Vegetables/Sun's Soup, Selenium, *Senna*, Soy, St. John's Wort, sweet orange essence, Tea Tree Oil, Thiamine (Vitamin B1), Thunder God Vine, Turmeric, Valerian, Vitamin A, Vitamin B12, Vitamin C, Vitamin D, Vitamin E, Vitamin K, Wild yam, Yohimbe, Zinc or 5-HTP.

The amount of pharmaceutical agent, or any other component used in a combination composition described herein, can be a used in an amount that is sub-therapeutic. In some embodiments, using sub-therapeutic amounts of an agent or component can reduce the side-effects of the agent. Use of sub-therapeutic amounts can still be effective, particularly when used in synergy with other agents or components.

A sub-therapeutic amount of the agent or component can be such that it is an amount below which would be considered therapeutic. For example, FDA guidelines can suggest a specified level of dosing to treat a particular condition, and a sub-therapeutic amount would be any level that is below the FDA suggested dosing level. The sub-therapeutic amount can be about 1, 5, 10, 15, 20, 25, 30, 35, 50, 75, 90, or 95% less than the amount that is considered to be a therapeutic amount. The therapeutic amount can be assessed for individual subjects, or for groups of subjects. The group of subjects can be all potential subjects, or subjects having a particular characteristic such as age, weight, race, gender, or physical activity level.

In the case of nicotinic acid administered alone to lower lipid content, the physician suggested starting dose is 1000-3000 mg daily, with subject specific dosing having a range of 1 mg to a maximum of 1000 mg daily when administered with leucine and/or leucine metabolites. The particular dosing for a subject can be determined by a clinician by titrating the dose and measuring the therapeutic response. The therapeutic dosing level can be determined by measuring fasting plasma cholesterol and LDL levels without causing clinically significant cutaneous vasodilation. A sub-therapeutic amount can be any level that would be below the recommended dosing of nicotinic acid. For example, if a subject's therapeutic dosing level is determined to be 700 mg daily, a dose of 600 mg would be a sub-therapeutic amount. Alternatively, a sub-therapeutic amount can be determined relative to a group of subjects rather than an individual subject. For example, if the average therapeutic amount of nicotinic acid, nicotinamide riboside or nicotinic acid metabolites for subjects with weights over 300 lbs is 2000 mg, then a sub-therapeutic amount can be any amount below 2000 mg. In some embodiments, the dosing can be recommended by a healthcare provider including, but not limited to a patient's physician, nurse, nutritionist, pharmacist, or other health care professional. A health care professional can include a person or entity that is associated with the health care system. Examples of health care professionals can include surgeons, dentists, audiologists, speech pathologists, physicians (including general practitioners and specialists), physician assistants, nurses, midwives, pharmaconomists/pharmacists, dietitians, therapists, psychologists, physical therapists, phlebotomists, occupational therapists, optometrists, chiropractors, clinical officers, emergency medical technicians, paramedics, medical laboratory technicians, radiographers, medical prosthetic technicians social workers, and a wide variety of other human resources trained to provide some type of health care service.

In the case of nicotinic acid, nicotinamide, or nicotinic acid metabolites, the therapeutically effective level of the nicotinic acid, nicotinamide riboside, nicotinic acid metabolites can be a circulating level between about 1-100 nM. A sub-therapeutic level of the nicotinic acid, nicotinamide riboside, or nicotinic acid metabolites, by itself or in any combination, can be any circulating level at least about, less than about, or more than about 1, 2.5, 5, 10, 15, 20, 25, 30, 35, 40, 45, 50, 60, 70, 80, 90 or 100 nM. The sub-therapeutic level of the nicotinic acid and/or nicotinamide riboside and/or nicotinic acid metabolites, in a subject composition formulated for administration can be less than about 1, 5, 10, 20, 30, 50, 60, 70, 80, 90, 100, 125, 150, 175, 200, 250, 300, 350, 400, 450, 500, 600, 700, 750, 800, 900 or 1000 mg of the nicotinic acid and/or nicotinamide riboside and/or nicotinic acid metabolites.

Any of the components described herein, including leucine, HMB, KIC, nicotinic acid, nicotinamide riboside, and resveratrol can be used in a subject composition in free form, isolated form, purified from a natural source, and/or purified or prepared from a synthetic source. The natural source can be an animal source or plant source. The components can be pure to at least about 95, 97, 99, 99.5, 99.9, 99.99, or 99.999%.

Dosing Amounts

The invention provides for compositions that are combinations of isolated components, such as leucine, metabolites of leucine, such as HMB, nicotinic acid, nicotinamide riboside, and/or resveratrol, that have been isolated from one or more sources. The invention provides for compositions that are enriched in leucine, metabolites of leucine, such as FMB, nicotinic acid and/or nicotinamide riboside, and/or resveratrol. The components can be isolated from natural sources or created from synthetic sources and then enriched to increase the purity of the components. Additionally, leucine can be isolated from a natural source and then enriched by one or more separations. The isolated and enriched components, such as leucine, can then be combined and formulated for administration to a subject.

In some embodiments, a composition comprises an amount of nicotinic acid and/or nicotinamide riboside and/or nicotinic acid metabolites. The amount of nicotinic acid and/or nicotinamide riboside and/or nicotinic acid metabolites can be a subtherapeutic amount, and/or an amount that is synergistic with one or more other compounds in the composition or one or more of the compounds administered simultaneously or in close temporal proximity with the composition. In some embodiments, the nicotinic acid and/or nicotinamide riboside and/or nicotinic acid metabolites is administered in a low dose, a medium dose, or a high dose, which describes the relationship between two doses, and generally do not define any particular dose range. The compositions can be administered to a subject such that the subject is administered a selected total daily dose of the composition. The total daily dose can be determined by the sum of doses administered over a 24 hour period.

A dose, which can be a unit dose, can comprise about, more than about, or less than about 200, 250, 400, 500, 550, 600, 700, 800, 900, 1000, 1100, 1250, 1300 or more mg of leucine. The leucine can be free leucine. In some embodiments, a unit dose can comprise at least about 1000 mg of free leucine. The composition can comprise between about 10-1250, 200-1250, or 500-1250 mg of leucine. A dose, which can be a unit dose, can comprise about, more than about, or less than about 10, 15, 20, 25, 30, 35, 40, 45, 50, 100, 200, 250, 400, 500, 550, 600, 700, 800, 900, 1000, 1250, 1300 or more mg of a leucine metabolite, such as HMB or KIC. The leucine metabolite can be a free leucine metabolite. The composition can comprise between about 10-900, 50-750, or 400-650 mg of the leucine metabolite, such as HMB or KIC. In some embodiments, a unit dose can comprise at least about 400 mg of free FMB. The amount of leucine and leucine metabolites as described herein can be administered daily or simultaneously. The amount as described herein can be administered in one dose or separately in multiple doses daily.

In some embodiments, a daily dose of leucine can be about, less than about, or more than about 0.25-3 or 0.5-3.0 g/day (e.g. 0.5, 0.75, 1, 1.25, 1.5, 1.75, 2, 2.5, 3, or more g/day). A daily dose of HMB can be about, less than about, or more than about 0.20-3.0 g/day (e.g. 0.2, 0.4, 0.5, 0.75, 1, 1.5, 2, 2.5, 3, or more g/day). A daily dose of KIC can be about, less than about, or more than about 0.2-3.0 g/day (e.g. 0.2, 0.4, 0.5, 0.75, 1, 1.25, 1.5, 1.75, 2, 2.5, 3, or more g/day).

The dose of leucine or metabolite thereof, can be a therapeutic dose. The dose of leucine or metabolite thereof can be a sub-therapeutic dose. A sub-therapeutic dose of leucine can be about, less than about, or more than about 0.25-3.0 g (e.g. 0.25, 0.5, 0.75, 1, 1.25, 1.5, 1.75, 2, 2.5, 3, or more g). A sub-therapeutic dose of leucine can be about, less than about, or more than about 0.25-3.0 g/day (e.g. 0.25, 0.5, 0.75, 1, 1.25, 1.5, 1.75, 2, 2.5, 3, or more g/day). In some embodiments, the compositions comprises less than 3.0 g daily dosage of leucine. A sub-therapeutic dose of HMB can be about, less than about, or more than about 0.05-3.0 g (e.g. 0.05, 0.1, 0.2, 0.4, 0.5, 0.75, 1, 1.5, 2, 2.5, 3, or more g). A sub-therapeutic dose of HMB can be about, less than about, or more than about 0.05-3.0 g/day (e.g. 0.05, 0.1, 0.2, 0.4, 0.5, 0.75, 1, 1.5, 2, 2.5, 3, or more g/day). A sub-therapeutic dose of KIC can be about, less than about, or more than about 0.1-3.0 g (e.g. 0.1, 0.2, 0.4, 0.5, 0.75, 1, 1.25, 1.5, 1.75, 2, 2.5, 3, or more g). A sub-therapeutic dose of KIC can be about, less than about, or more than about 0.1-3.0 g/day (e.g. 0.1, 0.2, 0.4, 0.5, 0.75, 1, 1.25, 1.5, 1.75, 2, 2.5, 3, or more g/day).

A dose, which can be a unit dose, can comprise nicotinic acid, nicotinamide riboside or nicotinic acid metabolites, that can be about, more than about, or less than about 0.01, 0.05, 0.1, 0.5, 1, 2, 5, 10, 20, 40, 60, 80, 100, 200, 250, 400, 500, 800, 1000, or 1500 mg of the nicotinic acid, nicotinamide riboside, or nicotinic acid metabolites. The composition can comprise between about 1-100, 5-50, or 10-20 mg of the nicotinic acid and/or nicotinamide riboside and/or nicotinic acid metabolites. In some embodiments, a unit dose can comprise at least about 1 mg of nicotinic acid and/or nicotinamide riboside and/or nicotinic acid metabolites. In some embodiments, a unit dose can comprise less than 250 mg of nicotinic acid and/or nicotinamide riboside and/or nicotinic acid metabolites. The dosage can be adjusted for the intended subject administered. For example, a dose that is suitable for a canine can be less than the dose that is suitable for a human. The amount of nicotinic acid, nicotinamide riboside and/or nicotinic acid metabolites as described herein can be administered daily or simultaneously. The amount as described herein can be administered in one dose or separately in multiple doses daily.

In some embodiments, the composition comprises both nicotinic acid and nicotinamide riboside, and the total amount of nicotinic acid and nicotinamide riboside can be about, more than about, or less than about 0.01, 0.05, 0.1, 0.5, 1, 2, 5, 10, 20, 40, 60, 80, 100, 200, 250, 400, 500, 600, 800, 900, 1000, or 1500 mg.

In other embodiments, a daily dose of nicotinic acid and/or nicotinamide riboside and/or nicotinic acid metabolites can be about, more than about, or less than about 0.0001 mg/kg (mg of nicotinic acid and/or nicotinamide riboside and/or nicotinic acid metabolites/kg of the subject receiving the dose), 0.005 mg/kg, 0.01 mg/kg, 0.5 mg/kg, 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, 75 mg/kg, 100 mg/kg, or more.

A dose, which can be a unit dose, can comprise about, less than about, or more than about 1, 5, 10, 25, 35, 50, 51, 75, 100, 150, 200, 250, 300, 350, 400, 450, 500, or more mg of resveratrol. The composition can comprise between about 5-500, 30-250, or 35-100 mg of resveratrol. In some embodiments, a unit dose can comprise at least about 35 mg of resveratrol. The amount of resveratrol as described herein can be administered daily or simultaneously. The amount as described herein can be administered in one dose or separately in multiple doses daily.

A daily low dose of resveratrol can comprise about, less than about, or more than about 0.5 mg/kg (mg of resveratrol/kg of the subject receiving the dose), 1 mg/kg, 2.5 mg/kg, 5 mg/kg, 7.5 mg/kg, 10 mg/kg, 12.5 mg/kg, 15 mg/kg, 20 mg/kg, 25 mg/kg, 50 mg/kg, or more; a daily medium dose of resveratrol can comprise about, less than about, or more than about 20 mg/kg, 25 mg/kg, 50 mg/kg, 75 mg/kg, 100 mg/kg, 125 mg/kg, 150 mg/kg, 175 mg/kg, 200 mg/kg, 250 mg/kg, or more; and a daily high dose of resveratrol can comprise about, less than about, or more than about 150 mg/kg, 175 mg/kg, 200 mg/kg, 225 mg/kg, 250 mg/kg, 300 mg/kg, 350 mg/kg, 400 mg/kg, or more. The dosing range as defined to low, medium or high can be dependent on the subject receiving the dose and vary from subject to subject.

In some embodiments, a composition, which can be formulated as a unit dose, can comprise (a) at least about 250 mg of leucine and/or at least about 25 mg of the one or more leucine metabolites. The composition can further comprise at least about 35 mg of resveratrol.

In some embodiments of the invention, the combination compositions can have a specified ratio of leucine and/or metabolites thereof to nicotinic acid and/or nicotinamide metabolites and/or nicotinic acid metabolites. The specified ratio can provide for effective and/or synergistic treatment of hyperlipidemic conditions, which, for example, can be measured as a reduction in total lipid content, reduction in cholesterol level, reduction in triglyceride level, reduction in LDL level, reduction in body weight, and/or increase in HDL level. The ratio of leucine amino acids and/or metabolites thereof to a nicotinic acid and/or nicotinamide riboside and/or nicotinic acid metabolite can be a mass ratio, a molar ratio, or a volume ratio.

In some embodiments, a composition can comprise (a) leucine and/or metabolites thereof (including HMB) and (b) nicotinic acid and/or nicotinamide riboside and/or nicotinic acid metabolites, where the mass ratio of (a) to (b) can be about, less than about, or greater than about 0.1, 0.5, 1, 2, 5, 10, 15, 20, 25, 50, 75, 100, 200, 300, 350, 400, 450, 500, 550, 600, 650, 700, 750, or 800. In some embodiments, the mass ratio of (a) to (b) is at least about 25. In some embodiments, the mass ratio of (a) to (b) is at least about 50. The composition can also comprise a minimal amount of nicotinic acid and/or nicotinamide riboside and/or nicotinic acid metabolites, such as 5, 10 or 50 mg of the nicotinic acid and/or nicotinamide riboside and/or nicotinic acid metabolites or a range of nicotinic acid and/or nicotinamide riboside and/or nicotinic acid metabolites amount, such as 5-250 mg of nicotinic acid and/or nicotinamide riboside and/or nicotinic acid metabolites.

In other embodiments, a composition can comprise (a) nicotinic acid and/or nicotinamide riboside and/or nicotinic acid metabolites and (b) resveratrol, where the mass ratio of (a) to (b) can be about, less than about, or greater than about 0.01, 0.05, 0.1, 0.5, 1, 2, 5, 10, 20, 50, 100, 200, 300, 350, 400, 450, 500, 550, 600, or 650.

In some embodiments, the dosing of leucine, any metabolites of leucine, nicotinic acid, nicotinamide riboside, any nicotinic acid metabolites, and resveratrol can be designed to achieve a specified physiological concentration or circulating level of leucine, metabolites of leucine, nicotinic acid, nicotinamide riboside, metabolites of nicotinic acid and/or resveratrol. The physiological concentration can be a circulating level as measured in the serum or blood stream of a subject. The subject can be a human or an animal. A selected dosing can be altered based on the characteristics of the subject, such as weight, rate of energy metabolism, genetics, ethnicity, height, or any other characteristic.

In some embodiments, a selected dose of a composition can be administered to a subject such that the subject achieves a desired circulating level of the composition. The desired circulating level of a component can be either a therapeutically effective level or a sub-therapeutic level.

The amount of leucine in a unit dose can be such that the circulating level of leucine in a subject is about or greater than about 0.25 mM, 0.5 mM, 0.75 mM, or 1 mM. A dosing of about 1,125 mg leucine (e.g., free leucine), can achieve a circulating level of leucine in a subject that is about 0.5 mM. A dosing of about 300 mg leucine (e.g., free leucine), can achieve a circulating level of leucine in a subject that is about 0.25 mM.

The desired circulating level of the composition can be at least about 0.25, 0.5, 0.75, 1 mM or more of leucine. The desired circulating level of the composition can be at least about, less than about, or more than about 0.1, 0.25, 0.5, 0.75, 1, 10, 20, 40, 60 µM or more of a leucine metabolite (such as HMB). The desired circulating level of the composition can be at least about 0.25, 0.5, 0.75, 1 mM or more of KIC.

The desired circulating level of the composition can be at least about, less than about, or more than about 0.1, 0.25, 0.5, 0.75, 1, 10, 20, 40, 60, 80, 100, 120, 200, 400, 500, 1000, 1500, 2000, 2500, or 3000 nM or more of the nicotinic acid and/or nicotinamide riboside and/or nicotinic acid metabolites. The therapeutically effective level of nicotinic acid and/or nicotinamide riboside and/or nicotinic acid metabolites can be between 44-111 µM, which corresponds to about 10-20 µg/mL.

The desired circulating level of the composition can be at least about, less than about, or more than about 40, 60, 80, 100, 120, 150, 200, 300, 400, 800, 1600, 3000, or 5000 nM or more of the resveratrol. The selected dose can be chosen based on the characteristics of the subject, such as weight, height, ethnicity, or genetics.

In some embodiments, a composition comprises leucine and nicotinic acid in amounts that are effective to achieve a circulating level of about 0.3-1 mM leucine and about 1-100 nM nicotinic acid in a subject.

An oral dosing of about 1,125 mg leucine can achieve a circulating level of leucine in a subject that is about 0.5 mM leucine. An oral dosing of about 300 mg leucine can achieve a circulating level of leucine in a subject that is about 0.25 mM.

An oral dosing of about 500 mg of HMB can achieve a circulating level of HMB in a subject that is about 5 µM HMB. An oral dosing of about 100 mg of HMB can achieve a circulating level of HMB in a subject that is about 0.8 µM HMB.

An oral dosing of about 3,000 mg nicotinic acid or nicotinamide riboside can achieve a circulating level of nicotinic acid or nicotinamide riboside in a subject that is about 10 µM nicotinic acid or nicotinamide riboside. An oral dosing of about 50 mg nicotinic acid or nicotinamide riboside can achieve a circulating level of nicotinic acid or nicotinamide riboside in a subject that is about 10-100 nM nicotinic acid or nicotinamide riboside.

An oral dosing of about 1100 mg of resveratrol can achieve a circulating level of resveratrol in a subject that is about 0.5 mM resveratrol. An oral dosing of about 50 mg of resveratrol can achieve a circulating level of resveratrol in a subject that is about 200 nM resveratrol.

In some embodiments, the compositions can be formulated to achieve a desired circulating molar or mass ratios achieved after administration one or more compositions to a subject. The compositions can be a combination composition described herein. The molar ratio can be adjusted to account for the bioavailability, the uptake, and the metabolic processing of the one or more components of a combination composition. For example, if the bioavailability of a component is low, then the molar amount of a that component can be increased relative to other components in the combination composition. In some embodiments, the circulating molar or mass ratio is achieved within about 0.1, 0.5, 0.75, 1, 3, 5, or 10, 12, 24, or 48 hours after administration. The circulating molar or mass ratio can be maintained for a time period of about or greater than about 0.1, 1, 2, 5, 10, 12, 18, 24, 36, 48, 72, or 96 hours.

In some embodiments, the circulating molar ratio of leucine to nicotinic acid or nicotinamide riboside is about, less than about, or greater than about 1, 5, 10, 20, 50, 100, 500, 1000, 5000, or 10000. In some embodiments, the circulating molar ratio of HMB to nicotinic acid or nicotinamide riboside is about or greater than about, or less than about 0.01, 0.05, 0.1, 0.5, 1, 5, 10, 20, 50, or 100. In some embodiments, the circulating molar ratio of a nicotinic acid or nicotinamide riboside to resveratrol is about, less than about, or greater than about 0.01, 0.05, 0.1, 0.5, 1, 5, 10, 20, 50, or 100.

Dosing Forms

The compositions described herein can be compounded into a variety of different dosage forms. It can be used orally as a tablet, a capsule, a pill, a granule, an emulsion, a gel, a plurality of beads encapsulated in a capsule, a powder, a suspension, a liquid, a semi-liquid, a semi-solid, a syrup, a slurry, a chewable form, caplets, soft gelatin capsules, lozenges or solution. Alternatively, the compositions can be formulated for inhalation or for intravenous delivery. The compositions can also be formulated as a nasal spray or for injection when in solution form. In some embodiments, the composition can be a liquid composition suitable for oral consumption.

Compositions formulated for inhalation can be packaged in an inhaler using techniques known in the art. An inhaler can be designed to dispense 0.25, 0.5, or 1 unit dose per inhalation. An inhaler can have a canister that holds the subject composition formulated for inhalation, a metering valve that allows for a metered quantity of the formulation to be dispensed with each actuation, and an actuator or mouthpiece that allows for the device to be operated and direct the subject composition into the subject's lungs. The formulated composition can include a liquefied gas propellant and possibly stabilizing excipients. The actuator can have a mating discharge nozzle that connects to the canister and a dust cap to prevent contamination of the actuator. Upon actuation, the subject composition can be volatized, which results in the formation of droplets of the subject composition. The droplets can rapidly evaporate resulting in micrometer-sized particles that are then inhaled by the subject. Inhalers and methods for formulating compositions for inhalation are described in are described in U.S. Pat. Nos. 5,069,204, 7,870,856 and U.S. Patent Application No. 2010/0324002, which are incorporated herein by reference in its entirety.

Compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, including liquid dosage forms (e.g., a suspension or slurry), and oral solid dosage forms (e.g., a tablet or bulk powder). Oral dosage forms can be formulated as tablets, pills, dragees, capsules, emulsions, lipophilic and hydrophilic suspensions, liquids, gels, syrups, slurries, suspensions and the like, for oral ingestion by an individual or a patient to be treated. Such dosage forms can be prepared by any of the methods of formulation. For example, the active ingredients can be brought into association with a carrier, which constitutes one or more necessary ingredients. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the inventive composition for oral use can be obtained by mixing a composition a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The liquid forms, in which the formulations disclosed herein can be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

A subject can be treated by combination of an injectable composition and an orally ingested composition.

Liquid preparations for oral administration can take the form of, for example, solutions, syrups or suspensions, or they can be presented as a dry product for reconstitution with water or other suitable vehicles before use. Such liquid preparations can be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The preparation of pharmaceutical compositions of this invention, including oral and inhaled formulations, can be conducted in accordance with generally accepted procedures for the preparation of pharmaceutical preparations. See, for example, Remington's Pharmaceutical Sciences 18th Edition (1990), E. W. Martin ed., Mack Publishing Co., PA. Depending on the intended use and mode of administration, it can be desirable to process the magnesium-counter ion compound further in the preparation of pharmaceutical compositions. Appropriate processing can include mixing with appropriate non-toxic and non-interfering components, sterilizing, dividing into dose units, and enclosing in a delivery device.

This invention further encompasses anhydrous compositions and dosage forms comprising an active ingredient, since water can facilitate the degradation of some compounds. For example, water can be added (e.g., 5%) in the arts as a means of simulating long-term storage in order to determine characteristics such as shelf-life or the stability of formulations over time. Anhydrous compositions and dosage forms of the invention can be prepared using anhydrous or low moisture containing ingredients and low moisture or low humidity conditions. Compositions and dosage forms of the invention which contain lactose can be made anhydrous if substantial contact with moisture and/or humidity during manufacturing, packaging, and/or storage is expected. An anhydrous composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An ingredient described herein can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Binders suitable for use in dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Lubricants which can be used to form compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the composition.

Lubricants can be also be used in conjunction with tissue barriers which include, but are not limited to, polysaccharides, polyglycans, seprafilm, interceed and hyaluronic acid.

Disintegrants can be used in the compositions of the invention to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Examples of suitable fillers for use in the compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

When aqueous suspensions and/or elixirs are desired for oral administration, the active ingredient therein can be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In one embodiment, the composition can include a solubilizer to ensure good solubilization and/or dissolution of the compound of the present invention and to minimize precipitation of the compound of the present invention. This can be especially important for compositions for non-oral use, e.g., compositions for injection. A solubilizer can also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crospovidone.

The compositions described herein can also be formulated as extended-release, sustained-release or time-release such that one or more components are released over time. Delayed release can be achieved by formulating the one or more components in a matrix of a variety of materials or by microencapsulation. The compositions can be formulated to release one or more components over a time period of 1, 4, 6, 8, 12, 16, 20, 24, 36, or 48 hours. The release of the one or more components can be at a constant or changing rate.

In some embodiments, a subject composition described herein can be formulated in as matrix pellets in which particles of the subject composition are embedded in a matrix of water-insoluble plastic and which are enclosed by a membrane of water-insoluble plastic containing embedded particles of lactose, produces and maintains plasma levels of the subject composition within the targeted therapeutic range. In other embodiments, a subject composition can be formulated as a sustained release tablet obtained by coating core granules composed mainly of the subject composition with a layer of a coating film composed of a hydrophobic material and a plastic excipient and optionally containing an enteric polymer material to form coated granules and then by compressing the coated granules together with a disintegrating excipient. Sustained release formulations are described in U.S. Pat. Nos. 4,803,080, and 6,426,091, which are herein incorporated by reference in its entirety.

Using the controlled release dosage forms provided herein, the one or more cofactors can be released in its dosage form at a slower rate than observed for an immediate release formulation of the same quantity of components. In some embodiments, the rate of change in the biological sample measured as the change in concentration over a defined time period from administration to maximum concentration for an controlled release formulation is less than about 80%, 70%, 60%, 50%, 40%, 30%, 20%, or 10% of the rate of the immediate release formulation. Furthermore, in some embodiments, the rate of change in concentration over time is less than about 80%, 70%, 60%, 50%, 40%, 30%, 20%, or 10% of the rate for the immediate release formulation.

In some embodiments, the rate of change of concentration over time is reduced by increasing the time to maximum concentration in a relatively proportional manner. For example, a two-fold increase in the time to maximum concentration can reduce the rate of change in concentration by approximately a factor of 2. As a result, the one or more cofactors can be provided so that it reaches its maximum concentration at a rate that is significantly reduced over an immediate release dosage form. The compositions of the present invention can be formulated to provide a shift in maximum concentration by 24 hours, 16 hours, 8 hours, 4 hours, 2 hours, or at least 1 hour. The associated reduction in rate of change in concentration can be by a factor of about 0.05, 0.10, 0.25, 0.5 or at least 0.8. In certain embodiments, this is accomplished by releasing less than about 30%, 50%, 75%, 90%, or 95% of the one or more cofactors into the circulation within one hour of such administration.

Optionally, the controlled release formulations exhibit plasma concentration curves having initial (e.g., from 2 hours after administration to 4 hours after administration) slopes less than 75%, 50%, 40%, 30%, 20% or 10% of those for an immediate release formulation of the same dosage of the same cofactor.

In some embodiments, the rate of release of the cofactor as measured in dissolution studies is less than about 80%, 70%, 60% 50%, 40%, 30%, 20%, or 10% of the rate for an immediate release formulation of the same cofactor over the first 1, 2, 4, 6, 8, 10, or 12 hours.

The controlled release formulations provided herein can adopt a variety of formats. In some embodiments, the formulation is in an oral dosage form, including liquid dosage forms (e.g., a suspension or slurry), and oral solid dosage forms (e.g., a tablet or bulk powder), such as, but not limited to those, those described herein.

The controlled release tablet of a formulation disclosed herein can be of a matrix, reservoir or osmotic system. Although any of the three systems is suitable, the latter two systems can have more optimal capacity for encapsulating a relatively large mass, such as for the inclusion of a large amount of a single cofactor, or for inclusion of a plurality of cofactors, depending on the genetic makeup of the individual. In some embodiments, the slow-release tablet is based on a reservoir system, wherein the core containing the one or more cofactors is encapsulated by a porous membrane coating which, upon hydration, permits the one or more cofactors to diffuse through. Because the combined mass of the effective ingredients is generally in gram quantity, an efficient delivery system can provide optimal results.

Thus, tablets or pills can also be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol and cellulose acetate. In some embodiments, a formulation comprising a plurality of cofactors can have different cofactors released at different rates or at different times. For example, there can be additional layers of cofactors interspersed with enteric layers.

Methods of making sustained release tablets are known in the art, e.g., see U.S. Patent Publications 2006/051416 and 2007/0065512, or other references disclosed herein. Methods such as described in U.S. Pat. Nos. 4,606,909, 4,769,027, 4,897,268, and 5,395,626 can be used to prepare sustained release formulations of the one or more cofactors determined by the genetic makeup of an individual. In some embodiments, the formulation is prepared using OROS® technology, such as described in U.S. Pat. Nos. 6,919,373, 6,923,800, 6,929,803, and 6,939,556. Other methods, such as described in U.S. Pat. Nos. 6,797,283, 6,764,697, and 6,635,268, can also be used to prepare the formulations disclosed herein.

In some embodiments, the compositions can be formulated in a food composition. For example, the compositions can be a beverage or other liquids, solid food, semi-solid food, with or without a food carrier. For example, the compositions can include a black tea supplemented with any of the compositions described herein. The composition can be a dairy product supplemented any of the compositions described herein. In some embodiments, the compositions can be formulated in a food composition. For example, the compositions can comprise a beverage, solid food, semi-solid food, or a food carrier.

In some embodiments, liquid food carriers, such as in the form of beverages, such as supplemented juices, coffees, teas, sodas, flavored waters, and the like can be used. For example, the beverage can comprise the formulation as well as a liquid component, such as various deodorant or natural carbohydrates present in conventional beverages. Examples of natural carbohydrates include, but are not limited to, monosaccharides such as, glucose and fructose; disaccharides such as maltose and sucrose; conventional sugars, such as dextrin and cyclodextrin; and sugar alcohols, such as xylitol and erythritol. Natural deodorant such as taumatin, *stevia* extract, levaudioside A, glycyrrhizin, and synthetic deodorant such as saccharin and aspartame can also be used. Agents such as flavoring agents, coloring agents, and others can also be used. For example, pectic acid and the salt thereof, alginic acid and the salt thereof, organic acid, protective colloidal adhesive, pH controlling agent, stabilizer, a preservative, glycerin, alcohol, or carbonizing agents can also be used. Fruit and vegetables can also be used in preparing foods or beverages comprising the formulations discussed herein.

Alternatively, the compositions can be a snack bar supplemented with any of the compositions described herein. For example, the snack bar can be a chocolate bar, a granola bar, or a trail mix bar. In yet another embodiment, the present dietary supplement or food compositions are formulated to have suitable and desirable taste, texture, and viscosity for consumption. Any suitable food carrier can be used in the present food compositions. Food carriers of the present invention include practically any food product. Examples of such food carriers include, but are not limited to food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables. In an embodiment, food carriers employed herein can mask the undesirable taste (e.g., bitterness). Where desired, the food composition presented herein exhibit more desirable textures and aromas than that of any of the components described herein. For example, liquid food carriers can be used according to the invention to obtain the present food compositions in the form of beverages, such as supplemented juices, coffees, teas, and the like. In other embodiments, solid food carriers can be used according to the invention to obtain the present food compositions in the form of meal replacements, such as supplemented snack bars, pasta, breads, and the like. In yet other embodiments, semi-solid food carriers can be used according to the invention to obtain the present food compositions in the form of gums, chewy candies or snacks, and the like.

The dosing of the combination compositions can be administered about, less than about, or more than about 1, 2, 3, 4, 5, 6, 7, 8, 9, 10 or more times a daily. A subject can receive dosing for a period of about, less than about, or greater than about 1, 2, 3, 4, 5, 6, 7, 8, 9, 10, 11, 12, 13, 14 or more days, weeks or months. A unit dose can be a fraction of the daily dose, such as the daily dose divided by the number of unit doses to be administered per day. A unit dose can be a fraction of the daily dose that is the daily dose divided by the number of unit doses to be administered per day and further divided by the number of unit doses (e.g. tablets) per administration. The number of unit doses per administration can be about, less than about, or more than about 1, 2, 3, 4, 5, 6, 7, 8, 9, 10, or more. The number of doses per day can be about, less than about, or more than about 1, 2, 3, 4, 5, 6, 7, 8, 9, 10, or more. The number of unit doses per day can be determined by dividing the daily dose by the unit dose, and can be about, less than about, or more than about 1, 2, 3, 4, 5, 6, 7, 8, 9, 10, 11, 12, 13, 14, 15, 6, 17, 18, 19, 20, or more unit doses per day. For example, a unit dose can be about ½, ⅓, ¼, ⅕, ⅙, ⅐, ⅛, ⅑, ⅒. A unit dose can be about one-third of the daily amount and administered to the subject three times daily. A unit dose can be about one-half of the daily amount and administered to the subject twice daily. A unit dose can be about one-fourth of the daily amount with two unit doses administered to the subject twice daily. In some embodiments, a unit dose comprises about, less than about, or more than about 50 mg resveratrol. In some embodiments, a unit dose comprises about, less than about, or more than about 550 mg leucine. In some embodiments, a unit dose comprises about, less than about, or more than about 200 mg of one or more leucine metabolites.

In some embodiments, a unit dose (e.g. a unit dose comprising one or more leucine metabolites, such as HMB) is administered as one unit dose two times per day. A unit dose can comprise more than one capsule, tablet, vial, or entity.

Compositions disclosed herein can further comprise a flavorant and can be a solid, liquid, gel or emulsion.

When the subject composition administered further comprises one or more therapeutic agents, and the therapeutic agents have a shorter half-life than the leucine and/or leucine metabolites, or the nicotinic acid and/or nicotinamide riboside and/or nicotinic acid metabolites, the unit dose forms of the therapeutic agent and the leucine and/or leucine metabolites, or nicotinic acid and/or nicotinamide riboside and/or nicotinic acid metabolites can be adjusted accordingly.

Methods

The subject composition is particularly useful for ameliorating a hyperlipidemic condition. In one embodiment, the invention provides for methods for reducing total lipid content or lowering level of total cholesterol, LDL, or triglyceride, increasing HDL level, or reducing atherosclerotic plaque size comprising administering to a subject in need thereof any of the subject compositions. The level or content described herein can be a circulating concentration in serum or blood stream, or a total amount in the subject's body. In some embodiments, the subject composition is useful in increasing weight loss of the subject, and increase sirt1 activation or fat oxidation of the subject. In various embodiments of the invention, a composition is administered to the subject in an amount that delivers synergizing amounts of leucine and/or a metabolite thereof, nicotinic acid and/or nicotinamide riboside and/or a nicotinic acid metabolite, and/or resveratrol sufficient to ameliorate a hyperlipidemic condition of the subject. In some embodiments, nicotinic acid, nicotinamide riboside or nicotinic acid metabolites can induce a side effect (e.g., cutaneous vasodilation) if it is administered to a subject at its therapeutic dose without leucine or leucine metabolites. Methods described herein can also be useful for ameliorating the side-effect without losing the therapeutic effectiveness of nicotinic acid, nicotinamide riboside or nicotinic acid metabolites. A description of various aspects, features, embodiments, and examples, is provided herein.

The subject methods comprising the use of leucine and/or leucine metabolite with nicotinic acid and/or nicotinamide riboside and/or nicotinic acid metabolites can be applicable for administering to a subject that is suffering from hyperlipidemia, at risk of suffering from hyperlipidemia, and/or suffering from a condition that is associated with hyperlipidemia such as cardiovascular conditions. In some cases, an effective amount of an additional therapeutic or a pharmaceutically active agent that is known in the medical art (e.g., an anti-hyperlipidemic agent) can be administered to a subject in conjunction with any of the subject compositions.

Hyperlipidemia can be characterized by a high level of total lipid content or level in a subject. Hyperlipidemia can also be characterized by a high level of body weight or BMI of a subject. The types of lipid can include cholesterol, cholesterol esters, phospholipids and triglycerides. The content or level of the lipids can be a circulating level that is measured in the bloodstream, plasma or serum of the subject. The content of the lipids can also be correlated by the body weight of the subject. These lipids can be transported in the blood as large lipoproteins including chylomicrons, very low-density lipoproteins (VLDL), intermediate-density lipoprotein (IDL), low-density lipoproteins (LDL) and high-density lipoproteins (HDL) based on their density. Most triglycerides can be transported in chylomicrons or VLDL and most cholesterol can be carried in LDL and HDL. High levels of lipid in the circulation can cause lipid accumulation on the walls of arteries, and further result in atherosclerotic plaque formation and therefore narrow the arteries. The subject that is suffering from hyperlipidemia can be at high risk of acquiring a cardiovascular condition. Hyperlipidemia can also be characterized by a high level of some lipoproteins or a low level of HDL. The condition that the subject is suffering from or at risk of suffering from can be a condition that is associated with an abnormal level of lipoproteins or lipids in the subject. The subject composition can be used to change the level of the one or more lipids or lipoproteins in the subject. In some embodiments, the type of lipids or lipoproteins that its level can be affected by the subject compositions and methods can be one or more lipoproteins and/or lipids including but not limited to: total cholesterol, triglyceride, HDL, IDL, VLDL or LDL.

A number of methods can be used to assess the levels of lipoproteins and/or lipids in a subject. These methods can differ from one another in the type of sample and the analytical technique used. The type of sample that can be used to measure such levels include but are not limited to: serum, plasma, whole blood, red blood cells or tissue samples. Where desired, the level of lipoproteins and/or lipids can be measured under a fasting condition, e.g., without taking food for at least about 8 hours, 10 hours, 12 hours, 15 hours, 24 hours, or even longer.

The size of atherosclerotic plaque or lesion can be measured by any methods that are known in the art. For examples, methods described in Phan B A et al., "Effects of niacin on glucose levels, coronary stenosis progression, and clinical events in subjects with normal baseline glucose levels (100 mg/dl): a combined analysis of the Familial Atherosclerosis Treatment Study (FATS), HDL-Atherosclerosis Treatment Study (HATS), Armed Forces Regression Study (AFREGS), and Carotid Plaque Composition by MRI during lipid-lowering (CPC) study", Am J Cardiol. 2013 Feb. 1; 111(3):352-5, and Lehman S J et al., "Assessment of Coronary Plaque Progression in Coronary CT Angiography Using a Semi-Quantitative Score", JACC Cardiovasc Imaging. 2009 November; 2(11): 1262-1270. Non-limiting example of the method to measure the size of atherosclerotic plaque or lesion can be quantitative coronary angiography.

In some embodiments, the amounts of the nicotinic acid, nicotinamide riboside and/or nicotinic acid metabolites in the composition, if administered to a subject alone and without leucine, a leucine metabolite, or resveratrol, can cause no therapeutic effect in the subject. Additionally, the amounts of leucine, a leucine metabolite, or resveratrol, if administered to the subject without the nicotinic acid, nicotinamide riboside or nicotinic acid metabolites, can have no therapeutic effect on the subject. However, when the nicotinic acid, nicotinamide riboside and/or nicotinic acid metabolites is administered in conjunction with either leucine, a leucine metabolite, or resveratrol, a therapeutic effect can be observed. The "therapeutic effect" described herein is a lowered total lipid content, decreased total cholesterol level, decreased triglyceride level, increased HDL level, decreased LDL level or reduced atherosclerotic plaque in the subject administered. Accordingly, the invention provides a method for administering a composition comprising (a) leucine and/or one or more metabolites thereof and (b) nicotinic acid and/or nicotinamide riboside and/or nicotinic acid metabolites present in a sub-therapeutic amount, wherein the composition is effective in increasing treating hyperlipidemic conditions as compared to that of component (b) when it is used alone. The amount of leucine in the composition can also be a sub-therapeutic amount.

Quantification of the therapeutic effect can show that the effect of a composition that comprises (a) leucine or a leucine metabolite and (b) a sub-therapeutic amount of nicotinic acid, nicotinamide riboside or a nicotinic acid metabolite is greater than the predicted effect of administering (a) or (b) alone, assuming simple additive effects of (a) and (b), and thus the effect is synergistic. The synergistic effect can be quantified as the measured effect above the predicted simple additive effect of the components of the composition. For example, if administration of component (a) alone yields an effect of 10% relative to control, administration of component (b) alone yields an effect of 15% relative to control, and administration of a composition comprising both (a) and (b) yields an effect of 60% relative to control, the synergistic effect would be 60%-(15%+10%), or 35%.

In some embodiments, a therapeutic amount of nicotinic acid, nicotinamide riboside and/or nicotinic acid metabolites can cause a side effect that can be characterized by an increased in cutaneous vasodilation. The increase in the cutaneous vasodilation can be clinically significant. A sub-therapeutic amount of nicotinic acid, nicotinamide riboside and/or nicotinic acid metabolites cannot cause a clinically significant cutaneous vasodilation, or can reduce the degree of cutaneous vasodilation in the subject administered as compared to a therapeutic amount of nicotinic acid, nicotinamide riboside and/or nicotinic acid metabolites. The subject compositions and methods described herein comprise a sub-therapeutic amount of nicotinic acid, nicotinamide riboside and/or nicotinic acid metabolites, to be used with leucine and/or leucine metabolites to result a therapeutic degree of effect of the sub-therapeutic amount of the nicotinic acid, nicotinamide riboside and/or nicotinic acid metabolites without causing the degree of side effect that can normally be caused by a therapeutic amount of nicotinic acid, nicotinamide riboside and/or nicotinic acid metabolites when used without leucine and/or leucine metabolites. Levels of cutaneous vasodilation can be measured by any methods known in the medical art, such as the methods including laser-Doppler flowmeter. With the same level of therapeutic effect (e.g. lowering cholesterol level by at least 5%), the level of cutaneous vasodilation caused by the subject compositions as compared to nicotinic acid, nicotinamide riboside and/or nicotinic acid metabolites without leucine and/or leucine metabolites can be lower. For example, less than about 1%, 5%, 10%, 15%, 20%, 25%, 30%, 35%, 40%, 45%, 50%, 60%, 70%, 80% or 90% of the level that is caused by a therapeutic amount of to nicotinic acid, nicotinamide riboside and/or nicotinic acid metabolites.

The amount of leucine and/or leucine metabolites can be at least about 25, 50, 75, 100, 150, 200, 250, 300, 350, 400, 450, 500 mg. The sub-therapeutic amount of nicotinic acid, nicotinamide riboside, and/or nicotinic acid metabolites can be less than 1 g, 500, 250, 100, 50 or 10 mg. The amount of nicotinic acid, nicotinamide riboside, and/or nicotinic acid metabolites can be between about 1-100 mg. The amount of nicotinic acid, nicotinamide riboside, and/or nicotinic acid metabolites can be capable of achieving a circulating level of nicotinic acid, nicotinamide riboside, and/or nicotinic acid metabolites that is about 1-100 nM, higher than about 100 nM or at least about 10 nM.

Accordingly, the multi-component compositions described herein (such as nicotinic acid/leucine, nicotinic acid/leucine/resveratrol, nicotinamide riboside/leucine, and nicotinamide riboside/leucine/resveratrol) can have a beneficial or synergistic effect on lowering total lipid content, decreasing total cholesterol level, decreasing triglyceride level, increasing HDL level, and/or decreasing LDL level. In some embodiments, the compositions and methods described herein can be effective to change the level of lipoproteins and/or lipids in the subject by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% or even higher as compared to an initial level of lipoproteins and/or lipids prior to administration of it to a subject. The level can be lowered by about 19%-24%, 14%-29%, 12%-35%, 10-40%, 8%-45%, 5%-50%, 2%-60%, or 1%-70%. The level can be a circulating level.

In some embodiments, the compositions and methods described herein can be effective to reduce the atherosclerotic plaque size in a subject by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% or even higher as compared to an initial size of atherosclerotic plaque prior to administration of it to a subject. The level can be reduced by about 19%-24%, 14%-29%, 12%-35%, 10-40%, 8%-45%, 5%-50%, 2%-60%, or 1%-70%.

Administration of compositions disclosed herein that increase SIRT1 and SIRT3 activity can be useful in any subject in need of metabolic activation of hepatocytes, adipocytes or one or more of their muscles, e.g., skeletal muscle, smooth muscle or cardiac muscle or muscle cells thereof. A subject can be a subject having cachexia or muscle wasting. Increasing SIRT3 activity can also be used to increase or maintain body temperature, e.g., in hypothermic subjects and increasing SIRT1 activity is beneficial for treating hyperlipidemia, diabetes (type 2 diabetes) and impaired glucose tolerance and reducing inflammatory responses in a subject. Increase in metabolic activation of hepatocytes, adipocytes or one or more of their muscles can be useful in lowering the lipid content and increasing weight loss of the subject. The content or levels of the lipids and lipoproteins can be lowered.

Increasing SIRT3 activity can also be used for treating or preventing hyperlipidemia, cardiovascular diseases, reducing blood pressure by vasodilation, increasing cardiovascular health, and increasing the contractile function of vascular tissues, e.g., blood vessels and arteries (e.g., by affecting smooth muscles). Generally, activation of SIRT3 can be used to stimulate the metabolism of hepatocytes, adipocytes or any type of muscle, e.g., muscles of the gut or digestive system, or the urinary tract, and thereby can be used to control gut motility, e.g., constipation, and incontinence. SIRT3 activation can also be useful in erectile dysfunction. It can also be used to stimulate sperm motility, e.g., and be used as a fertility drug. Other embodiments in which it would be useful to increase SIRT3 include repair of muscle, such as after a surgery or an accident, increase of muscle mass; and increase of athletic performance.

Thus the invention provides methods in which beneficial effects are produced by ingestion of nicotinic acid and/or nicotinamide riboside and/or any metabolites thereof, along with leucine and/or leucine metabolites that increase the protein or activity level of SIRT1 or SIRT3. The activity of SIRT1 and SIRT3 can be increased in muscle cells and/or hepatocytes in the subject. These methods effectively facilitate, increase or stimulate one or more of the following: mimic the benefits of calorie restriction or exercise in the hepatocyte or muscle cells, increase mitochondrial biogenesis or metabolism, increase mitochondrial activity and/or endurance in the hepatocytes or muscle cells, sensitize the muscle cells to insulin, increase fatty acid oxidation in the muscle cell, decrease reactive oxygen species (ROS) in the muscle cell, increase PGC-1α and/or UCP3 and/or GLUT4 expression in the hepatocytes or muscle cells, and activate AMP activated protein kinase (AMPK) in the hepatocytes or muscle cells. Various types of muscle cells can be contacted in accordance with the invention. In some embodiments, the muscle cell is a skeletal muscle cell. In certain embodiments, the muscle cell is a cell of a slow-twitch muscle, such as a soleus muscle cell.

The compositions can be administered to a subject orally or by any other methods. Methods of oral administration include administering the composition as a liquid, a solid, or a semi-solid that can be taken in the form of a dietary supplement or a food stuff.

The compositions can be administered periodically. For example, the compositions can be administered one, two, three, four times a day, or even more frequent. The subject can be administered every 1, 2, 3, 4, 5, 6 or 7 days. In some embodiments, the compositions are administered three times daily. The administration can be concurrent with meal time of a subject. The period of treatment or diet supplementation can be for about 1, 2, 3, 4, 5, 6, 7, 8, or 9 days, 2 weeks, 1-11 months, or 1 year, 2 years, 3, years, 4 years, 5 years or even longer. In some embodiments of the invention, the dosages that are administered to a subject can change or remain constant over the period of treatment. For example, the daily dosing amounts can increase or decrease over the period of administration.

The length of the period of administration and/or the dosing amounts can be determined by a physician or any other type of clinician. The physician or clinician can observe the subject's response to the administered compositions and adjust the dosing based on the subject's performance. For example, dosing for subjects that show reduced effects in energy regulation can be increased to achieve desired results.

In some embodiments, the components in the compositions can be administered together at the same time in the same route, or administered separately. The components in the compositions can also be administered subsequently. In some embodiments, leucine and/or leucine metabolites in the compositions can be administered to a subject in conjunction with nicotinic acid, nicotinamide riboside and/or nicotinic acid metabolites. In some embodiments, the components in the compositions can be administered at the same or different administration route. For example, leucine and/or or leucine metabolites can be administered orally while nicotinic acid, nicotinamide riboside and/or nicotinic acid metabolites can be administered via intravenous injection. Each of the metabolites can be administered via the same or different administration routes.

In some embodiments, the composition ns administered to a subject can be optimized for a given subject. For example, the ratio of leucine and/or leucine metabolites to nicotinic acid, nicotinamide riboside and/or nicotinic acid metabolites or the particular components in a combination composition can be adjusted. The ratio and/or particular components can be selected after evaluation of the subject after being administered one or more compositions with varying ratios of leucine and/or leucine metabolites to nicotinic acid, nicotinamide riboside and/or nicotinic acid metabolites or varying combination composition components.

Another aspect of the invention provides for achieving desired effects in one or more subjects after administration of a combination composition described herein for a specified time period. For example, the beneficial effects of the compositions described herein can be observed after administration of the compositions to the subject for 1, 2, 3, 4, 6, 8, 10, 12, 24, or 52 weeks.

The invention provides for a method of treating subjects, comprising identifying a pool of subjects amenable to treatment. The identifying step can include one or more screening tests or assays. For example, subjects that are identified as hyperlipidemic, or that have above average or significantly greater than average body mass indices (BMI) and/or weight can be selected for treatment. The subject can be overweight or obese, which can be indicated by an above ideal body weight of the subject or a BMI that is higher than 25, 30, 40, or 50. The subject can weight more than about 50, 75, 100, 125, 150, 160, 170, 180, 190, 200, 210, 220, 230, 240, 250, 260, 270, 280, 290, 300, 310, 320, 330, 340, 350, 360, 370, 380, 390, or 400 lbs. The subjects that have been on a high fat diet can be selected for treatment as well. The identified subjects can then be treated with one or more compositions described herein. For example, they can be treated with a combination composition comprising nicotinic acid and a branched-chain amino acid.

The invention also provides for methods of manufacturing the compositions described herein. In some embodiments, the manufacture of a composition described herein comprises mixing or combining two or more components. These components can include nicotinic acid, nicotinamide riboside and/or nicotinic acid metabolites, and leucine or metabolites thereof (such as HMB, or KIC). The amount or ratio of components can be that as described herein. For example, the mass ratio of leucine compared with resveratrol can be greater than about 80.

In some embodiments, the compositions can be combined or mixed with a pharmaceutically active or therapeutic agent, a carrier, and/or an excipient. Examples of such components are described herein. The combined compositions can be formed into a unit dosage as tablets, capsules, gel capsules, slow-release tablets, or the like.

In some embodiments, the composition is prepared such that a solid composition containing a substantially homogeneous mixture of the one or more components is achieved, such that the one or more components are dispersed evenly throughout the composition so that the composition can be readily subdivided into equally effective unit dosage forms such as tablets, pills and capsules.

Kits

The invention also provides kits. The kits include one or more compositions described herein, in suitable packaging, and can further comprise written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information can be based on the results of various studies, for example, studies using experimental animals involving in vivo models and studies based on human clinical trials. A kit can comprise one or more unit doses described herein. In some embodiments, a kit comprises about, less than about, or more than about 1, 2, 3, 4, 5, 6, 7, 8, 9, 10, 11, 12, 13, 14, 15, 16, 17, 18, 19, 20, 30, 31, 60, 90, 120, 150, 180, 210, or more unit doses. Instructions for use can comprise dosing instructions, such as instructions to take 1, 2, 3, 4, 5, 6, 7, 8, 9, 10, or more unit doses 1, 2, 3, 4, 5, 6, 7, 8, 9, 10, or more times per day. For example, a kit can comprise a unit dose supplied as a tablet, with each tablet package separately, multiples of tablets packaged separately according to the number of unit doses per administration (e.g. pairs of tablets), or all tablets packaged together (e.g. in a bottle). As a further example, a kit can comprise a unit dose supplied as a bottled drink, the kit comprising 1, 2, 3, 4, 5, 6, 7, 8, 9, 10, 11, 12, 13, 14, 24, 28, 36, 48, 72, or more bottles.

The kit can further contain another agent. In some embodiments, the compound of the present invention and the agent are provided or packaged as separate compositions in separate containers within the kit. In some embodiments, the compound of the present invention and the agent are provided or packaged as a single composition within a container in the kit. Suitable packaging and additional articles for use (e.g., measuring cup for liquid preparations, foil wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

In some embodiments, a kit can comprise a multi-day supply of unit dosages. The unit dosages can be any unit dosage described herein. The kit can comprise instructions directing the administration of the multi-day supply of unit dosages over a period of multiple days. The multi-day supply can be a one-month supply, a 30-day supply, or a multi-week supply. The multi-day supply can be a 90-day, 180-day, 3-month or 6-month supply. The kit can include packaged daily unit dosages, such as packages of 1, 2, 3, 4, or 5 unit dosages. The kit can be packaged with other dietary supplements, vitamins, and meal replacement bars, mixes, and beverages.

EXAMPLES

Example 1

Effects of Nicotinic Acid/Leucine and Nicotinic Acid/Leucine/Resveratrol on Sirt1 Level in Muscle Cells In Vitro The use of a composition comprising nicotinic acid and leucine as described herein was investigated, wherein the composition comprises free leucine and a sub-therapeutic amount of nicotinic acid. The composition activated Sirt1 in the muscle cells and can be used to ameliorate a hyperlipidemic condition. A composition further comprises resveratrol was investigated as well.

C2C12 mouse myoblasts (American Type Culture Collection) were plated at a density of 8000 cells/cm$^2$ (10 cm$^2$ dish) and grown in Dulbecco's modified eagle's medium (DMEM) containing 10% fetal bovine serum (FBS), and antibiotics (growth medium) at 37° C. in 5% CO2. For differentiation of C2C12 cells, cells were grown to 100% confluence, transferred to differentiation medium (DMEM with 2% horse serum and 1% penicillin-streptomycin), and fed with fresh differentiation medium every day until myotubes were fully formed (3 days).

A dose-response study was performed by administering the cells with different concentrations of nicotinic acid in order to find the sub-therapeutic amount of nicotinic acid that exerts no effect on the variable studied. Concentrations of nicotinic acid <100 nM alone were found to exert no effect, and experimental concentrations were therefore set below this level, at 10 nM. This sub-therapeutic level of nicotinic acid was then tested in combination with leucine and HMB. The leucine and HMB were at concentrations that have been previously shown to be attainable in diet or supplement while each having no therapeutic effect on these variables when administered alone (0.5 mM for leucine and 5 μM for HMB).

C2C12 cell myotubes were administered with 10 nM nicotinic acid (NA), 10 nM nicotinic acid with 0.5 mM leucine (NA/Leu), 10 nM nicotinic acid with 0.5 mM leucine and 200 nM resveratrol (NA/R/Leu), 200 nM resveratrol and 0.5 mM leucine (R/Leu), and 10 μM nicotinic acid for 24 hours.

Western blotting was performed with SIRT1 antibodies that were obtained from Cell Signaling (Danvers, Mass.). Protein was measured by BCA kit (Thermo Scientific). Total 35 μg of protein from the cell lysate was resolved on 10% Tris/HCL polyacrylamide gels (Criterion precast gel, Bio-Rad Laboratories, Hercules, Calif.), transferred to PVDF membranes, incubated in blocking buffer (3% BSA in TBS), incubated with primary antibody, washed and incubated with secondary horseradish peroxidase-conjugated antibody. Visualization and chemiluminescent detection were conducted using BioRad ChemiDoc instrumentation and software (Bio-Rad Laboratories, Hercules, Calif.). The band intensity was assessed using Image Lab 4.0 (Bio-Rad Laboratories, Hercules, Calif.), with correction for background and loading controls. Sirt1 was detected at 104-115 kDA. Data were analyzed via one-way analysis of variance and least significant difference test was used to separate significantly different group means.

Figure 1:
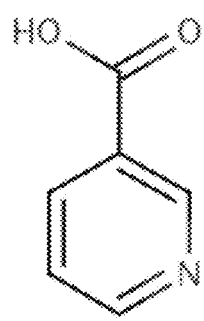
FIG. 1 illustrates the chemical structures of nicotinic acid and nicotinamide riboside.
Figure 1:
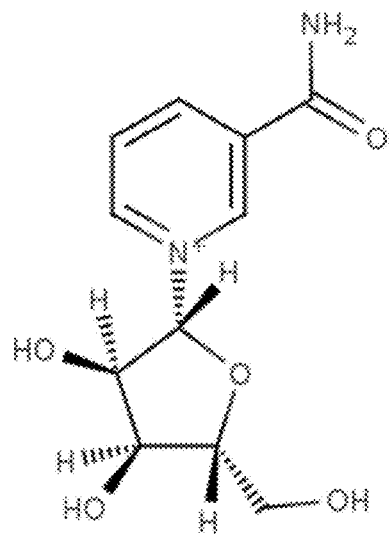
Figure 2:
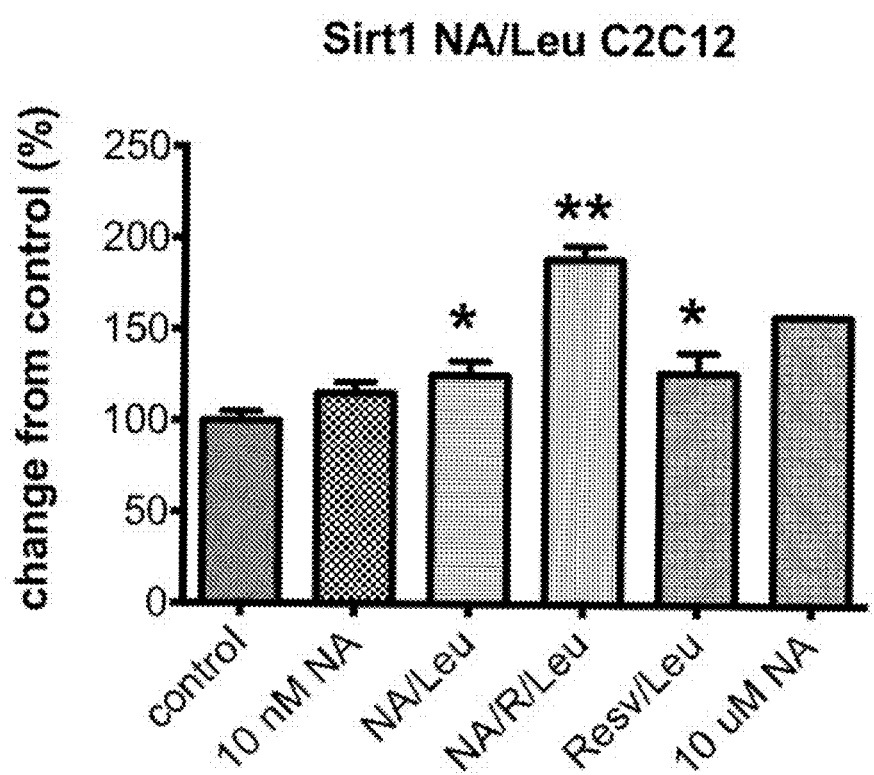
FIG. 2 illustrates the effects of nicotinic acid and leucine, and/or resveratrol on Sirt1 activation in C2C12 myotubes. NA refers to nicotinic acid; Leu refers to leucine; R refers to resveratrol. $*p<0.05$; $**p=0.0001$. Data expressed as % change from control value.

It was found that nicotinic acid-leucine synergistically stimulates Sirt1 in C2C12 myotubes, with an effect comparable to resveratrol-leucine (FIG. 2, p<0.05). Nicotinic acid alone did not have a significant effect on Sirt1 levels. The three-way combination of leucine (10 nM)/resveratrol (200 nM) and nicotinic acid (10 nM) exerted markedly greater effects, with a 200% increase in Sirt1 levels (p=0.0001).

Example 2

Effects of Nicotinic Acid/Leucine and Nicotinic Acid/Leucine/Resveratrol on P-AMPK/AMPK Level in Fat Cells In Vitro The use of a composition comprising nicotinic acid and leucine as described herein was investigated, wherein the composition comprises free leucine and a sub-therapeutic amount of nicotinic acid. The composition increased sirtuin pathway output including AMPK, a signaling molecule in the sirtuin pathway, and p-AMPK/AMPK level in the fat cells and can be used to ameliorate a hyperlipidemic condition. A composition further comprises resveratrol was investigated as well.

3T3-L1 preadipocytes (American Type Culture Collection) were plated at a density of 8000 cells/cm2 (10 cm2 dish) and grown in Dulbecco's modified eagle's medium (DMEM) containing 10% fetal bovine serum (FBS), and antibiotics (growth medium) at 37° C. in 5% CO2. Confluent 3T3-L1 preadipocytes were induced to differentiate into adipocytes with a standard differentiation medium consisting of DMEM medium supplemented with 10% FBS, 250 nM dexamethasone, 0.5 mM 3-Isobutyl-1-methylxanthine (IBMX) and 1% penicillin-streptomycin. Preadipocytes were maintained in this differentiation medium for 3 days and subsequently cultured in growth medium. Cultures were re-fed every 2-3 days to allow >90% cells to reach fully differentiation before conducting chemical treatment.

A dose-response study was performed by administering the cells with different concentrations of nicotinic acid in order to find the sub-therapeutic amount of nicotinic acid that exerts no effect on the variable studied. Concentrations of nicotinic acid <100 nM alone were found to exert no effect, and experimental concentrations were therefore set below this level, at 10 nM. This sub-therapeutic level of nicotinic acid was then tested in combination with leucine and HMB. The leucine and HMB were at concentrations that have been previously shown to be attainable in diet or supplement while each having no therapeutic effect on these variables when administered alone (0.5 mM for leucine and 5 µM for HMB).

Differentiated 3T3-L1 cells were administered with 10 nM nicotinic acid (NA), 10 nM nicotinic acid with 0.5 mM leucine (NA/Leu), 10 nM nicotinic acid with 0.5 mM leucine and 200 nM resveratrol (NA/R/Leu), 200 nM resveratrol and 0.5 mM leucine (R/Leu), and 10 µM nicotinic acid for 24 hours.

Western blotting was performed with antibodies against AMPK and Phospho-AMPKα (Thr172) obtained from Cell Signaling (Danvers, Mass.). Protein was measured by BCA kit (Thermo Scientific). Total 30 µg of protein from the cell lysate was resolved on 10% Tris/HCL polyacrylamide gels (Criterion precast gel, Bio-Rad Laboratories, Hercules, Calif.), transferred to PVDF membranes, incubated in blocking buffer (3% BSA in TBS), incubated with primary antibody (P-AMPK), washed and incubated with secondary horseradish peroxidase-conjugated antibody. Visualization and chemiluminescent detection were conducted using Bio-Rad ChemiDoc instrumentation and software (Bio-Rad Laboratories, Hercules, Calif.). The band intensity was assessed using Image Lab 4.0 (Bio-Rad Laboratories, Hercules, Calif.), with correction for background and loading controls. AMPK was detected 62 kDA and P-AMPK was detected at 64-66 kDA. Data were analyzed via one-way analysis of variance and least significant difference test was used to separate significantly different group means.

Figure 3:
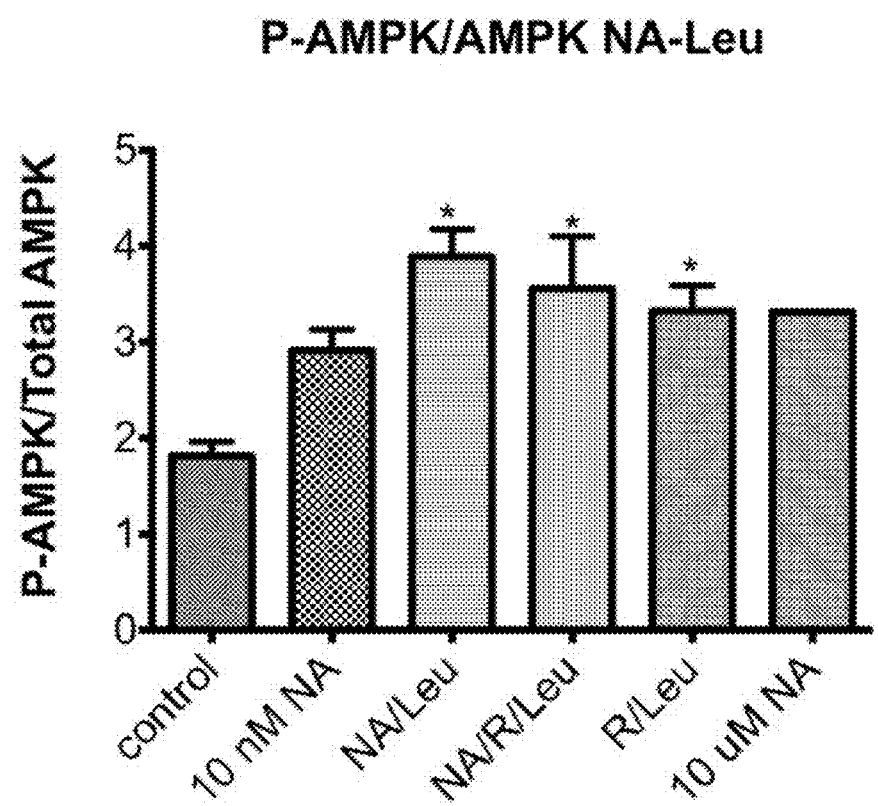
FIG. 3 illustrates the effects of nicotinic acid and leucine, and/or resveratrol on P-AMPK/AMPK ratio in 3T3-L1 adipocytes. NA refers to nicotinic acid; Leu refers to leucine; R refers to resveratrol. $*p<0.01$. Data expressed as % change from control value.

It was found that 10 nM nicotinic acid, when administered alone, had no significant effect on AMPK activation (FIG. 3). The combination of nicotinic acid-leucine significantly stimulated AMPK activation to comparable degree as leucine-resveratrol ($p<0.01$), as demonstrated by an increase in P-AMPK/AMPK, while the three-way combination of nicotinic acid-leucine-resveratrol was not significantly different from either of the two way leucine combinations (FIG. 2).

Example 3

Effects of Nicotinic Acid/Leucine and Nicotinic Acid/Leucine/Resveratrol on Fat Content in *C. elegans* In Vivo The use of a composition comprising (a) nicotinic acid and (b) leucine as described herein was investigated, wherein the composition comprises free leucine and a sub-therapeutic amount of nicotinic acid. The composition lowered lipid content in a subject after administration of the composition to the subject.

*Caenorhabditis elegans* (*C. elegans*) worms (N2 Bristol wild-type) were obtained from the *Caenorhabditis* Genetics Center (CGC) at the University of Minnesota and grown on standard NGM plates with *E. coli* (OP50) as food source at 20 degree C. For treatments, eggs were hatched on a starved plate overnight. Then synchronized L1 larvae were transferred to *E. coli* fed NGM plates containing indicated treatments for about 35 hours to reach L4/young adult stage. All treatments were added to the agar. Treatments included 10 nM of nicotinic acid and 0.5 mM of leucine.

Fat content, protein content, fatty acid oxidation of the *C. elegans* worm were measured using the methods described herein.

For Oil-Red Staining to quantify fat content, treated L4/young adult worms were washed off from plates three times with PBS and collected in a 15 ml conical tube, followed by centrifugation at 1000 g for 30 sec. The supernatant was discarded and the pellet was washed with 10 ml PBS. After centrifugation, the supernatant was discarded except 400 which was transferred to a new 1.5 ml eppendorf tube. Then 500 µl of 2×MRWB (160 mM KCl, 40 mM NaCl, 14 mM Na2EGTA, 1 mM Spermidine HCl, 0.4 mM Spermine, 30 mM NaPIPES pH 7.4, 0.2% β-Mercaptoethanol) and 100 µl of 20% Paraformaldehyde were added and the samples were gently rocked for 60 min at room temperature. Then tubes were centrifuged at 1500 g for 30 sec, then aspirated and washed with PBS once, centrifuged again and aspirated to 300 µl. 700 µl of isopropanol was added, mixed by inverting the tube and incubated with gentle shaking for 15 min at room temperature. After centrifuging the tubes to remove the isopropanol, 1 ml of 60% filtered Oil-Red-O-dye solution (0.5 g Oil Red O in 100 ml anhydrous isopropanol, equilibrated for 2 days by stirring at RT, then 4 vol ddH2O was mixed with 6 vol dye solution and equilibrated for 15 min at RT, then filtered with 0.2 M pore size) was added to worms and rotated on shaker overnight. Worms were centrifuged at 1200 g for 30 sec, and followed by ddH2O washes for 4 times to remove any unbound stain. For quantification, the Oil Red O was eluted from the cells by addition of 100% isopropanol and the optical density of 200 µl aliquots (triplicates/sample) was determined at a wavelength of 540 nm using a Biotek Synergy HT Microplate Reader (BioTek, Winooski, Vt., USA). Data were normalized to protein content using the Pierce BCA protein assay kit.

To determine the protein content by western blot, treated L4/young adult worms were washed off from plates with M9 buffer and collected into microcentrifuge tubes. After centrifugation (500 g for 5 min), supernatant was removed to about 100 µl. Then 250 µl RIPA buffer plus Protease and Phosphatase inhibitor mix was added. Samples were homogenized, then centrifuged at 16,000 g for 10 min at 40° C. The clear supernatant was used for further experiments. Protein content was determined using the Pierce BCA protein assay kit.

Fatty acid oxidation was measured by measuring the palmitate-stimulated oxygen consumption rate with the XF 24 analyzer (Seahorse Bioscience, Billerica, Mass., USA) as previously described (Bruckbauer A, Zemel MB. Synergistic effects of metformin, resveratrol, and hydroxymethylbutyrate on insulin sensitivity. Diabetes, Met Synd Obesity 2013; 6:93-102) with slight modifications. Treated L4/young adult worms were washed off from plates with M9 buffer and collected into 15 ml conical tubes. After centrifugation (1000 g for 1 min), supernatant was removed and worm pellet was diluted to a concentration of 40 worms/μl. Worms were kept in ice water during plating to limit movement, and 5 μl of the worm solution was added to each well of a 24-well Seahorse islet plates (~200 worms/well). Screens were inserted and 595 μl of M9 buffer with indicated treatments was added to each well. Each plate was cooled for 10 min before the start of the measurement. The temperature setting of the instrument was maintained at 29 degree C. during the experiment.

Data were analyzed via one-way analysis of variance and least significant difference test was used to separate significantly different group means.

Figure 4:
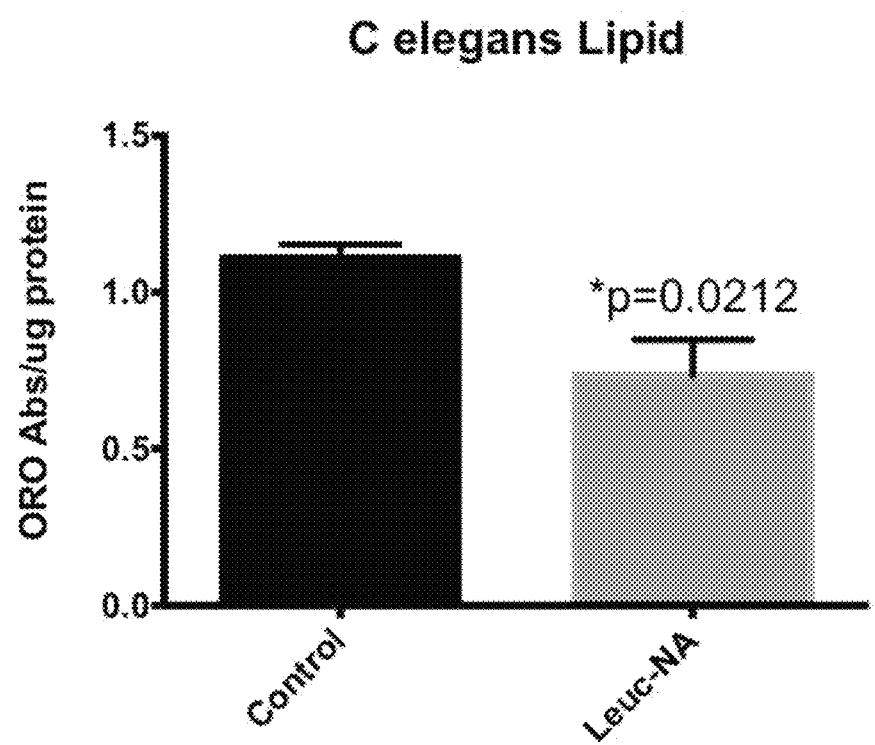
FIG. 4 illustrates the effects of leucine (0.5 mM)/nicotinic acid (10 nM) on lipid levels in C. elegans ($*p=0.012$). NA refers to nicotinic acid; Leu refers to leucine.

We measured the lipid content in C. elegans as shown in FIG. 4. It was found that exposing C. elegans to a leucine (0.5 mM)-nicotinic acid (10 nM) combination for 24 hours resulted in a 33% decrease in total lipid content compared to the non-treated control group.

Example 4

Effects of Nicotinic Acid/Leucine and Nicotinic Acid/Leucine/Resveratrol on Triglyceride, LDL, HDL and Cholesterol Levels, and Atherosclerotic Plaque Size In Vivo To assess the efficacy of the subject compounds, mice are administered the subject compounds comprising (a) nicotinic acid and/or nicotinamide riboside and/or nicotinic acid metabolites and (b) leucine and/or leucine metabolites as described herein, wherein the composition comprises free leucine and a sub-therapeutic amount of nicotinic acid. The composition can be used to lower triglyceride, LDL and cholesterol levels as well as to reduce the size of atherosclerotic plaque in a mouse after administration of the composition to the mouse. A composition further comprising resveratrol is investigated as well.

LDL receptor knockout (LDLRKO) mice are obtained from Jackson Laboratories (Bar Harbor, Me.), and housed in groups under room temperature in a humidity-controlled environment with a regular light and dark cycle. The mice are provided free access to an atherogenic diet containing 0.2% cholesterol (by weight) and 10% calories from saturated fat (palm oil) and water for 8 weeks prior to treatment. For treatment, the mice are given (a) 250 mg nicotinic acid/kg diet alone, (b) 250 mg of nicotinic acid/kg diet and 24 g of leucine/kg diet, (c) 50 mg nicotinic acid/kg diet, 24 g leucine/kg diet, and 12.5 mg resveratrol/kg diet, (d) 24 g leucine/kg diet and 12.5 mg resveratrol/kg diet, (e) 10 g nicotinic acid/kg diet alone The treatments are administered for 60 days continuously. Two control groups are included for comparison: the negative control group receives atherogenic diet with no treatment, and a double-negative control group receives a normal diet with no treatment. All chemicals are purchased from Sigma.

Blood samples of the mice in all groups are obtained from tails of the mice at day 7, 30 and 60 after the administration. The serum/plasma levels of triglyceride, cholesterol, LDL and HDL are measured. Cutaneous vasodilation is measured by laser-Doppler flowmeter. At day 60, mice are sacrificed for quantifying the aortic plaque. Briefly, after dissection and removal of adherent fat tissue, the aorta is immersed in the above buffer overnight. After removal of the adventitia, the aorta is opened longitudinally, pinned flat onto a dissecting wax, and stained with oil red 0 for microscopic image analysis. The total aortic area and stained aortic lesion area are manually outlined in a blinded fashion and analyzed using Adobe Photoshop CS3, and the lesion size as a percentage of the total aortic area is determined.

Results

Mice receiving only the atherogenic diet with no treatment can exhibit significantly higher levels of triglyceride, LDL and cholesterol in bloodstream as compared to the double negative control group receiving normal diet. For the treatment groups, group (a) can show similar, without statistically significant difference, levels of triglyceride, LDL, cholesterol and HDL as the negative control group receiving only atherogenic diet. Groups (b), (c) and (e) may exhibit significantly lower triglyceride, LDL and cholesterol levels, and significantly higher HDL level in the blood stream as compared to the negative control group receiving only atherogenic diet, and the levels may decrease (increase for HDL) over time. Group (d) may exhibit minimal decrease in triglyceride, LDL and cholesterol levels.

For atherosclerotic plaque, groups (b), (c) and (e) may exhibit significantly reduced atherosclerotic lesion size in all regions of the aorta. No significant reduction in atherosclerotic lesion size is expected in groups (a) and (d).

It is also expected that only the mice receiving 10 g of nicotinic acid/kg diet alone exhibit significant higher cutaneous vasodilation as compared to all the other groups including control groups. The cutaneous vasodilation may be found lower in the groups (a) to (d) as compared to group (e).

Overall, nicotinic acid with a dose that is 250 mg/kg diet administered in conjunction with 24 g leucine/kg diet may exhibit similar effects on lowering the triglyceride, LDL, and cholesterol level as well as increasing the HDL level in mice as compared to 10 g nicotinic acid/kg diet alone without increasing the cutaneous vasodilation significantly. Low dose of nicotinic acid administered in conjunction with leucine and resveratrol is expected to exhibit similar effects.

Example 5

Effects of Nicotinic Acid/Leucine and Nicotinic Acid/Leucine/Resveratrol on Triglyceride, LDL, HDL and Cholesterol Levels in Human To assess the efficacy of the subject compounds, humans are administered the subject compounds comprising (a) nicotinic acid and/or nicotinamide riboside and/or nicotinic acid metabolites and (b) leucine and/or leucine metabolites as described herein, wherein the composition comprises free leucine and a sub-therapeutic amount of nicotinic acid. The composition can be used to lower triglyceride, LDL and cholesterol levels in a human after administering the composition to the human. A composition further comprising resveratrol is investigated as well.

Patients that are pre-diagnosed with hyperlipidemia are admitted for the randomized and double blind study. Each patient is administered orally (a) 50 mg nicotinic acid alone, (b) 50 mg of nicotinic acid and 1135 mg of leucine, (c) 50 mg nicotinic acid, 1135 mg leucine, and 50 mg resveratrol, (d) 1135 mg leucine and 50 mg resveratrol, (e) 3000 mg nicotinic acid alone, and (f) placebo. The treatments are administered orally twice a day, for 60 days continuously.

Blood samples of the patients in all groups are obtained from at day 0, 30 and 60 after the administration. The serum/plasma levels of triglyceride, cholesterol, LDL and HDL are measured. Cutaneous vasodilation is measured by laser-Doppler flowmeter and the discomfort level described by the patients.

Results

For the treatment groups, group (a) and (f) may show similar, without statistically significant difference, levels of triglyceride, LDL, cholesterol and HDL as compared to day 0 values. Groups (b), (c) and (e) may exhibit significantly lower triglyceride, LDL and cholesterol levels, and significantly higher HDL level in the blood stream as compared to the respective day 0 values. Group (d) may exhibit minimal decrease in triglyceride, LDL and cholesterol levels.

It is also expected that only the patients receiving 3000 mg of nicotinic acid alone exhibit significant higher cutaneous vasodilation and more complaints from the patients as compared to all the other groups including placebo. The cutaneous vasodilation may be lower in the groups (a) to (d) as compared to group (e).

Overall, nicotinic acid with a dose that is 50 mg administered in conjunction with 1135 mg leucine may exhibit similar effects on lowering the triglyceride, LDL, and cholesterol level as well as increasing the HDL level in patients as compared to 3 g nicotinic acid alone without increasing the cutaneous vasodilation significantly. 50 mg of nicotinic acid+1135 mg leucine administered in conjunction with 50 mg resveratrol may exhibit similar effects.

Example 6

Effects of Nicotinic Acid/Leucine and Nicotinic Acid/Leucine/Resveratrol on Atherosclerotic Plaque Size in Human To assess the efficacy of the subject compounds, humans are administered the subject compounds as described herein, wherein the composition comprises free leucine and a sub-therapeutic amount of nicotinic acid. The composition can be used to reduce the size of atherosclerotic plaque in a human after administering the composition to the human. A composition further comprising resveratrol is investigated as well.

Patients that experience acute chest pain and are pre-diagnosed with hyperlipidemia are admitted for the randomized and double blind study. Each patient is administered orally (a) 50 mg nicotinic acid alone, (b) 50 mg of nicotinic acid and 1135 mg of leucine, (c) 50 mg nicotinic acid, 1135 mg leucine, and 50 mg resveratrol, (d) 1135 mg leucine and 50 mg resveratrol, and (e) placebo. The treatments are administered orally twice a day, for 3 years continuously. The size of atherosclerotic plaque is measured at day 0, months 6, 12, 18, 24, 30 and 36 by quantitative coronary angiography.

Results

For the treatment groups, group (a) and (e) may show similar, without statistically significant difference, size of atherosclerotic lesion as compared to day 0 values. Groups (b) and (c) may exhibit significantly reduced atherosclerotic plaque size as compared to the respective day 0 values. Group (d) may exhibit minimal decrease in atherosclerotic plaque size.

Example 7

Effects of Nicotinic Acid/Leucine on Triglyceride, LDL, HDL and Cholesterol Levels In Vivo To assess the efficacy of the subject compounds, mice were administered the subject compounds comprising (a) nicotinic acid and (b) leucine as described herein, wherein the composition comprises free leucine and a sub-therapeutic amount of nicotinic acid. The composition lowered the triglyceride, LDL and cholesterol levels in a mouse after administration of the composition to the mouse.

LDL receptor knockout (LDLRKO) mice were obtained from Jackson Laboratories (Bar Harbor, Me.), and housed in groups under room temperature in a humidity-controlled environment with a regular light and dark cycle. The mice were provided free access to an atherogenic western diet (WD) containing 0.21% cholesterol (by weight) and 40% calories from fat and water for 4 weeks prior to treatment. For treatment, the mice were given (a) the WD diet alone, (b) WD and 24 g of leucine/kg diet, (c) WD and 24 g of leucine/kg diet and 50 mg nicotinic acid/kg diet, (d) WD and 24 g of leucine/kg diet and 250 mg nicotinic acid/kg diet, or (e) WD and 1000 mg nicotinic acid/kg diet; this is approximately equivalent to a low therapeutic dose of nicotinic acid in hypercholesterolemic humans (1,500 mg/day). The treatments were administered for eight weeks continuously.

Blood samples of the mice in all groups were obtained from tails of the mice at following four and eight weeks of administration. The serum/plasma levels of triglyceride, total cholesterol and cholesterol esters were measured. Following treatment, food was removed for four hours and the animals were euthanized.

Blood was collected into EDTA-coated tubes to analyze plasma lipid and cholesterol profiles. Plasma total cholesterol (TC, Pointe Scientific, Canton, Mich.), free cholesterol (FC, Wako, Richmond, Va.) and triglyceride (TG, Wako, Richmond, Va.) concentrations were measured using enzymatic assays according to manufacturer's instructions. Cholesterol ester (CE) was calculated as the difference between TC and FC.

To assess atherosclerosis, the circulatory system was perfused following euthanasia with phosphate-buffered saline (PBS) before removing the heart and aorta. The upper one-third of the heart was dissected and embedded in Optimal Cutting Temperature Compound (Sakura Tissue-Tek, Torrance, Calif.), frozen, and stored at −80° C. Blocks were serially cut at 8 µm intervals and stained with hematoxylin and 0.5% Oil Red O (Sigma-Aldrich) to evaluate aortic sinus atherosclerotic intimal area. Atherosclerotic lesion area and Oil Red O positive area were quantified using Image-Pro Plus software (Media Cybemetics, Bethesda, Md.). Whole aorta (from sinotubular junction to iliac bifurcate) was dissected and fixed in 10% formalin, and the adventitia was cleaned. Aortas were opened along the longitudinal axis and pinned onto black silicon elastomer (Rubber-Cal, Santa Ana, Calif.) for the quantification of atherosclerotic lesion area. The percentage of total aortic surface covered with atherosclerotic lesions was quantified by Image-Pro Plus software (Media Cybemetics, Bethesda, Md.) and used to determine the total lesion area.

To assess macrophage infiltration, Sections of aortic sinus were immuno-stained with rat monoclonal antibody against macrophage-specific CD68 (Clone FA11, 1:75, AbD Serotec, Raleigh, N.C.) followed by staining with alkaline phosphatase-conjugated mouse anti-rat (for CD68, 1:50) secondary antibodies (Jackson ImmunoResearch laboratories, West Grove, Pa.). Control slides contain no primary antibody. The CD68-positive areas were analyzed using Image-Pro Plus software (Media Cybemetics, Bethesda, Md.).

Results

Figure 5:
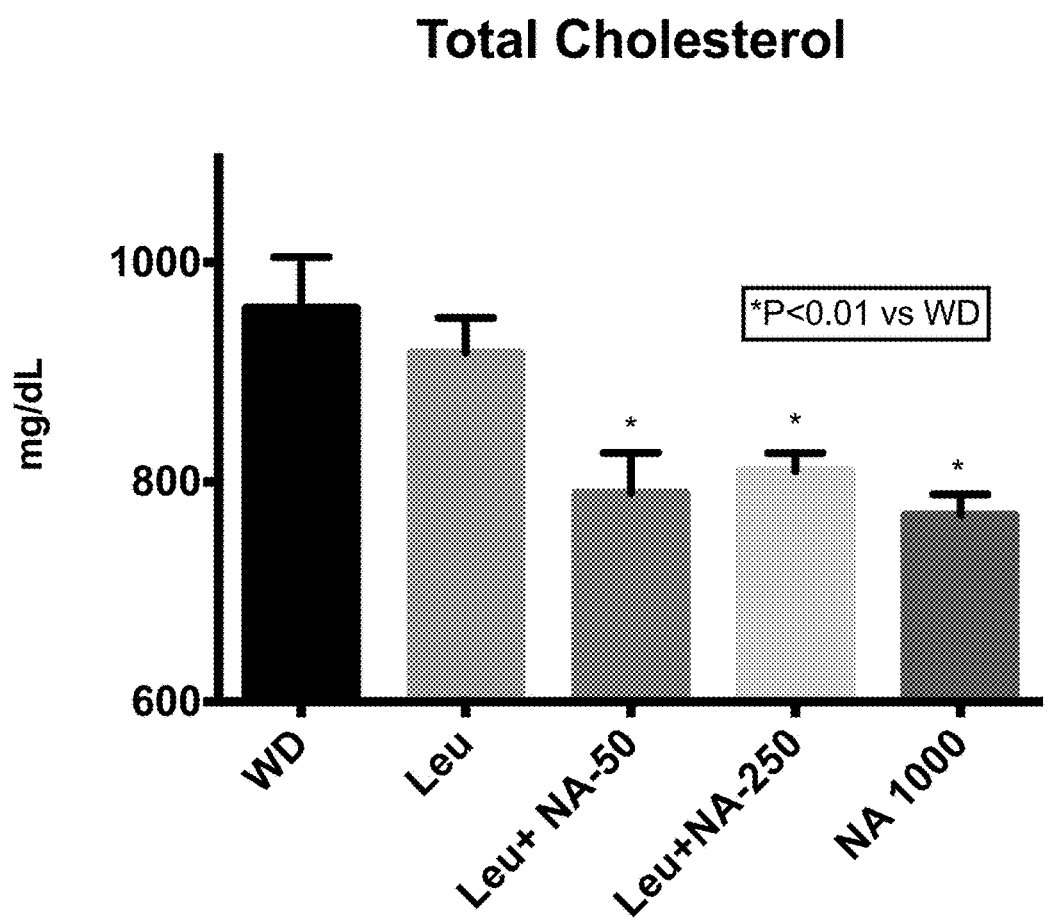
FIG. 5 illustrates the effects of four weeks treatment with Leucine (Leu, 24 g/kg diet), Leu (24 g/kg diet)+nicotinic acid (NA, 50 mg/kg diet), Leu (24 g/kg diet)+NA (250 mg/kg diet) and NA (1,000 mg/kg diet) added to a Western Diet (WD) on plasma total cholesterol in LDL receptor knockout mice.
Figure 6:
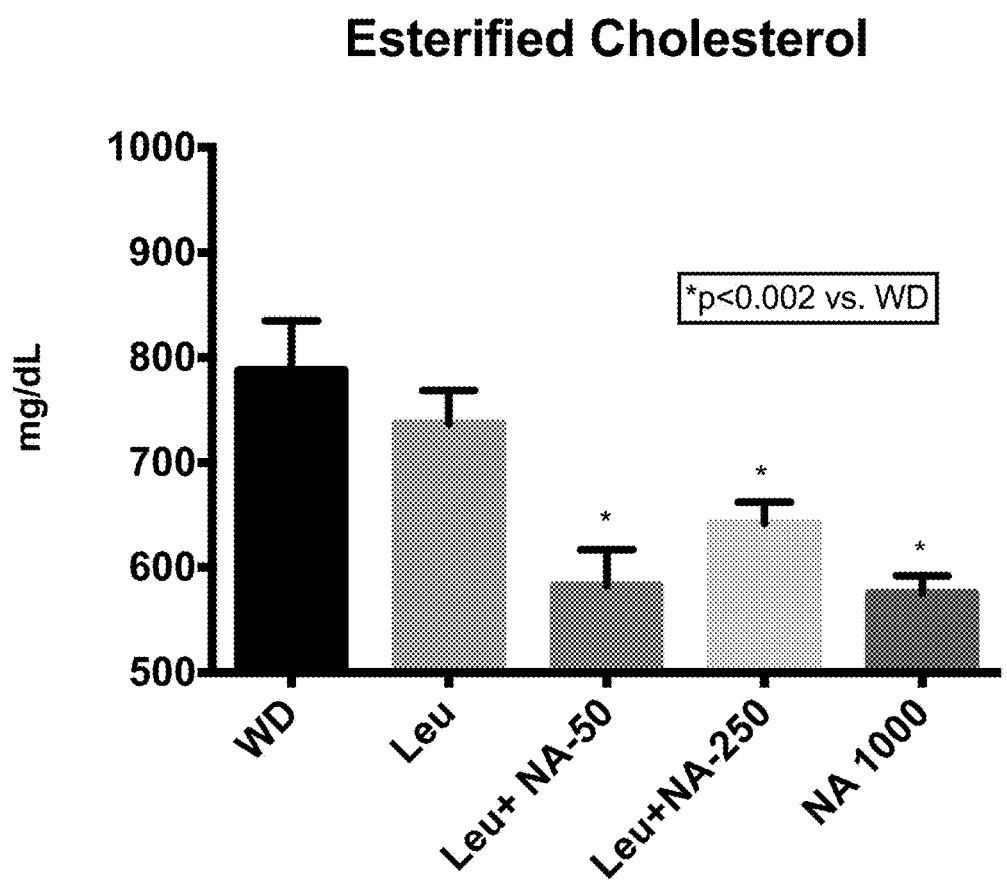
FIG. 6 illustrates the effects of four weeks treatment with Leucine (Leu, 24 g/kg diet), Leu (24 g/kg diet)+nicotinic acid (NA, 50 mg/kg diet), Leu (24 g/kg diet)+NA (250 mg/kg diet) and NA (1,000 mg/kg diet) added to a Western Diet (WD) on plasma cholesterol esters in LDL receptor knockout mice.
Figure 7:
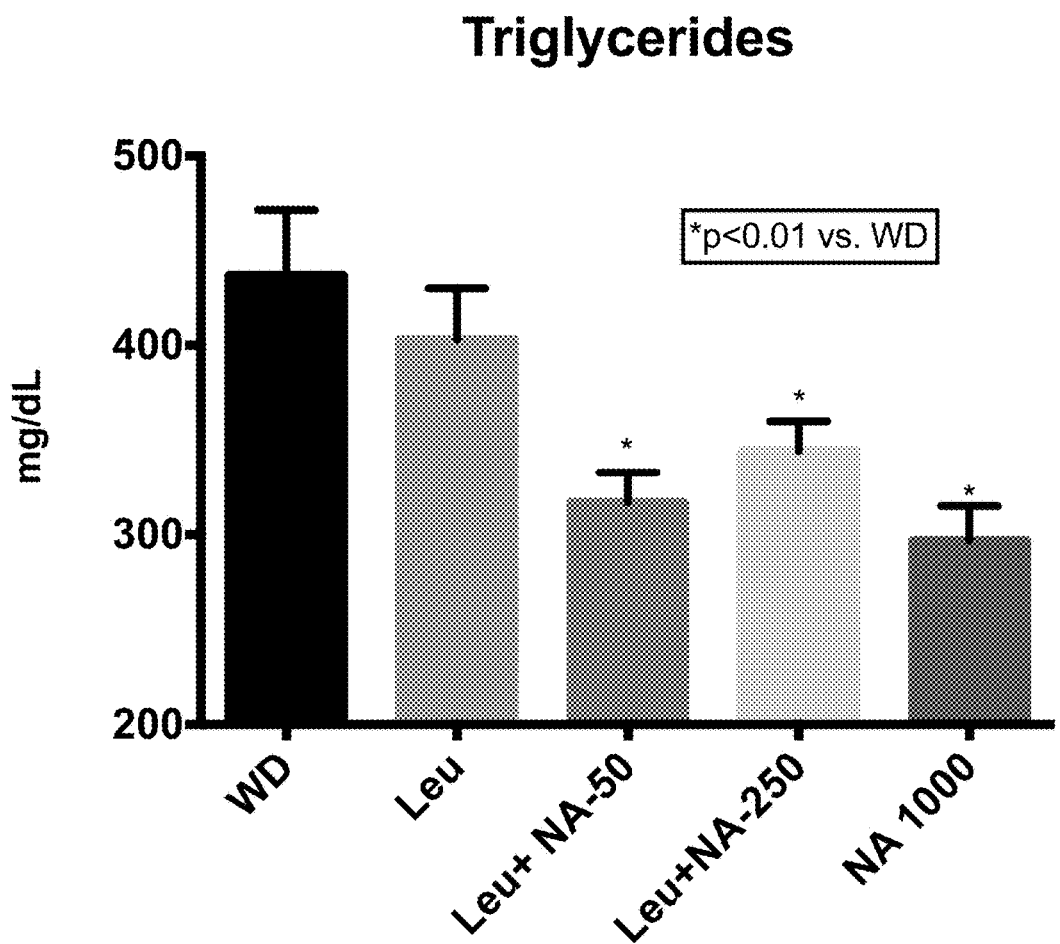
FIG. 7 illustrates the effects of four weeks treatment with Leucine (Leu, 24 g/kg diet), Leu (24 g/kg diet)+nicotinic acid (NA, 50 mg/kg diet), Leu (24 g/kg diet)+NA (250 mg/kg diet) and NA (1,000 mg/kg diet) added to a Western Diet (WD) on plasma triglycerides in LDL receptor knockout mice.
Figure 8:
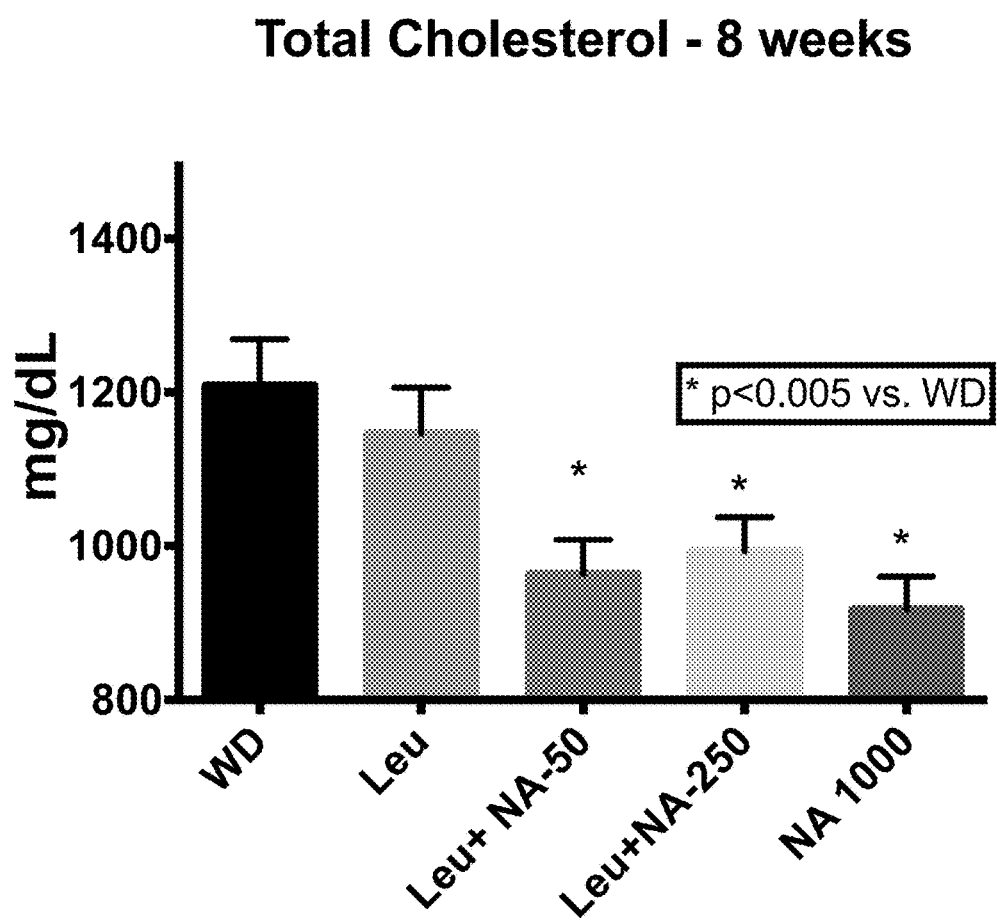
FIG. 8 illustrates the effects of eight weeks treatment with Leucine (Leu, 24 g/kg diet), Leu (24 g/kg diet)+nicotinic acid (NA, 50 mg/kg diet), Leu (24 g/kg diet)+NA (250 mg/kg diet) and NA (1,000 mg/kg diet) added to a Western Diet (WD) on plasma total cholesterol in LDL receptor knockout mice.
Figure 9:
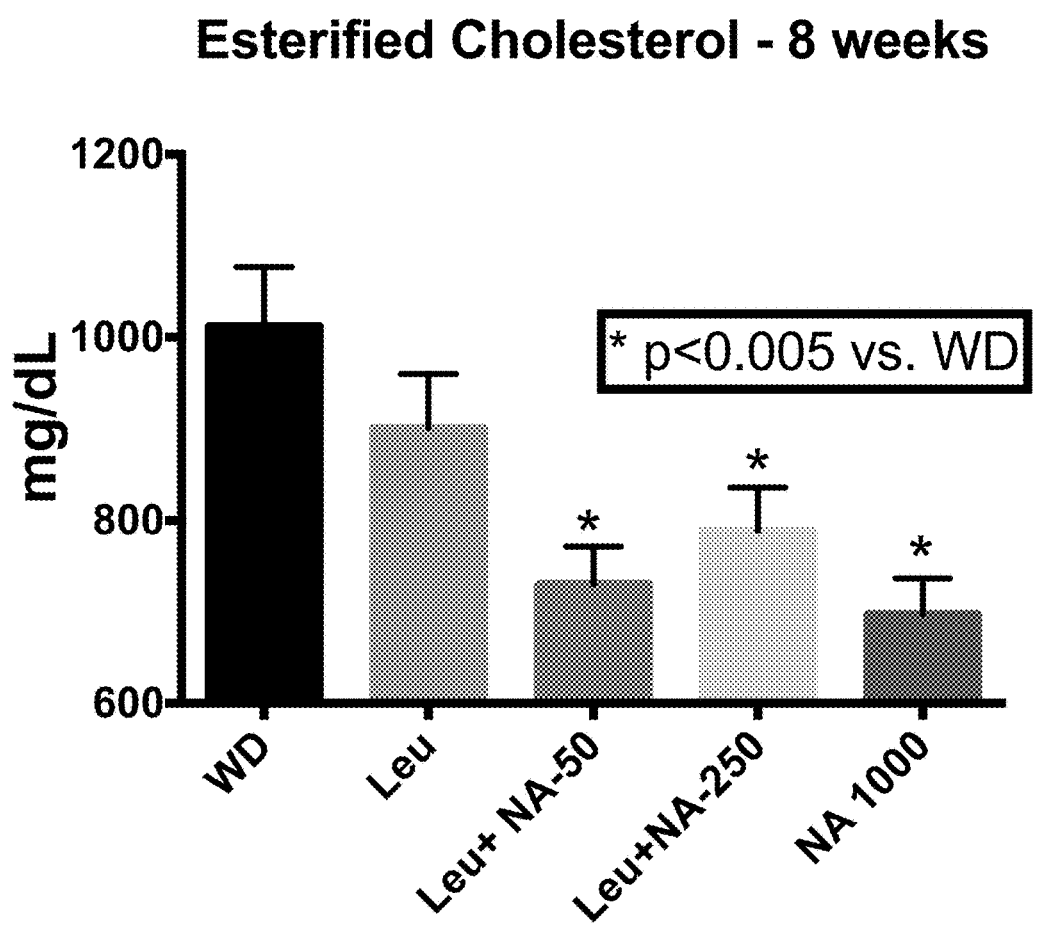
FIG. 9 illustrates the effects of eight weeks treatment with Leucine (Leu, 24 g/kg diet), Leu (24 g/kg diet)+nicotinic acid (NA, 50 mg/kg diet), Leu (24 g/kg diet)+NA (250 mg/kg diet) and NA (1,000 mg/kg diet) added to a Western Diet (WD) on plasma cholesterol esters in LDL receptor knockout mice.

The atherogenic western diet resulted in profound elevations in plasma cholesterol (FIG. 5), cholesterol esters (FIG. 6), and trigylcyerides (FIG. 7) following four weeks of treatment. Addition of a therapeutic dose of nicotinic acid (1,000 mg/kg diet) resulted in a 20% decrease in total cholesterol (p<0.01, FIG. 5). Although leucine exerted no independent effect on total cholesterol, addition of leucine to sub-therapeutic doses of nicotinic acid (50 or 250 mg/kg diet) resulted in comparable decreases in total cholesterol to that found with the therapeutic dose (p<0.01, FIG. 5). Similarly, addition of a therapeutic dose of nicotinic acid (1,000 mg/kg diet) resulted in a 28% decrease in cholesterol esters (p<0.002, FIG. 6), and a statistically comparable decrease was found when leucine was added to sub-therapeutic doses of nicotinic acid (50 or 250 mg/kg diet) (p<0.002, FIG. 6). Leucine exerted no independent effect on cholesterol esters. Plasma triglycerides were similarly affected. Addition of a therapeutic dose of nicotinic acid (1,000 mg/kg diet) resulted in a 32% decrease in plasma triglycerides (p<0.01, FIG. 7), and a statistically comparable decrease in triglycerides was found when leucine was added to sub-therapeutic doses of nicotinic acid (50 or 250 mg/kg diet) (p<0.01, FIG. 7). These differences were sustained at the final (eight week) time point (FIGS. 8 and 9).

Addition of a therapeutic dose of nicotinic acid (1,000 mg/kg diet) to the western diet resulted in a ~50% decrease in atherosclerotic lesion size (FIGS. 10-12) relative to the control fed the western diet alone.

Figure 10:
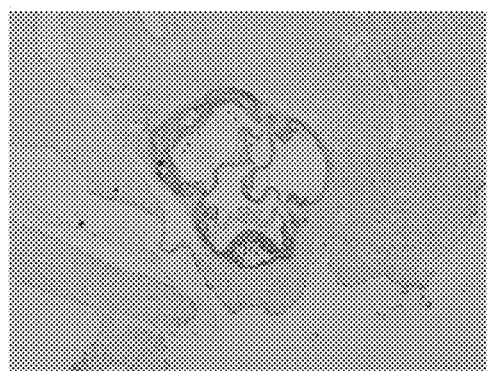
FIG. 10 illustrates the effects of eight weeks treatment with nicotine acid (1,000 mg/kg diet) on atherosclerotic lesion size in LDL receptor knockout mice. Shown are Oil Red O stained aortic histology slides.
Figure 10:
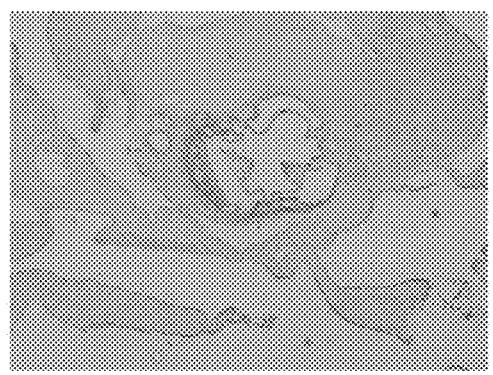
Figure 10:
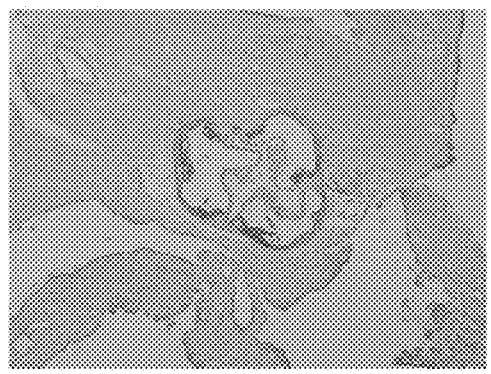
Figure 10:
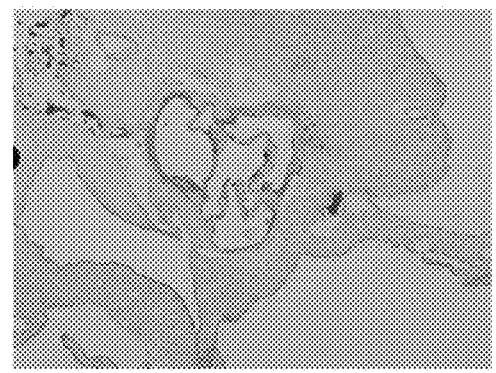
Figure 11:
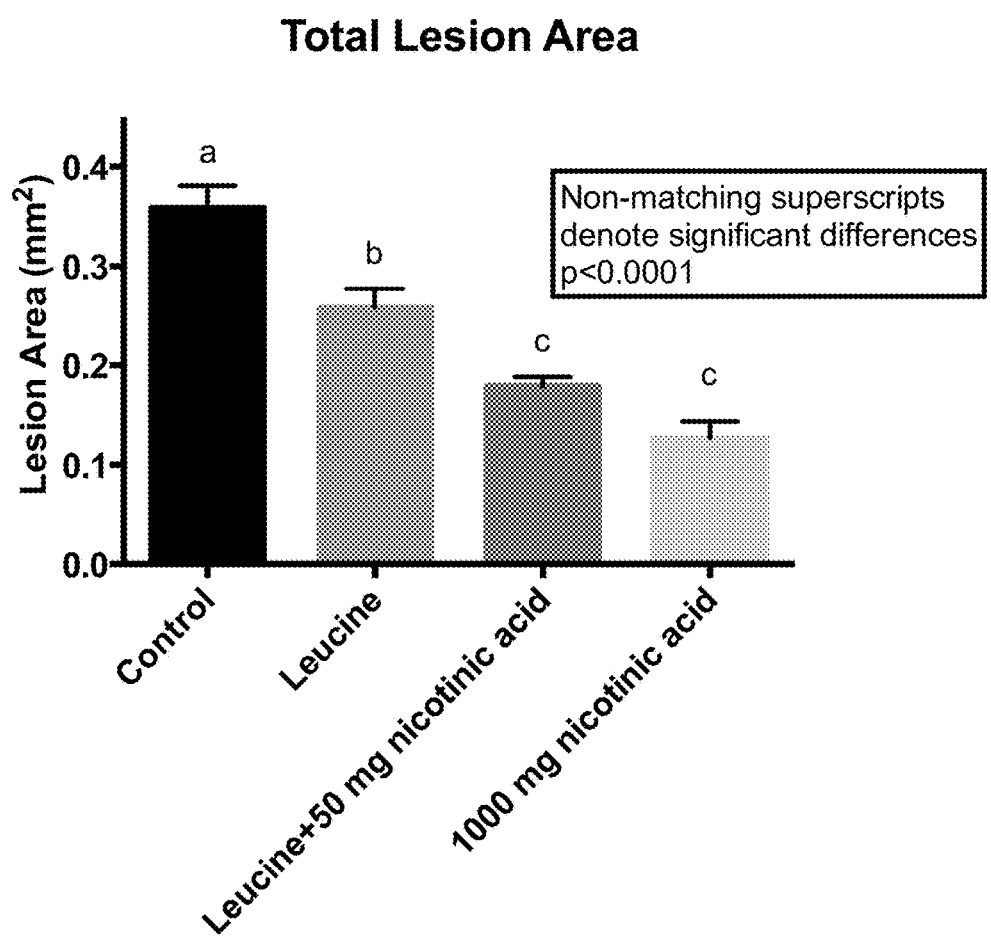
FIG. 11 illustrates the effects of eight weeks treatment with Leucine (Leu, 24 g/kg diet), Leu (24 g/kg diet)+ nicotinic acid (NA, 50 mg/kg diet), and NA (1,000 mg/kg diet) added to a Western Diet (WD) on total lesion area in LDL receptor knockout mice.

FIG. 10 shows Oil Red O stained aortic histology slides, which, in particular, the beneficial effects of administration of leucine along with 50 mg nicotinic acid in comparison to administration of leucine alone, 1000 mg nicotinic acid alone (positive control), and western diet alone (negative control). The histology slides shown in FIG. 10 were quantified as total lesion area in FIG. 11 and as lipid area (as observed by Oil Red O positive area) in FIG. 12. Addition of leucine to subtherapeutic dose of nicotinic acid (50 mg/kg diet) resulted in a comparable decrease in lesion and lipid area to that found with the therapeutic dose (p<0.0001, FIGS. 11-12). Leucine exerted an independent effect on plaque area, but this effect was significantly less than that of subtherapeutic nicotinic acid in combination with leucine (FIGS. 10-12).

Addition of a therapeutic dose of nicotinic acid (1,000 mg/kg diet) to the Western diet also resulted in a ~50% decrease in aortic macrophage infiltration (FIGS. 13-14). FIG. 13 shows CD68-positive area in representative histology slides, and this data is quantified as % CD68 positive area in the lesion. Addition of leucine to subtherapeutic dose of nicotinic acid (50 mg/kg diet) resulted in a comparable decrease in macrophage infiltration to that found with the therapeutic dose (p<0.0001, FIGS. 13-14). However, leucine also exerted a significant independent effect on reducing macrophage infiltration; this effect was not as great as the therapeutic dose of nicotinic acid, but was also not significantly different from the leucine-nicotinic acid combination (FIG. 14).

Example 8

Effects of Leucine-Nicotinic Acid on the Lifespan in *C. elegans*

The use of a composition comprising (a) nicotinic acid and (b) leucine as described herein was investigated, wherein the composition comprises free leucine and a sub-therapeutic amount of nicotinic acid. The composition synergistically extended the lifespan in a subject after administration of the composition to the subject.

Worms (N2 Bristol wild-type) were obtained from the *Caenorhabditis* Genetics Center (CGC) at the University of Minnesota and grown on standard NGM plates with *E. coli* (OP50) as food source at 20° C. Eggs were hatched on a starved plate overnight. Then synchronized L1 larvae were transferred to *E. coli* fed NGM plates containing indicated treatments for about 35 hours to reach L4/young adult stage. To study lifespan, 50 young adult worms were placed on NGM agar plates seeded with *E. coli* strain OP-50 (=day 1 of study). All treatments were added with the indicated concentrations to *E. coli* the agar plates. Treatments included 10 nM of nicotinic acid and 0.5 mM of leucine.

The worms were maintained at 20° C. throughout the duration of the study. Worms were transferred to new plates daily to eliminate progeny. Worms were scored as dead if they did not respond to repeated touch with a platinum pick. The study was continued until the last animal was dead. Data were analyzed via Kaplan-Meier survival curves using Prism 6 (GraphPad Software) and statistical significance was determined by the Log-rank (Mantel-Cox) test.

It was found that leucine (0.5 mM) and nicotinic acid (10 nM) each exerted no independent effect on lifespan, but when combined extended maximal lifespan under basal conditions, and extended median lifespan by 28% under conditions of oxidative stress induced by administration of paraquat (0.2 mM) (FIG. 15).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of lowering total cholesterol level or total lipid content in a subject in need thereof, the method comprising administering to the subject a dose of a one or two part composition comprising:
   a) at least 250 mg of leucine and/or at least 25 mg of one or more leucine metabolites, wherein the leucine metabolite is selected from the group consisting of keto-isocaproic acid (KIC), alpha-hydroxy-isocaproic acid, and hydroxymethylbutyrate (HMB); and
   b) at least 1 mg of nicotinic acid and/or nicotinamide riboside and/or one or more nicotinic acid metabolites, wherein the nicotinic acid metabolite is selected from the group consisting of nicotinyl CoA, nicotinuric acid, nicotinate mononucleotide, nicotinate adenine dinuecleotide, and nicotinamide adenine dinucleotide,
   wherein each of (a) and (b) are free of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine, and
   wherein (a) and (b) are administered either simultaneously or in close temporal proximity.

2. The method of claim 1, wherein the composition is substantially free of nicotinamide.

3. The method of claim 1, wherein the component (a) in the composition is leucine and the component (b) in the composition is nicotinic acid.

4. The method of claim 1, wherein the amount of leucine and/or one or more leucine metabolites in the composition is less than 1300 mg.

5. The method of claim 1, wherein the amount of nicotinic acid and/or nicotinamide riboside and/or one or more nicotinic acid metabolites in the composition is less than 250 mg.

6. The method of claim 1, wherein the amount of nicotinic acid and/or nicotinamide riboside and/or one or more nicotinic acid metabolites in the composition is between 1-100 mg.

7. The method of claim 1, wherein the composition further comprises resveratrol.

8. The method of claim 1, wherein a molar ratio of component (a) to (b) in the composition is greater than 5.

9. The method of claim 1, wherein the composition is a tablet, a capsule, or a pill.

10. The method of claim 1, wherein the composition further comprising one or more therapeutic agents selected from the group consisting of HMG-CoA inhibitor, fibrate, bile acid sequestrant, ezetimibe, lomitapide, phytosterols, CETP antagonist, orlistat, and any combination thereof.

11. The method of claim 1, wherein the dose is a unit dose.

12. A method of reducing atherosclerotic plaque size in a subject in need thereof, comprising administering a one or two part composition comprising:
   a) at least 250 mg of leucine and/or at least 25 mg, of one or more leucine metabolites, wherein the leucine metabolite is selected from the group consisting of keto-isocaproic acid (KIC), alpha-hydroxy-isocaproic acid, and hydroxymethylbutyrate (HMB); and
   b) at least 1 mg of nicotinic acid and/or nicotinamide riboside and/or one or more nicotinic acid metabolites, wherein the nicotinic acid metabolite is selected from the group consisting of nicotinyl CoA, nicotinuric acid, nicotinate mononucleotide, nicotinate adenine dinucleotide, and nicotinamide adenine dinucleotide,
   wherein each of (a) and (b) are free of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine, and
   wherein (a) and (b) are administered either simultaneously or in close temproal proximity.

13. The method of claim 12, wherein the amount of leucine and/or one or more leucine metabolites is less than 1300 mg.

14. The method of claim 12, wherein the amount of nicotinic acid and/or nicotinamide riboside and/or nicotinic acid metabolites is less than 250 mg.

15. The method of claim 12, wherein the amount of nicotinic acid and/or nicotinamide riboside and/or nicotinic acid metabolites is between 1-100 mg.

16. The method of claim 12, wherein the amount of nicotinic acid and/or nicotinamide riboside and/or nicotinic acid metabolites is less than 25 mg.

17. The method of claim 12, wherein the composition is administered to the subject for at least 1 year.

18. The method of claim 12, wherein the dose is a unit dose.

19. A method of reducing a side effect of nicotinic acid and/or nicotinamide riboside and/or one or more nicotinic acid metabolites wherein the side effect is characterized by an increase in cutaneous vasodilation in a subject administered with nicotinic acid and/or nicotinamide riboside and/or the one or more nicotinic acid metabolites, comprising administering a one or two part composition comprising:
   a) at least 250 mg of leucine and/or at least 25 mg of one or more leucine metabolites, wherein the leucine metabolite is selected from the group consisting of keto-isocaproic acid (KIC), alpha-hydroxy-isocaproic acid, and hydroxymethtlbutyrate (HMB); and
   b) at least 1 mg of nicotinic acid and/or nicotinamide riboside and/or one or more nicotinic acid metabolites, wherein the nicotinic acid metabolite is selected from the group consisting of nicotinyl CoA, nicotinuric acid, nicotinate mononucleotide, nicotinate adenine dinucleotide, and nicotinamide adenine dinucleotide,
   wherein each of (a) and (b) are free of alanine, arginine, asparagine, aspartic acid, cysteine, glutamic acid, glutamine, glycine, histidine, lysine, methionine, phenylalanine, proline, serine, threonine, tryptophan, valine, isoleucine and tyrosine, and
   wherein (a) and (b) are administered either simultaneously or in close temporal proximity.

20. The method of claim 19, wherein the composition is administered orally.

21. The method of claim 19, wherein the effective amount comprises at least 500 mg of leucine and/or at least 200 mg of the one or more leucine metabolites.

22. The method of claim 19, wherein the composition further comprising one or more therapeutic agents selected from the group consisting of HMG-CoA inhibitor, fibrate, bile acid sequestrant, ezetimibe, lomitapide, phytosterols, CETP antagonist, orlistat, and any combination thereof.

23. The method of claim 19, wherein nicotinic acid and/or nicotinamide riboside and/or one or more nicotinic acid metabolites is in a sub-therapeutic amount if administered alone.

24. The method of claim 19, wherein nicotinic acid and/or nicotinamide riboside and/or one or more nicotinic acid metabolites is in an amount that is less than 1 g.

25. The method of claim 19, wherein nicotinic acid and/or nicotinamide riboside and/or one or more nicotinic acid metabolites is in an amount that is less than 250 mg.

26. The method of claim 19, wherein the amount of nicotinic acid and or nicotinamide riboside and/or one or more nicotinic acid metabolites is between 1-100 mg.

27. The method of claim 19, wherein the amount of nicotinic acid and or nicotinamide riboside and/or one or more nicotinic acid metabolites is capable of achieving a serum level of nicotinic acid and/or nicotinamide riboside and/or one or more nicotinic acid metabolites that is between about 1-100 nM.

* * * * *